United States Patent
Kautz

(10) Patent No.: US 9,387,205 B2
(45) Date of Patent: Jul. 12, 2016

(54) HYDROXY-6-HETEROARYLPHEN-ANTHRIDINES AND THEIR USE AS PDE4 INHIBITORS

(71) Applicant: TAKEDA GMBH, Constance (DE)

(72) Inventor: Ulrich Kautz, Allensbach (DE)

(73) Assignee: TAKEDA GMBH, Konstanz (DE)

( * ) Notice: Subject to any disclaimer, the term of this patent is extended or adjusted under 35 U.S.C. 154(b) by 0 days.

(21) Appl. No.: 14/834,709

(22) Filed: Aug. 25, 2015

(65) Prior Publication Data

US 2015/0352096 A1 Dec. 10, 2015

Related U.S. Application Data

(63) Continuation of application No. 14/508,077, filed on Oct. 7, 2014, now Pat. No. 9,149,479, which is a continuation of application No. 13/873,670, filed on Apr. 30, 2013, now Pat. No. 8,883,818, which is a continuation of application No. 13/661,897, filed on Oct. 26, 2012, now Pat. No. 8,455,653, which is a continuation of application No. 13/111,544, filed on May 19, 2011, now Pat. No. 8,324,391, which is a continuation of application No. 10/590,803, filed as application No. PCT/EP2005/050931 on Mar. 2, 2005, now Pat. No. 8,003,798.

(30) Foreign Application Priority Data

Mar. 3, 2004 (EP) ..................... 04004973
Dec. 7, 2004 (EP) ..................... 04106359

(51) Int. Cl.

| | | |
|---|---|---|
| C07D 211/68 | (2006.01) | |
| C07D 211/80 | (2006.01) | |
| A01N 43/42 | (2006.01) | |
| A61K 31/44 | (2006.01) | |
| A61K 31/473 | (2006.01) | |
| C07D 401/04 | (2006.01) | |
| C07D 401/14 | (2006.01) | |
| C07D 405/04 | (2006.01) | |
| C07D 413/04 | (2006.01) | |
| C07D 417/04 | (2006.01) | |
| C07D 417/14 | (2006.01) | |
| C07D 471/04 | (2006.01) | |
| A61K 31/4985 | (2006.01) | |
| A61K 31/506 | (2006.01) | |
| A61K 31/5377 | (2006.01) | |

(52) U.S. Cl.
CPC ........... *A61K 31/473* (2013.01); *A61K 31/4985* (2013.01); *A61K 31/506* (2013.01); *A61K 31/5377* (2013.01); *C07D 401/04* (2013.01); *C07D 401/14* (2013.01); *C07D 405/04* (2013.01); *C07D 413/04* (2013.01); *C07D 417/04* (2013.01); *C07D 417/14* (2013.01); *C07D 471/04* (2013.01)

(58) Field of Classification Search
USPC .......................................... 514/298; 546/285
See application file for complete search history.

(56) References Cited

U.S. PATENT DOCUMENTS

| | | | |
|---|---|---|---|
| 6,008,215 | A | 12/1999 | Flockerzi |
| 6,121,279 | A | 9/2000 | Gutterer |
| 6,127,378 | A | 10/2000 | Gutterer |
| 6,191,138 | B1 | 2/2001 | Gutterer |
| 6,214,839 | B1 | 4/2001 | Gutterer |
| 6,306,869 | B1 | 10/2001 | Flockerzi |
| 6,410,551 | B1 | 6/2002 | Gutterer |
| 6,476,025 | B1 | 11/2002 | Gutterer |
| 6,479,505 | B1 | 11/2002 | Gutterer |
| 6,534,518 | B1 | 3/2003 | Gutterer |
| 6,534,519 | B1 | 3/2003 | Gutterer |
| 6,538,005 | B2 | 3/2003 | Gutterer |

(Continued)

FOREIGN PATENT DOCUMENTS

| | | |
|---|---|---|
| EP | 0 490 823 A1 | 6/1992 |
| EP | 1 270 577 A1 | 1/2003 |
| WO | 97/28131 A1 | 8/1997 |
| WO | 97/35854 A1 | 10/1997 |
| WO | 98/21208 A1 | 5/1998 |
| WO | 98/40382 A1 | 9/1998 |
| WO | 98/55481 A1 | 12/1998 |
| WO | 99/05111 A1 | 2/1999 |
| WO | 99/05112 A1 | 2/1999 |
| WO | 99/05113 A1 | 2/1999 |

(Continued)

OTHER PUBLICATIONS

Bäumer, et al., "Highly Selective Phosphodiesterase 4 Inibitors for the Treatment of Allergic Skin Diseases and Psoriasis", Inflammation and Allergy—Drug Targets, 2006, vol. 6, No. 1, pp. 17-26.

(Continued)

*Primary Examiner* — Marcos Sznaidman
(74) *Attorney, Agent, or Firm* — Nath, Goldberg & Meyer; Joshua B. Goldberg; Scott H. Blackman

(57) ABSTRACT

Compounds of the formula Ia*****

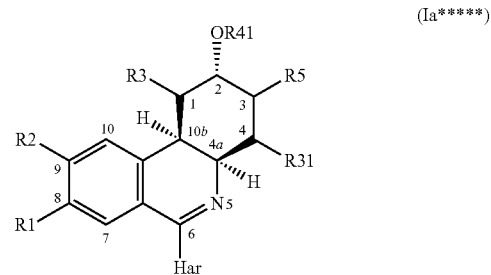

in which the substituents have the definitions provided in the specification, are novel, effective PDE4 inhibitors, useful in the treatment of atopic eczema.

5 Claims, No Drawings

(56) References Cited

U.S. PATENT DOCUMENTS

| | | | |
|---|---|---|---|
| 6,884,802 B2 | 4/2005 | Schmidt | |
| 6,936,622 B2 | 8/2005 | Flockerzi | |
| 7,329,676 B2 | 2/2008 | Kautz et al. | |
| 7,423,046 B2 | 9/2008 | Kautz et al. | |
| 7,585,872 B2 | 9/2009 | Kautz et al. | |
| 7,632,844 B2 | 12/2009 | Kautz et al. | |
| 7,718,668 B2 | 5/2010 | Kautz et al. | |
| 8,003,798 B2 | 8/2011 | Kautz | |
| 2004/0038979 A1 | 2/2004 | Schmidt | |
| 2004/0097537 A1 | 5/2004 | Flockerzi | |
| 2005/0239817 A1 | 10/2005 | Kautz et al. | |
| 2005/0239818 A1 | 10/2005 | Kautz et al. | |
| 2006/0116518 A1 | 6/2006 | Flockerzi et al. | |
| 2007/0167482 A1 | 7/2007 | Kautz | |
| 2007/0185149 A1 | 8/2007 | Kautz | |
| 2007/0191413 A1 | 8/2007 | Kautz | |
| 2007/0191414 A1 | 8/2007 | Kautz | |
| 2007/0259909 A1 | 11/2007 | Kautz | |
| 2008/0319067 A1 | 12/2008 | Kautz et al. | |
| 2009/0170892 A1 | 7/2009 | Kautz et al. | |
| 2010/0190818 A1 | 7/2010 | Kautz et al. | |
| 2011/0257169 A1 | 10/2011 | Kautz | |
| 2011/0257221 A1 | 10/2011 | Kautz | |

FOREIGN PATENT DOCUMENTS

| | | | |
|---|---|---|---|
| WO | 99/57118 | A1 | 11/1999 |
| WO | 00/12501 | A1 | 3/2000 |
| WO | 00/42017 | A1 | 7/2000 |
| WO | 00/42018 | A1 | 7/2000 |
| WO | 00/42019 | A1 | 7/2000 |
| WO | 00/42020 | A1 | 7/2000 |
| WO | 00/42034 | A1 | 7/2000 |
| WO | 01/51470 | A1 | 7/2001 |
| WO | 02/05616 | A1 | 1/2002 |
| WO | 02/06238 | A1 | 1/2002 |
| WO | 02/06270 | A1 | 1/2002 |
| WO | 02/066476 | A1 | 8/2002 |
| WO | 2004/018431 | A2 | 3/2004 |
| WO | 2004/018465 | A2 | 3/2004 |
| WO | 2004/019944 | A1 | 3/2004 |
| WO | 2004/019945 | A1 | 3/2004 |
| WO | 2005/077906 | A1 | 8/2005 |
| WO | 2005/084104 | A2 | 9/2005 |
| WO | 2005/085203 | A1 | 9/2005 |
| WO | 2005/085225 | A1 | 9/2005 |
| WO | 2005/087744 | A1 | 9/2005 |
| WO | 2005/087745 | A1 | 9/2005 |
| WO | 2005/090311 | A1 | 9/2005 |
| WO | 2006/092422 | A1 | 9/2006 |

OTHER PUBLICATIONS

Cecil textbook of Medicine, edited by Bennet, J. C., and Plum, F., 20th Edition, 1996, vol. 1, pp. 1004-1010.

Dörwald, F.Z., "Side Reactions in Organic Synthesis: A guide to successful synthesis design", 2005, Wiley, VCH, Weinheim, p. IX of Preface.

Dyke, et al., "Update on the therapeutic potential of PDE4 inhibitors", Expert Opinion on Investigational Drugs, 2002, vol. 11, No. 1, pp. 1-13.

Govindachari, et al., "Application of the Bruckner Method to the Synthesis of Phenanthridine Derivatives", J Chem. Soc., 1956, pp. 4280-4283.

Kametani, et al., "Cyclised Products in the Synthesis of 6-Substituted Phenanthridines by Phenolic Cyclisation", J Chem. Soc., 1971, pp. 1805-1808.

Kroegel, et al., Expert Opinion Investig. Drugs, 2007, vol. 16, pp. 109-124.

Montana, J.G., et al., "Chapter 5. Phosphodiesterase 4 Inhibitors", Annual Reports Medicinal Chemistry, 2001, vol. 36, pp. 41-56.

Patel, et al., Expert Opinion on Investigational Drugs, 2003, vol. 12, pp. 623-633.

Schmidt, et al., "The Phosphodiesterase 4 Inhibitor Roflumilast is Effective in the Treatment of Allergic Rhinitis", J. Allergy Clin. Immunol., 2001, vol. 108, pp. 530-536.

Souness, et al., "Immunosuppressive and Anti-Inflammatory Effects of Cyclic AMP Phosphodiesterase (PDE) Type 4 Inhibitors", Immunopharmacology, 2000, vol. 47, pp. 127-162.

Souness, J. E., et al., Pig aortic endothelial-cell cyclic nucleotide phosphodiesterases. Biochem. J. (1990) 266, 127-132.

Sugasawa, et al., "Synthese Partiell Hydrierter Phenanthridin-Derivative (I)", Berichte der deutschen chemischen Gesellschaft (Chem. Ber.), 1939, vol. 4, pp. 675-678.

Vippagunta, et al., Advanced Drug Delivery Reviews, 2001, vol. 48, pp. 3-26.

West, Anthony R., "Solid State Chemistry and its Applications", Wiley, New York, 1988, pp. 358 and 365.

HYDROXY-6-HETEROARYLPHENANTHRIDINES AND THEIR USE AS PDE4 INHIBITORS

This application is a continuation application of Ser. No. 14/508,077, filed Oct. 7, 2014, which is a continuation application of Ser. No. 13/873,670, filed Apr. 30, 2013, which is a continuation application of Ser. No. 13/661,897, filed Oct. 26, 2012, which is a continuation application of Ser. No. 13/111,544, filed May 19, 2011, which is a continuation application of Ser. No. 10/590,803, filed Aug. 25, 2006, which was filed under 35 U.S.C. 371 as a national stage of PCT/EP2005/050931, filed Mar. 2, 2005.

FIELD OF APPLICATION OF THE INVENTION

The Sequence Listing submitted in text format (.txt) filed on Aug. 25, 2015, named "14508077-1 raw_SequenceListing.txt", (created on Aug. 25, 2015, 1 KB), is incorporated herein by reference.

The invention relates to novel hydroxy-6-heteroarylphenanthridine derivatives, which are used in the pharmaceutical industry for the production of pharmaceutical compositions.

KNOWN TECHNICAL BACKGROUND

The International Patent applications WO99/57118 and WO02/05616 describe 6-phenylphenanthridines as PDE4 inhibitors.

In the International Patent application WO99/05112 substituted 6-alkylphenanthridines are described as bronchial therapeutics.

In the European Patent application EP 0490823 dihydroisoquinoline derivatives are described which are said to be useful in the treatment of asthma.

The International Patent application WO00/42019 discloses 6-arylphenanthridines as PDE4 inhibitors.

The International Patent application WO02/06270 discloses 6-heteroarylphenanthridines as PDE4 inhibitors.

The International Patent application WO97/35854 discloses phenanthridines substituted in the 6-position as PDE4 inhibitors.

The International Patent applications WO2004/019944 and WO2004/019945 disclose hydroxy-substituted 6-phenylphenanthridines as PDE4 inhibitors.

DESCRIPTION OF THE INVENTION

It has now been found that the novel 2- or 3-hydroxy-6-heteroarylphenanthridines described in greater detail below differ from the previously known compounds by unanticipated and sophisticated structural alterations and have surprising and particularly advantageous properties.

The invention thus relates in a first aspect (aspect A) to compounds of formula I,

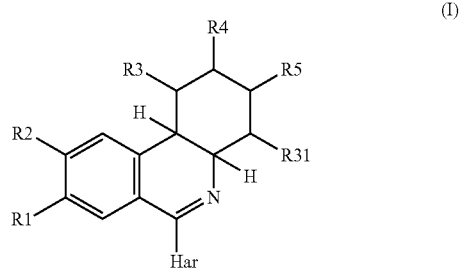

in which
R1 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy,
R2 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy,
or in which
R1 and R2 together are a 1-2C-alkylenedioxy group,
R3 is hydrogen or 1-4C-alkyl,
R31 is hydrogen or 1-4C-alkyl,
either, in a first embodiment (embodiment a) according to the present invention,
R4 is —O—R41, in which
R41 is hydrogen, 1-4C-alkyl, 1-4C-alkoxy-1-4C-alkyl, hydroxy-2-4C-alkyl, 1-7C-alkylcarbonyl, or completely or predominantly fluorine-substituted 1-4C-alkyl, and
R5 is hydrogen or 1-4C-alkyl,
or, in a second embodiment (embodiment b) according to the present invention,
R4 is hydrogen or 1-4C-alkyl, and
R5 is —O—R51, in which
R51 is hydrogen, 1-4C-alkyl, 1-4C-alkoxy-1-4C-alkyl, hydroxy-2-4C-alkyl, 1-7C-alkylcarbonyl, or completely or predominantly fluorine-substituted 1-4C-alkyl,
Har is optionally substituted by R6 and/or R7 and/or R8, and is a 5- to 10-membered monocylic or fused bicyclic unsaturated or partially saturated heteroaryl radical comprising 1 to 4 heteroatoms selected independently from the group consisting of oxygen, nitrogen and sulfur, in which
R6 is halogen, 1-4C-alkyl, 1-4C-alkoxy, 1-4C-alkoxy-2-4C-alkoxy, 1-4C-alkylthio, sulfanyl, cyano, 1-4C-alkoxycarbonyl, carboxyl, hydroxyl, oxo, -A-N(R61)R62, pyridyl, or completely or partially fluorine-substituted 1-4C-alkyl, in which
A is a bond or 1-4C-alkylene,
R61 is hydrogen or 1-4C-alkyl,
R62 is hydrogen or 1-4C-alkyl,
or R61 and R62 together and with inclusion of the nitrogen atom, to which they are attached, form a heterocyclic ring Het1, in which
Het1 is optionally substituted by R611, and is a 3- to 7-membered saturated or unsaturated monocyclic heterocyclic ring radical comprising the nitrogen atom, to which R61 and R62 are bonded, and optionally one to three further heteroatoms independently selected from the group consisting of oxygen, nitrogen and sulfur, in which
R611 is 1-4C-alkyl,
R7 is 1-4C-alkyl, 1-4C-alkoxy, 1-4C-alkoxy-2-4C-alkoxy, 1-4C-alkylthio, sulfanyl, hydroxyl, oxo, amino or mono- or di-1-4C-alkylamino,
R8 is halogen, 1-4C-alkyl or 1-4C-alkoxy,
and the salts, the N-oxides and the salts of the N-oxides of these compounds.

The invention further relates in a second aspect (aspect B), which is an embodiment of aspect A, to compounds of formula I,
in which
R1 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy,
R2 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy,
or in which
R1 and R2 together are a 1-2C-alkylenedioxy group,
R3 is hydrogen or 1-4C-alkyl,
R31 is hydrogen or 1-4C-alkyl,
either, in a first embodiment (embodiment a) according to the present invention,
R4 is —O—R41, in which
R41 is hydrogen, 1-4C-alkyl, 1-4C-alkoxy-1-4C-alkyl, hydroxy-2-4C-alkyl, 1-7C-alkylcarbonyl, or completely or predominantly fluorine-substituted 1-4C-alkyl, and
R5 is hydrogen or 1-4C-alkyl,
or, in a second embodiment (embodiment b) according to the present invention,
R4 is hydrogen or 1-4C-alkyl, and
R5 is —O—R51, in which
R51 is hydrogen, 1-4C-alkyl, 1-4C-alkoxy-1-4C-alkyl, hydroxy-2-4C-alkyl, 1-7C-alkylcarbonyl, or completely or predominantly fluorine-substituted 1-4C-alkyl,
Har is optionally substituted by R6 and/or R7 and/or R8, and is a 5- to 10-membered monocylic or fused bicyclic unsaturated or partially saturated heteroaryl radical comprising 1 to 4 heteroatoms selected independently from the group consisting of oxygen, nitrogen and sulfur, in which
R6 is halogen, 1-4C-alkyl, 1-4C-alkoxy, 1-4C-alkoxy-2-4C-alkoxy, 1-4C-alkylthio, cyano, 1-4C-alkoxycarbonyl, carboxyl, hydroxyl, -A-N(R61)R62, pyridyl, or completely or partially fluorine-substituted 1-4C-alkyl, in which
A is a bond or 1-4C-alkylene,
R61 is hydrogen or 1-4C-alkyl,
R62 is hydrogen or 1-4C-alkyl,
or R61 and R62 together and with inclusion of the nitrogen atom, to which they are attached, form a heterocyclic ring Het1, in which
Het1 is optionally substituted by R611, and is a 3- to 7-membered saturated or unsaturated monocyclic heterocyclic ring radical comprising the nitrogen atom, to which R61 and R62 are bonded, and optionally one to three further heteroatoms independently selected from the group consisting of oxygen, nitrogen and sulfur, in which
R611 is 1-4C-alkyl,
R7 is 1-4C-alkoxy, 1-4C-alkoxy-2-4C-alkoxy, 1-4C-alkylthio, hydroxyl, amino or mono- or di-1-4C-alkylamino,
R8 is halogen,
and the salts, the N-oxides and the salts of the N-oxides of these compounds.

The invention further relates in a third aspect (aspect C), which is an embodiment of aspect A, to compounds of formula I,
in which
R1 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy,
R2 is hydroxyl, 1-4C-alkoxy, 3-7C-cycloalkoxy, 3-7C-cycloalkylmethoxy, 2,2-difluoroethoxy, or completely or predominantly fluorine-substituted 1-4C-alkoxy,
or in which
R1 and R2 together are a 1-2C-alkylenedioxy group,
R3 is hydrogen or 1-4C-alkyl,
R31 is hydrogen or 1-4C-alkyl,
either, in a first embodiment (embodiment a) according to the present invention,
R4 is —O—R41, in which
R41 is hydrogen, 1-4C-alkyl, 1-4C-alkoxy-1-4C-alkyl, hydroxy-2-4C-alkyl, 1-7C-alkylcarbonyl, or completely or predominantly fluorine-substituted 1-4C-alkyl, and
R5 is hydrogen or 1-4C-alkyl,
or, in a second embodiment (embodiment b) according to the present invention,
R4 is hydrogen or 1-4C-alkyl, and
R5 is —O—R51, in which
R51 is hydrogen, 1-4C-alkyl, 1-4C-alkoxy-1-4C-alkyl, hydroxy-2-4C-alkyl, 1-7C-alkylcarbonyl, or completely or predominantly fluorine-substituted 1-4C-alkyl,
Har is optionally substituted by R6 and/or R7 and/or R8, and is a pyridinyl, pyrimidinyl, pyrazinyl or pyridazinyl radical, in which
R6 is halogen, 1-4C-alkyl, 1-4C-alkoxy, 1-4C-alkoxy-2-4C-alkoxy, 1-4C-alkylthio, sulfanyl, cyano, 1-4C-alkoxycarbonyl, carboxyl, hydroxyl, oxo, -A-N(R61)R62, pyridyl, or completely or partially fluorine-substituted 1-4C-alkyl, in which
A is a bond or 1-4C-alkylene,
R61 is hydrogen or 1-4C-alkyl,
R62 is hydrogen or 1-4C-alkyl,
or R61 and R62 together and with inclusion of the nitrogen atom, to which they are attached, form a heterocyclic ring Het1, in which
Het1 is optionally substituted by R611, and is a 3- to 7-membered saturated or unsaturated monocyclic heterocyclic ring radical comprising the nitrogen atom, to which R61 and R62 are bonded, and optionally one to three further heteroatoms independently selected from the group consisting of oxygen, nitrogen and sulfur, in which
R611 is 1-4C-alkyl,
R7 is 1-4C-alkyl, 1-4C-alkoxy, 1-4C-alkoxy-2-4C-alkoxy, 1-4C-alkylthio, sulfanyl, hydroxyl, oxo, amino or mono- or di-1-4C-alkylamino,
R8 is halogen, 1-4C-alkyl or 1-4C-alkoxy,
and the enantiomers, as well as the salts, the N-oxides and the salts of the N-oxides of these compounds and enantiomers.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1-7C-Alkyl represents a straight-chain or branched alkyl radical having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl or methyl radicals.

1-4C-Alkylene is a straight chain alkylene radical having 1 to 4 carbon atoms. Examples which may be mentioned in this context are the methylene (—$CH_2$—), ethylene (—$CH_2$—$CH_2$—), trimethylene (—$CH_2$—$CH_2$—$CH_2$—) and the tetramethytene (—$CH_2$—$CH_2$—$CH_2$—$CH_2$—) radical.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radicals.

1-4C-Alkoxy-2-4C-alkoxy represents one of the abovementioned 2-4C-alkoxy radicals, which is substituted by one of the abovementioned 1-4C-alkoxy radicals. Examples which may be mentioned are the 2-methoxyethoxy, the 2-ethoxyethoxy and the 2-isopropoxyethoxy radicals.

3-7C-Cycloalkoxy represents cyclopropyloxy, cyclobutyloxy, cyclopentyloxy, cyclohexyloxy and cycle-heptyloxy, of which cyclopropyloxy, cyclobutyloxy and cyclopentyloxy are preferred.

3-7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1-4C-alkoxy, for example, the 2,2,3,3,3-penta-fluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms of the 1-4C-alkoxy radicals are replaced by fluorine atoms.

As completely or predominantly fluorine-substituted 1-4C-alkyl, for example, the 2,2,3,3,3-pentafluoropropyl, the perfluoroethyl, the 1,2,2-trifluoroethyl, in particular the 1,1,2,2-tetrafluoroethyl, the 2,2,2-trifluoroethyl, the trifluoromethyl and particularly the difluoromethyl radicals may be mentioned. "Predominantly" in this connection means that more than half of the hydrogen atoms of the 1-4C-alkyl radicals are replaced by fluorine atoms.

As completely or partially fluorine-substituted 1-4C-alkyl, for example, the 2,2,3,3,3-pentafluoropropyl, the perfluoroethyl, the 1,2,2-trifluoroethyl, the 1,1,2,2-tetrafluoroethyl, the 2,2,2-trifluoroethyl, the trifluoromethyl, the difluoromethyl and, in particular, the 2,2-difluoroethyl radicals may be mentioned.

1-2C-Alkylenedioxy represents, for example, the methylenedioxy [—O—CH$_2$—O] and the ethylenedioxy [—O—CH$_2$—CH$_2$—O—] radicals.

1-4C-Alkoxy-1-4C-alkyl represents one of the abovementioned 1-4C-alkyl radicals, which is substituted by one of the abovementioned 1-4C-alkoxy radicals. Examples which may be mentioned are the methoxymethyl, the methoxyethyl and the isopropoxyethyl radicals, particularly the 2-methoxyethyl and the 2-isopropoxyethyl radicals.

1-7C-Alkylcarbonyl represents a radical which, in addition to the carbonyl group, contains one of the abovementioned 1-7C-alkyl radicals. Examples which may be mentioned are the acetyl, propionyl, butanoyl and hexanoyl radicals.

Hydroxy-2-4C-alkyl represents 2-4C-alkyl radicals, which are substituted by a hydroxyl group. Examples which may be mentioned are the 2-hydroxyethyl and the 3-hydroxypropyl radicals.

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

Halogen within the meaning of the invention is bromine, chlorine or fluorine.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the isopropoxycarbonyl radicals.

1-4C-Alkylthio represents radicals which, in addition to the sulfur atom, contain one of the abovementioned 1-4C-alkyl radicals. Examples which may be mentioned are the butylthio, propylthio and preferably the ethylthio and methylthio radicals.

Pyridyl includes 2-pyridyl, 3-pyridyl and 4-pyridyl.

The term "oxo" as used herein refers to a doubly carbon-bonded oxygen atom, which form together with the carbon atom to which it is attached a carbonyl or keto group (C=O). An oxo group which is a substituent of a (hetero)aromatic ring results in a replacement of =C(—H)— by —C(=O)— at its binding position. It will be apparent that the introduction of an oxo substituent on an (hetero)aromatic ring de-stroys the (hetero)aromaticity.

When A has the meaning "bond", then the moiety —N(R61)R62 is directly attached to the Har radical.

Har is optionally substituted by R6 and/or R7 and/or R8, and stands for a stabile 5- to 10-membered monocylic or fused bicyclic unsaturated (heteroaromatic) or partially saturated heteroaryl radical comprising 1 to 4 heteroatoms selected independently from the group consisting of oxygen, nitrogen and sulfur.

More precisely, Har is bonded to the tricyclic phenanthridine moiety via a carbon ring atom, whereby all positional isomers are contemplated.

In an embodimental detail (detail 1a) according to this invention, Har is optionally substituted by R6 and/or R7, and is a 9- or 10-membered benzofused bicyclic partially saturated heteroaryl radical corn-prising 1 to 2 heteroatoms selected independently from the group consisting of oxygen, nitrogen and sulfur, in particular in which R6 is 1-4C-alkyl, completely or partially fluorine-substituted 1-4C-alkyl, or halogen, suitably fluorine, R7 is halogen, suitably fluorine.

In a sub-detail of detail 1a according to this invention, Har is optionally substituted by R6 and/or R7, and is a 9- or 10-membered fused bicyclic partially saturated heteroaryl radical comprising a heteroa-tom-free benzene ring and 1 or 2 heteroatoms selected independently from the group consisting of oxygen, nitrogen and sulfur in the other ring, in particular in which R6 is 1-4C-alkyl, completely or partially fluorine-substituted 1-4C-alkyl, or halogen, suitably fluorine, R7 is halogen, suitably fluorine.

Har may include according to this detail 1a, without being restricted thereto, indolinyl, isoindolinyl, tetrahydroquinolinyl, tetrahydroisoquinolinyl, dihydrobenzofuranyl, dihydrobenzothiophenyl, benzo[1,3]dioxolyl, benzodioxanyl (i.e. dihydrobenzo[1,4]dioxinyl), dihydrobenzopyranyl, or dihydro-benzo[1,4]oxazinyl, as well as the R6- and/or R7-substituted derivatives thereof.

Illustratively, as exemplary suitable Har radicals according to detail 1a may be mentioned, for example, without being restricted thereto, benzo[1,4]dioxanyl (i.e. dihydrobenzo[1,4]dioxinyl), benzo[1,3]dioxolyl or 2,2-difluoro-benzo[1,3]dioxolyl.

As more specific exemplary suitable Har radicals according to detail 1a may be mentioned, for example, without being restricted thereto, benzo[1,4]dioxan-6-yl (i.e. dihydrobenzo[1,4]dioxin-6-yl), benzo[1,3]dioxol-5-yl or 2,2-difluoro-benzo[1,3]dioxol-5-yl.

In another embodimental detail (detail 1 b) according to this invention Har is Cyc1, in which
Cyc1 is a partially aromatic group of formula Z

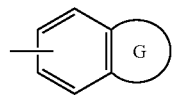

in which
G is optionally substituted by R6 and/or R7, and is a 5- or 6-membered saturated or partially unsaturated heterocyclic ring comprising one or two heteroatoms independently selected from the group consisting of nitrogen, oxygen and sulfur,
whereby said Cyc1 ring system is attached to the parent molecular group via any substitutable carbon atom of the benzene ring,
in which
R6 is 1-4C-alkyl, completely or partially fluorine-substituted 1-4C-alkyl, or halogen such as e.g. fluorine,
R7 is halogen such as e.g. fluorine.

As examples of Cyc1 according to detail 1b may be mentioned, without being restricted thereto, indolinyl, isoindolinyl, tetrahydroquinolinyl, tetrahydroisoquinolinyl, 2,3-dihydrobenzofuranyl, 2,3-dihydrobenzothiophenyl, benzo[1,3]dioxolyl, dihydrobenzo[1,4]dioxinyl, chromanyl, chromenyl, or dihydrobenzo[1,4]oxazinyl, or 2,2-difluorobenzo[1,3]dioxolyl, or 4-methyl-3,4-dihydrobenzo[1,4]oxazinyl.

In yet another embodimental detail (detail 1c) according to this invention Har is Cyc1, in which Cyc1 is optionally substituted by halogen, particularly chlorine, on its benzene ring, and is indolinyl, isoindolinyl, tetrahydroquinolinyl, tetrahydroisoquinolinyl, or 3,4-dihydrobenzo[1,4]oxazinyl, or, particularly,
1-methyl-indolinyl, 2-methyl-isoindolinyl, 1-methyl-tetrahydroquinolinyl, 2-methyl-tetrahydroisoquinolinyl, or 4-methyl-3,4-dihydrobenzo[1,4]oxazinyl,
2,3-dihydrobenzofuranyl, 2,3-dihydrobenzothiophenyl, benzo[1,3]dioxolyl, dihydrobenzo[1,4]dioxinyl, chromanyl, chromenyl, or 2,2-difluoro-benzo[1,3]dioxolyl,
whereby said Cyc1 ring system is attached to the parent molecular group via any substitutable carbon atom of the benzene ring;
such as e.g. benzo[1,3]dioxol-5-yl, dihydrobenzo[1,4]dioxin-5-yl, 2,2-difluoro-benzo[1,3]dioxol-5-yl, or 5-chloro-4-methyl-3,4-dihydrobenzo[1,4]oxazin-7-yl.

In a further embodimental detail (detail 2a) according to this invention, Har is optionally substituted by R6, and is a 9- or 10-membered fused bicyclic unsaturated (heteroaromatic) heteroaryl radical comprising 1 to 4 heteroatoms independently selected from the group consisting of oxygen, nitrogen and sulfur,
in particular in which
R6 is 1-4C-alkyl, or completely or partially fluorine-substituted 1-4C-alkyl.

In a sub-detail of detail 2a according to this invention, Har is optionally substituted by R6, and is a 9- or 10-membered fused bicyclic unsaturated (heteroaromatic) heteroaryl radical comprising a heteroa-tom-free benzene ring and 1 to 3 heteroatoms independently selected from the group consisting of oxygen, nitrogen and sulfur in the other ring,
in particular in which
R6 is 1-4C-alkyl, or completely or partially fluorine-substituted 1-4C-alkyl.

Har may include according to this detail 2a, without being restricted thereto, the stabile benzo-fused derivatives of the Har radicals mentioned in detail 3a or 3b below, such as e.g. benzothiophenyl, benzofuranyl, indolyl, benzoxazolyl, benzothiazolyl, indazolyl, benzimidazolyl, benzisoxazolyl, benzisothi-azolyl, benzofurazanyl, benzotriazolyl, benzothiadiazolyl, quinolinyl, isoquinolinyl, quinazolinyl, quinoxalinyl, phthalazinyl or cinnolinyl; or indolizinyl, purinyl, naphthyridinyl or pteridinyl; as well as the R6-substituted derivatives thereof.

Illustratively, as exemplary suitable Har radicals according to detail 2a may be mentioned, for example, without being restricted thereto, quinolinyl, benzofurazanyl or benzothiazolyl.

As more specific exemplary suitable. Har radicals according to detail 2a may be mentioned, for example, without being restricted thereto, quinolin-6-yl, benzofurazanyl-5-yl or benzothiazol-6-yl.

In another further embodimental detail (detail 2b) according to this invention Har is Cyc2, in which Cyc2 is optionally substituted by R6 and/or R7 and/or R8, and is a 9- or 10-membered fused bicyclic fully aromatic ring system containing one to four heteroatoms each of which is selected from nitrogen, oxygen and sulphur, and which Cyc2 ring system is made up of
a first constituent (constituent m) being a benzene ring, or a 6-membered monocyclic heteroaryl ring comprising one or two nitrogen atoms (such as e.g. pyridine),
and fused to said first constituent m,
a second constituent (constituent n) being a 5- or 6-membered monocytic heteroaryl ring comprising one to three heteroatoms independently selected from the group consisting of nitrogen, oxygen and sulphur.

In a particular embodiment, said Cyc2 ring system is attached to the parent molecular group via any substitutable ring carbon atom of the constituent m.

In another embodiment, said Cyc2 ring system may be attached to the parent molecular group via any substitutable ring carbon atom of the constituent n.

Har may include according to this detail 2b, without being restricted thereto, the stabile benzo- or pyrido-fused derivatives of the Har radicals mentioned in detail 3a or 3b below, such as e.g. the benzo-fused radicals benzothiophenyl, benzofuranyl, indolyl, benzoxazolyl, benzothiazolyl, indazolyl, benzimidazolyl, benzisoxazolyl, benzisothiazolyl, benzofurazanyl, benzotriazolyl, benzothiadiazolyl, quinolinyl, isoquinolinyl, quinazolinyl, quinoxalinyl, phthalazinyl, cinnolinyl, isoindolyl, isofuranyl or isobenzothiophenyl, or the pyrido-fused radicals pyrazolopyridinyl (such as e.g. pyrazolo[3,4-b]pyridinyl), pyrrolopyridinyl or imidazopyridinyl; as well as indolizinyl, purinyl, naphthyridinyl or pteridinyl; and the R6- and/or R7- and/or R8-substituted derivatives thereof, in which R6, R7 and R8 have the meanings as indicated in the description of this invention.

In more detailed example, Har may include according to this detail 2b, without being restricted thereto, quinolinyl, benzofurazanyl, benzothiazolyl, benzotriazolyl or pyrazolopyridinyl (such as e.g. pyre-zolo[3,4-b]pyridinyl); as well as the R6- and/or R7- and/or R8-substituted derivatives thereof, such as e.g. 1-(1-4C-alkyl)-1H-benzotriazolyl or 1-(1-4C-alkyl)-4-methoxy-3-methyl-1H-pyrazolo[3,4-b]pyridinyl.

Also in more detailed example, Har may include according to this detail 2b, without being restricted thereto, benzothiazolyl, benzoxazolyl, benzimidazolyl, indazolyl, 1H-methyl-benzimidazolyl, or 1-methyl-indazolyl, whereby these radicals may be attached to the parent molecular group via the benzene ring.

Also in more detailed example, Har may include according to this detail 2b, without being restricted thereto, benzoxadiazolyl (e.g. benzofurazanyl), benzotriazolyl, 1H-methyl-benzotriazolyl or benzothiadiazolyl (e.g. benzo[1,2,3]thiadiazolyl), whereby these radicals may be attached to the parent molecular group via the benzene ring.

Also in more detailed example, Har may include according to this detail 2b, without being restricted thereto, quinolinyl, isoquinolinyl, quinoxalinyl, quinazolinyl or cinnolinyl, whereby these radicals may be attached to the parent molecular group via the benzene ring.

Illustratively, as exemplary suitable Har radicals according to detail 2b may be mentioned, for example, without being restricted thereto, quinolinyl, benzofurazanyl, benzothiazolyl, 1-(1-4C-alkyl)-1H-benzotriazolyl or 1-(1-4C-alkyl)-4-methoxy-3-methyl-1H-pyrazolo[3,4-b]pyridinyl, as well as benzo[1,2,3]thiadiazolyl and quinoxalinyl.

As more specific exemplary suitable Har radicals according to detail 2b may be mentioned, for example, without being restricted thereto, quinolin-6-yl, benzofurazan-5-yl, benzothiazol-6-yl, 1-methyl-1H-benzotriazol-5-yl or 4-methoxy-1,3-dimethyl-1H-pyrazolo[3,4-b]pyridin-5-yl, as well as benzo[1,2,3]thiadiazol-5-yl and quinoxalin-5-yl.

In a yet further embodimental detail (detail 3a) according to this invention, Har is optionally substituted by R6 and/or R7 and/or R8, and is a 5- or 6-membered monocyclic unsaturated (heteroaromatic) heteroaryl radical comprising 1 to 4 heteroatoms selected independently from the group consisting of oxygen, nitrogen and sulfur,
in which
R6 is halogen, 1-4C-alkyl, 1-4C-alkoxy, 1-4C-alkoxy-2-4C-alkoxy, 1-4C-alkylthio, cyano, 1-4C-alkoxycarbonyl, carboxyl, hydroxyl, -A-N(R61)R62, pyridyl, or completely or partially fluorine-substituted 1-4C-alkyl, in which
A is a bond or 1-4C-alkylene,
R61 is hydrogen or 1-4C-alkyl,
R62 is hydrogen or 1-4C-alkyl,
or R61 and R62 together and with inclusion of the nitrogen atom, to which they are attached, form a heterocyclic ring Het1, in which
Het1 is optionally substituted by R611, and is a 3- to 7-membered saturated or unsaturated monocyclic heterocyclic ring radical comprising the nitrogen atom, to which R61 and R62 are bonded, and optionally one to three further heteroatoms independently selected from the group consisting of oxygen, nitrogen and sulfur, in which
R611 is 1-4C-alkyl,
R7 is 1-4C-alkoxy, 1-4C-alkoxy-2-4C-alkoxy, 1-4C-alkylthio, hydroxyl, amino or mono- or di-1-4C-alkylamino,
R8 is halogen.

In another yet further embodimental detail (detail 3b) according to this invention, Har is optionally substituted by R6 and/or R7 and/or R8, and is a 5- or 6-membered monocyclic unsaturated (fully aromatic) heteroaryl radical comprising 1 to 4 heteroatoms selected independently from the group consisting of oxygen, nitrogen and sulphur, in which R6, R7 and R8 have the meanings as indicated in the description of this invention.

More precisely, in one embodiment of detail 3a or 3b according to this invention, Har is optionally substituted by R6 and/or R7 and/or R8, and is a 6-membered monocyclic unsaturated (heteroaromatic) heteroaryl radical comprising 1 to 3, particularly 1 or 2, nitrogen atoms.

In addition, in another embodiment of detail 3a or 3b, Har is optionally substituted by R6 and/or R7, and is a 5-membered monocyclic unsaturated (heteroaromatic) heteroaryl radical comprising 1 to 4 heteroatoms selected independently from the group consisting of oxygen, nitrogen and sulfur.

Har may include according to detail 3a or 3b, without being restricted thereto, furanyl, thiophenyl, pyrrolyl, oxazolyl, isoxazolyl, thiazolyl, isothiazolyl, imidazolyl, pyrazolyl, triazolyl (precisely: 1,2,4-triazolyl or 1,2,3-triazolyl), thiadiazolyl (precisely: 1,3,4-thiadiazolyl, 1,2,5-thiadiazolyl, 1,2,3-thiadiazolyl or 1,2,4-thiadiazolyl), oxadiazolyl (precisely: 1,3,4-oxadiazolyl, 1,2,5-oxadiazolyl, 1,2,3-oxadiazolyl or 1,2,4-oxadiazolyl) or tetrazolyl; or pyridinyl, pyrimidinyl, pyrazinyl or pyridazinyl; as well as the R6- and/or R7- and/or R8-substituted derivatives thereof.

In more detailed example, Har radicals according to detail 3a or 3b may include, without being restricted thereto, isoxazolyl, imidazolyl, thiazolyl, oxazolyl, as well as the R6- and/or R7-substituted derivatives thereof, or pyridinyl, pyrimidinyl, pyrazinyl or pyridazinyl, as well as the R6- and/or R7- and/or R8-substituted derivatives thereof.

In still more detailed example, Har radicals according to detail 3a may include, without being restricted thereto, pyridinyl, isoxazolyl, imidazolyl, thiazolyl, oxazolyl, pyrimidinyl, pyrazinyl or pyridazinyl, as well as the R6- and/or R7-substituted derivatives thereof, wherein
R6 is 1-4C-alkyl, 1-4C-alkoxy, pyridyl or morpholin-4-yl,
R7 is 1-4C-alkoxy.

In yet still more detailed embodimental example, Har radicals according to detail 3a may include, without being restricted thereto, isoxazolyl; N-(1-4C-alkyl)-imidazolyl; thiazolyl optionally substituted by pyridyl; or pyridinyl, pyrimidinyl, pyridazinyl, pyrazinyl, each of which is optionally substituted by R6- and/or R7 in which
R6 is 1-4C-alkoxy, mono- or di-1-4C-alkylamino, pyrazol-1-yl, imidazol-1-yl, triazol-1-yl or morpholin-4-yl,
R7 is 1-4C-alkoxy or mono- or di-1-4C-alkylamino,
such as, for example, 6-(morpholin-4-yl)-pyridin-3-yl, pyridin-3-yl, pyridin-4-yl, 1-methyl-imidazol-2-yl, 2,6-dimethoxy-pyridin-4-yl, 2,6-dimethoxy-pyridin-3-yl, 3,6-dimethoxy-pyridazin-4-yl, 2,6-dimethoxy-pyrimidin-4-yl, 2,6-bis-dimethylamino-pyrimidin-4-yl, pyrimidin-5-yl, pyrazin-2-yl, 6-(pyrazol-1-yl)-pyridin-3-yl, 6-(imidazol-1-yl)-pyridin-3-yl or 6-([1,2,4]triazol-1-yl)-pyridin-3-yl.

Illustratively, as exemplary suitable Har radicals according to detail 3a may be mentioned, for example, without being restricted thereto, isoxazolyl; N-(1-4C-alkyl)-imidazolyl; thiazolyl optionally substituted by pyridyl; or pyridinyl optionally substituted by R6- and/or R7 in which
R6 is 1-4C-alkoxy or morpholin-4-yl,
R7 is 1-4C-alkoxy.

As more specific exemplary suitable Har radicals according to detail 3a may be mentioned, for example, without being restricted thereto, 6-(morpholin-4-yl)-pyridin-3-yl, pyridin-3-yl, pyridin-4-yl, isoxazol-5-yl, 1-methyl-imidazol-2-yl, 1-methyl-imidazol-5-yl, 2-(pyridin-3-yl)-thiazol-4-yl, or, in particular, 2,6-dimethoxy-pyridin-4-yl or, in more particular, 2,6-dimethoxy-pyridin-3-yl.

In still more detailed example, Har radicals according to detail 3b may include, without being restricted thereto, pyridinyl, isoxazolyl, imidazolyl, thiazolyl, oxazolyl, pyrimidinyl, pyrazinyl or pyridazinyl, as well as the R6- and/or R7- and/or R8-substituted derivatives thereof, wherein
R6 is 1-4C-alkyl, 1-4C-alkoxy, 1-4C-alkoxycarbonyl, carboxyl, pyridyl, piperidin-1-yl, morpholin-4-yl, pyrazol-1-yl or imidazol-1-yl,
R7 is 1-4C-alkoxy,
R8 is halogen or 1-4C-alkoxy.

In yet still More detailed embodimental example, Har radicals according to detail 3b may include, without being restricted thereto, isoxazolyl; N-(1-4C-alkyl)-imidazolyl;
thiazolyl optionally substituted by pyridyl;
pyridinyl, pyrimidinyl, pyridazinyl, pyrazinyl, each of which is optionally substituted by R6 and/or R7 and/or R8 in which
R6 is 1-4C-alkyl, 1-4C-alkoxy, pyrazol-1-yl, imidazol-1-yl, piperidin-1-yl or morpholin-4-yl,
R7 is 1-4C-alkoxy,
R8 is 1-4C-alkoxy or halogen; or
pyridinyl, which is optionally substituted by R6 and/or R7 and/or R8 in which
R6 is 1-4C-alkoxy, pyrazol-1-yl, imidazol-1-yl, piperidin-1-yl, morpholin-4-yl, 1-4C-alkoxycarbonyl or carboxyl,
R7 is 1-4C-alkoxy,
R8 is 1-4C-alkoxy or halogen.

As exemplary suitable Har radicals according to detail 3b may be mentioned, for example, without being restricted thereto, pyridinyl, isoxazolyl, imidazolyl, thiazolyl, oxazolyl, pyrimidinyl, pyrazinyl or pyridazinyl, each of which is optionally substituted by R6, in which
R6 is 1-4C-alkyl or pyridyl.

Yet as exemplary suitable Har radicals according to detail 3b may be mentioned, for example, without being restricted thereto, pyridinyl, pyrimidinyl, pyrazinyl or pyridazinyl, each of which is optionally substituted by R6 and/or R7 and/or R8, in which
R6 is 1-4C-alkoxy,
R7 is 1-4C-alkoxy,
R8 is 1-4C-alkoxy.

Yet as exemplary suitable Har radicals according to detail 3b may be mentioned, for example, without being restricted thereto, pyridinyl, which is substituted by R6 and/or R7, in which
R6 is 1-4C-alkoxy,
R7 is 1-4C-alkoxy.

Yet as exemplary suitable liar radicals according to detail 3b may be mentioned, for example, without being restricted thereto, pyridinyl, which is substituted by R6 and/or R7 and R8, in which
R6 is 1-4C-alkoxy,
R7 is 1-4C-alkoxy,
R8 is 1-4C-alkoxy or chlorine.

Yet as exemplary suitable Har radicals according to detail 3b may be mentioned, for example, without Wing restricted thereto, pyrimidinyl, which is by R6 and/or R7 and/or R8, in which
R6 is 1-4C-alkoxy,
R7 is 1-4C-alkoxy,
R8 is 1-4C-alkoxy.

Yet as exemplary suitable Har radicals according to detail 3b may be mentioned, for example, without being restricted thereto, pyridinyl, which is substituted by R6, in which
R6 is 1-4C-alkoxycarbonyl or carboxyl.

Yet as exemplary suitable Har radicals according to detail 3b may be mentioned, for example, without being restricted thereto, pyridinyl, which is substituted by R6, in which
R6 is morpholin-4-yl, piperidin-1-yl, pyrazol-1-yl or imidazol-1-yl.

As more specific exemplary suitable Har radicals according to detail 3b may be mentioned, for example, without being restricted thereto, pyridin-3-yl, pyridin-4-yl, pyrimidin-5-yl, pyrazin-2-yl, 5-methyl-pyrazin-2-yl, isoxazol-5-yl, 1-methyl-imidazol-2-yl, 1-methyl-imidazol-5-yl, 2-(pyridin-3-yl)-thiazol-4-yl, 2,6-dimethoxy-pyridin-4-yl, 2,6-dimethoxy-pyridin-3-yl, 2-methoxy-pyridin-3-yl, 6-(methoxycarbonyl)-pyridin-3-yl, 5-(methoxycarbonyl)-pyridin-2-yl, 2,6-dimethoxypyrimidin-4-yl, 2-methoxy-pyrimidin-5-yl, 2,4,6-trimethoxy-pyrimidin-5-yl, 2,4-dimethoxy-pyrimidin-5-yl, 2,6-dimethoxy-pyrimidin-4-yl, 6-(morpholin-4-yl)-pyridin-3-yl, 6-(piperidin-1-yl)-pyridin-3-yl, 6-(pyrazol-1-yl)-pyridin-3-yl, 6-(imidazol-1-yl)-pyridin-3-yl, or 3-chloro-2,6-dimethoxy-pyridin-4-yl.

In still more detailed example, Har radicals according to detail 3b may also include, without being restricted thereto, pyridinyl, isoxazolyl, imidazolyl, thiazolyl, oxazolyl, pyrimidinyl, pyrazinyl or pyridazinyl, as well as the R6- and/or R7- and/or R8-substituted derivatives thereof, wherein
R6 is halogen, 1-4C-alkyl, 1-4C-alkoxy, 1-4C-alkylthio, 1-4C-alkoxycarbonyl, carboxyl, hydroxyl, oxo, pyridyl or -A-N(R61)R62, in which
A is a bond or 1-4C-alkylene,
R61 is 1-4C-alkyl,
R62 is 1-4C-alkyl,
or R61 and R62 together and with inclusion of the nitrogen atom, to which they are attached, form a heterocyclic ring Het1, in which
either
Het1 is piperidin-1-yl, pyrrolidin-1-yl, morpholin-4-yl, thiomorpholin-4-yl, piperazin-1-yl or 4N-methyl-piperazin-1-yl,
or
Het1 is pyrrol-1-yl, pyrazol-1-yl, triazol-1-yl or imidazol-1-yl,
R7 is 1-4C-alkyl, 1-4C-alkoxy, 1-4C-alkylthio, hydroxyl, oxo, or di-1-4C-alkylamino,
R8 is halogen, 1-4C-alkyl or 1-4C-alkoxy.

In yet still more detailed embodimental example, Har radicals according to detail 3b may also include, without being restricted thereto, isoxazolyl, N-(1-4C-alkyl)-imidazolyl, and thiazolyl optionally substituted by pyridyl.

In yet still more detailed embodimental example, Har radicals according to detail 3b may also include, without being restricted thereto,
pyridinyl, pyrimidinyl, pyridazinyl, pyrazinyl, each of which is optionally substituted by R6 and/or R7 and/or R8 in which
R6 is halogen, 1-4C-alkyl, 1-4C-alkoxy, 1-4C-alkylthio, 1-4C-alkoxycarbonyl, carboxyl, hydroxyl, oxo, pyridyl or -A-N(R61)R62, in which
A is a bond or 1-2C-alkylene,
R61 is 1-4C-alkyl,
R62 is 1-4C-alkyl,
or R61 and R62 together and with inclusion of the nitrogen atom, to which they are attached, form a heterocyclic ring Het1, in which
either
Het1 is piperidin-1-yl, pyrrolidin-1-yl or morpholin-4-yl,
or
Het1 is pyrazol-1-yl or imidazol-1-yl,
R7 is 1-4C-alkyl, 1-4C-alkoxy, 1-4C-alkylthio, hydroxyl, oxo, or di-1-4C-alkylamino,
R8 is halogen or 1-4C-alkoxy.

As exemplary suitable Har radicals according to detail 3b may be also mentioned, for example, without being restricted thereto, pyridinyl, pyrimidinyl, pyrazinyl or pyridazinyl, each of which is substituted by R6, in which
R6 is 1-4C-alkyl, 1-4C-alkoxy, 1-4C-alkylthio, 1-4C-alkoxycarbonyl, carboxyl, hydroxyl, or -A-N(R61)R62, in which
A is a bond, or 1-2C-alkylene,
R61 is 1-4C-alkyl,
R62 is 1-4C-alkyl,
or R61 and R62 together and with inclusion of the nitrogen atom, to which they are attached, form a heterocyclic ring Het1, in which either
Het1 is piperidin-1-yl, pyrrolidin-1-yl or morpholin-4-yl,
or
Het1 is pyrazol-1-yl or imidazol-1-yl.

As exemplary suitable Har radicals according to detail 3b may be also mentioned, for example, without being restricted thereto,
either
pyridinyl, pyrimidinyl, pyrazinyl or pyridazinyl, each of which is substituted by R6 and R7, in which
R6 is halogen, 1-4C-alkoxy, 1-4C-alkylthio, oxo, or -A-N(R61)R62, in which
A is a bond,
R61 is 1-4C-alkyl,
R62 is 1-4C-alkyl, and
R7 is 1-4C-alkyl, 1-4C-alkoxy, 1-4C-alkylthio, or di-1-4C-alkylamino,
or
pyridinyl, pyrimidinyl, pyrazinyl or pyridazinyl, each of which is substituted by R6 and R8, in which
R6 is -A-N(R61)R62, in which
A is a bond,
R61 is 1-4C-alkyl,
R62 is 1-4C-alkyl, and
R8 is halogen.

As exemplary suitable Har radicals according to detail 3b may be also mentioned, for example, without being restricted thereto,
pyridinyl, pyrimidinyl, pyrazinyl or pyridazinyl, each of which is substituted by R6 and R7 and R8, in which
R6 is 1-4C-alkoxy, or di-1-4C-alkylamino,
R7 is 1-4C-alkoxy, or di-1-4C-alkylamino,
R8 is halogen or 1-4C-alkoxy, As exemplary suitable Har radicals according to detail 3b may be also mentioned, for example, without being restricted thereto, pyridinyl, pyrimidinyl, pyrazinyl or pyridazinyl, each of which is unsubstituted.

As more detailed exemplary suitable Har radicals according to detail 3b may be mentioned, for example, without being restricted thereto, pyridinyl which is substituted by R6, in which
R6 is 1-4C-alkoxy particularly 1-2C-alkoxy, 1-4C-alkylthio particularly 1-2C-alkylthio, 1-4C-alkoxycarbonyl particularly 1-2C-alkoxycarbonyl, carboxyl, hydroxyl, or -A-N(R61)R62, in which
A is a bond,
R61 is 1-4C-alkyl, particularly 1-2C-alkyl,
R62 is 1-4C-alkyl, particularly 1-2C-alkyl.

Yet as more detailed exemplary suitable Har radicals according to detail 3b may be mentioned, for example, without being restricted thereto, pyridinyl which is substituted by R6, in which
R6 is -A-N(R61)R62, in which
A is a bond, or 1-2C-alkylene, particularly ethylene,
R61 and R62 together and with inclusion of the nitrogen atom, to which they are attached, form a heterocyclic ring Het1, in which
Het1 is piperidin-1-yl, pyrrolidin-1-yl or morpholin-4-yl.

Yet as more detailed exemplary suitable Har radicals according to detail 3b may be mentioned, for example, without being restricted thereto, pyridinyl which is substituted by R6, in which
R6 is -A-N(R61)R62, in which
A is a bond,
R61 and R62 together and with inclusion of the nitrogen atom, to which they are attached, form a heterocyclic ring Het1, in which
Het1 is pyrrol-1-yl, triazol-1-yl, or, particularly, pyrazol-1-yl or imidazol-1-yl.

Further, as more detailed exemplary suitable Har radicals according to detail 3b may be mentioned, for example, without being restricted thereto, pyrimidinyl which is substituted by R6, in which
R6 is 1-4C-alkoxy, 1-4C-alkylthio, or -A-N(R61)R62, in which
A is a bond,
R61 is 1-4C-alkyl,
R62 is 1-4C-alkyl.

Further, as more detailed exemplary suitable Har radicals according to detail 3b may be mentioned, for example, without being restricted thereto,
either
pyridinyl, pyrimidinyl, pyrazinyl or pyridazinyl, each of which is substituted by R6 and R7 in which
R6 is 1-4C-alkoxy, and
R7 is 1-4C-alkoxy,
or
R6 is oxo, and
R7 is 1-4C-alkyl,
or
R6 is 1-4C-alkylthio, and
R7 is 1-4C-alkyl,
or
R6 is halogen, and
R7 is 1-4C-alkylthio,
or
R6 is di-1-4C-alkylamino, and
R7 is 1-4C-alkoxy,
or
R6 is di-1-4C-alkylamino, and
R7 is di-1-4C-alkylamino;
or
pyridinyl, pyrimidinyl, pyrazinyl or pyridazinyl, each of which is substituted by R6 and R8, in which
R6 is di-1-4C-alkylamino, and
R8 is halogen.

Further, as more detailed exemplary suitable Har radicals according to detail 3b may be mentioned, for example, without being restricted thereto, pyridinyl, which is substituted by R6 and R7 in which
R6 is 1-4C-alkoxy, particularly 1-2C-alkoxy, and
R7 is 1-4C-alkoxy, particularly 1-2C-alkoxy, Yet as more detailed exemplary suitable Har radicals according to detail 3b may be mentioned, for example, without being restricted thereto, pyridinyl, which is substituted by R6 and R7 in which
R6 is oxo, and
R7 is 1-4C-alkyl, particularly 1-2C-alkyl,
such as, for example, N-(1-4C-alkyl)-pyridonyl, e.g. N-(1-2C-alkyl)-pyrid-2-onyl.

Further, as more detailed exemplary suitable Har radicals according to detail 3b may be mentioned, for example, without being restricted thereto,
either
pyrimidinyl, which is substituted by R6 and R7 in which
R6 is 1-4C-alkoxy, particularly 1-2C-alkoxy, and
R7 is 1-4C-alkoxy, particularly 1-2C-alkoxy,
or
R6 is oxo, and
R7 is 1-4C-alkyl, particularly 1-2C-alkyl,
or
R6 is 1-4C-alkylthio, particularly 1-2C-alkylthio, and
R7 is 1-4C-alkyl, particularly 1-2C-alkyl,
or
R6 is halogen, particularly chlorine, and
R7 is 1-4C-alkylthio, particularly 1-2C-alkylthio, or
R6 is di-1-4C-alkylamino, particularly di-1-2C-alkylamino, and
R7 is 1-4C-alkoxy, particularly 1-2C-alkoxy,
or
R6 is di-1-4C-alkylamino, particularly di-1-2C-alkylamino, and
R7 is di-1-4C-alkylamino, particularly di-1-2C-alkylamino;
or
pyrimidinyl, which is substituted by R6 and R8, in which
R6 is di-1-4C-alkylamino, particularly di-1-2C-alkylamino, and
R8 is halogen, particularly chlorine.

Further, as more detailed exemplary suitable Har radicals according to detail 3b may be mentioned, for example, without being restricted thereto, pyridazinyl, which is substituted by R6 and R7 in which
R6 is 1-4C-alkoxy, particularly 1-2C-alkoxy, and
R7 is 1-4C-alkoxy, particularly 1-2C-alkoxy.

Further, as more detailed exemplary suitable Har radicals according to detail 3b may be mentioned, for example, without being restricted thereto, pyridin-3-yl, pyridin-4-yl, or pyrazin-2-yl, each of which is unsubstituted.

Yet as more detailed exemplary suitable Har radicals according to detail 3b may be mentioned, for example, without being restricted thereto, pyrimidin-5-yl, which is unsubstituted.

Het1 is optionally substituted by R611 and stands for a stabile monocylic 3- to 7-membered fully saturated or unsaturated (heteroaromatic) heterocyclic ring radical comprising the nitrogen atom, to which R61 and R62 are bonded, and optionally one to three further heteroatoms independently selected from the group consisting of nitrogen, oxygen and sulfur.

In a first facet (facet 1) according to this invention, Het1 is optionally substituted by R611 on a ring nitrogen atom and stands for a stabile monocylic 3- to 7-membered fully saturated heterocyclic ring radical comprising the nitrogen atom, to which R61 and R62 are bonded, and optionally one further heteroatom selected from the group consisting of nitrogen, oxygen and sulfur.

In a second facet (facet 2) according to this invention, Het1 stands for a stabile monocylic 5-membered unsaturated (heteroaromatic) ring radical comprising the nitrogen atom, to which R61 and R62 are bonded, and optionally one to three further nitrogen atoms.

Het1 may include according to facet 1, without being restricted thereto, aziridinyl, azetidinyl, pyrrolid-inyl, piperidinyl, homopiperidinyl, morpholinyl, thiomorpholinyl, oxazolidinyl, isoxazolidinyl, thiazolid-inyl, isothiazolidinyl, pyrazolidinyl, imidazolidinyl, piperazinyl or homopiperazinyl.

Het1 may also include according to facet 2, without being restricted thereto, pyrrolyl, imidazolyl, pyrazolyl, triazolyl or tetrazolyl.

As further examples for Het1 according to this invention may be mentioned, without being restricted thereto, R611-substituted derivatives of the abovementioned exemplary Het1 radicals according to facet 1, such as e.g. 4-N—(R611)-piperazinyl or 4-N—(R611)-homopiperazinyl.

Illustratively, as exemplary suitable Het1 radicals according to facet 1 may be mentioned, for example, without being restricted thereto, morpholin-4-yl, or piperidin-1-yl.

Illustratively, as exemplary suitable Het1 radicals according to facet 2 may be mentioned, for example, without being restricted thereto, pyrazol-1-yl, or imidazol-1-yl.

In general, unless otherwise mentioned, the heterocyclic groups mentioned herein refer to all of the possible isomeric forms thereof.

The heterocyclic groups mentioned herein refer, unless otherwise noted, in particular to all of the possible positional isomers thereof.

Thus, for example, the term pyridyl or pyridinyl includes pyridin-2-yl, pyridin-3-yl and pyridin-4-yl.

The heterocyclic groups mentioned herein refer, unless otherwise noted, yet in particular to all of the possible tautomers, e.g. the keto/enol tautomers, thereof, in pure form as well as any mixtures thereof.

Thus, for example, pyridine compounds which are substituted by a hydroxyl or an oxo group in the 2- or 4-position of the pyridine ring can exist in different tautomeric forms, i.e. the enol and the keto form, which are both contemplated by the present invention in pure form as well as in any mixtures thereof.

Constituents which are optionally substituted as stated herein, may be substituted, unless otherwise noted, at any possible position.

The heterocyclic groups, alone or as part of other groups, mentioned herein may be substituted by their given substituents, unless otherwise noted, at any possible position, such as e.g. at any substitutable ring carbon or ring nitrogen atom.

Unless otherwise noted, rings containing quaternizable imino-type ring nitrogen atoms (—N=) may be preferably not quaternized on these imino-type ring nitrogen atoms by the mentioned substituents; this may not apply to compounds according to this invention which can escape from this quatemization by keto/enol tautomerism.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent. As it is known for the person skilled in the art, compounds comprising nitrogen atoms can be form N-oxides. Particularly, imine nitrogen, especially heterocyclic or heteroaromatic imine nitrogen, or pyri-dine-type nitrogen (=N—) atoms, can be N-oxidized to form the N-oxides comprising the group =$N^+(O^-)$—. Thus, the compounds according to the present invention comprising the imine nitrogen atom in position 5 of the phenylphenanthridine backbone and, optionally (depending on the meaning of the substituents), one or more further nitrogen atoms suitable to exist in the N-oxide state (=$N^+(O^-)$—) may be capable to form (depending on the number of nitrogen atoms suitable to form stabile N-oxides) mono-N-oxides, bis-N-oxides or multi-N-oxides, or mixtures thereof.

The term N-oxide(s) as used in this invention therefore encompasses all possible, and in particular all stabile, N-oxide forms, such as mono-N-oxides, bis-N-oxides or multi-N-oxides, or mixtures thereof in any mixing ratio.

Possible salts for compounds of the formula I-depending on substitution—are all acid addition salts or all salts with bases. Particular mention may be made of the pharmacologically tolerable salts of the inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, it being possible to employ the acids in salt preparation—depending on whether a mono- or polybasic acid is con-cerned and depending on which salt is desired—in an equimolar quantitative ratio or one differing therefrom.

In the context of the foregoing, as further acids, which may be used in the preparation of possible salts of compounds of formula I, can be mentioned adipic acid, L-ascorbic acid, L-aspartic acid, ben-zenesulfonic acid, 4-acetamido-benzoic acid, (+)-camphoric acid, (+)-camphor-10-sulfonic acid, caprylic acid (octanoic acid), dodecylsulfuric acid, ethane-1,2-disulfonic acid, ethanesulfonic acid, 2-hydroxy-ethane-sulfonic acid, formic acid, galactaric acid, gentisic acid, D-glucoheptonic acid, D-glucuronic acid, glutamic acid, 2-oxo-glutaric acid, hippuric acid, lactic acid, malonic acid, mandelic acid, naphthalene-1,5-disulfonic acid, naphthalene-2-sulfonic acid, nicotinic acid, palmitic acid, pamoic acid (embonic acid), and pyroglutamic acid.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can initially be obtained, for example, as process products in the preparation of the compounds according to the invention on an industrial scale are converted into pharmacologically tolerable salts by processes known to the person skilled in the art.

It is known to the person skilled in the art that the compounds according to the invention and their salts, when they are isolated, for example, in crystalline form, can contain various amounts of solvents. The invention therefore also comprises all solvates and in particular all hydrates of the compounds of the formula I, and also all solvates and in particular all hydrates of the salts of the compounds of the formula I.

Furthermore, the invention includes all conceivable tautomeric forms of the compounds of the present invention in pure form as well as any mixtures thereof. In this connection, the person skilled in the art knows that enolizable keto groups can exist, depending on the individual chemical surrounding, in their tautomeric enol forms, and vice versa. As it is art-known hereby, keto and enol functions can mu-tually exchange in equilibrium. The invention includes in this context both the stable keto and the stable enol isomers of the compounds according to this invention in pure form, as well as the mixtures thereof, in any mixing ratio.

Compounds of formula I according to aspect A more worthy to be mentioned in a sub-aspect (subaspect A1) are those, in which
R1 is 1-2C-alkoxy, 3-5C-cycloalkoxy, 3-5C-cycloalkyl-methoxy, 2,2-difluoroethoxy, or completely or predominantly fluorine-substituted 1-2C-alkoxy,
R2 is 1-2C-alkoxy, 3-5C-cycloalkoxy, 3-5C-cycloalkyl-methoxy, 2,2-difluoroethoxy, or completely or predominantly fluorine-substituted 1-2C-alkoxy,
R3 is hydrogen,
R31 is hydrogen;
either, in a first embodiment (embodiment a) according to the present invention,
R4 is —O—R41, in which
R41 is hydrogen or 1-4C-alkylcarbonyl, and
R5 is hydrogen,
or, in a second embodiment (embodiment b) according to the present invention,
R4 is hydrogen, and
R5 is —O—R51, in which
R51 is hydrogen or 1-4C-alkylcarbonyl;
in one embodimental detail according to this invention,
Har is Cyc1, in which
Cyc1 is a group of formula Z

in which
G is optionally substituted by R6 and/or R7, and is a 5- or 6-membered saturated or partially unsaturated heterocyclic ring comprising one or two heteroatoms independently selected from the group consisting of nitrogen, oxygen and sulfur,
whereby said Cyc1 ring system is attached to the parent molecular group via any substitutable carbon atom of the benzene ring,
in which
R6 is 1-2C-alkyl or halogen, such as e.g. fluorine,
R7 is halogen, such as e.g. fluorine;
or, in another embodimental detail according to this invention,
Har is Cyc2, in which
Cyc2 is optionally substituted by R6 and/or R7 and/or R8, and is a 9- or 10-membered fused bicyclic fully aromatic ring system containing one to four heteroatoms each of which is selected from nitrogen, oxygen and sulphur, and which Cyc2 ring system is made up of
a first constituent (constituent m) being a benzene ring, or a 6-membered monocyclic heteroaryl ring comprising one or two nitrogen atoms,
and fused to said first constituent m,
a second constituent (constituent n) being a 5- or 6-membered monocytic heteroaryl ring comprising one to three heteroatoms independently selected from the group consisting of nitrogen, oxygen and sulphur,
whereby said Cyc2 ring system is attached to the parent molecular group via any substitutable ring carbon atom of the constituent m,
in which
R6 is 1-4C-alkyl or 1-4C-alkoxy,
R7 is 1-4C-alkyl or 1-4C-alkoxy,
R8 is 1-4C-alkyl or 1-4C-alkoxy;
or, in yet another embodimental detail according to this invention,
either
Har is optionally substituted by R6 and/or R7 and/or R8, and is a 6-membered monocyclic unsaturated heteroarly radical comprising one or two nitrogen atoms,
or
Har is optionally substituted by R6 and/or R7, and is a 5-membered monocyclic unsaturated heteroarly radical comprising one to four heteroatoms selected independently from the group consisting of oxygen, nitrogen and sulphur,
in which
R6 is halogen, 1-4C-alkyl, 1-4C-alkoxy, 1-4C-alkoxy-ethoxy, cyano, 1-4C-alkoxycarbonyl, carboxyl, -A-N(R61)R62, or pyridyl, in which A is a bond or 1-2C-alkylene,
R61 is hydrogen or 1-2C-alkyl,
R62 is hydrogen or 1-2C-alkyl,
or R61 and R62 together and with inclusion of the nitrogen atom, to which they are attached, form a heterocyclic ring Het1, in which
either, in one facet,
Het1 is optionally substituted by R611 on a ring nitrogen atom, and is a 5- to 7-membered saturated monocyclic heterocyclic ring radical comprising the nitrogen atom, to which R61 and R62 are bonded, and optionally one further heteroatom selected from the group consisting of oxygen, nitrogen and sulfur, in which
R611 is 1-2C-alkyl,
or, in another facet,
Het1 is a 5-membered unsaturated monocyclic heteroaryl radical comprising the nitrogen atom, to which R61 and R62 are bonded, and optionally one to three further nitrogen atoms,
R7 is 1-4C-alkyl, 1-4C-alkoxy-ethoxy or 1-4C-alkoxy,
R8 is halogen, 1-4C-alkyl or 1-4C-alkoxy,
and the salts, the N-oxides and the salts of the N-oxides of these compounds.

Compounds of formula I according to aspect A in particular worthy to be mentioned in a sub-aspect (subaspect A2) are those in which
R1 is 1-2C-alkoxy, 3-5C-cycloalkoxy, 3-5C-cycloalkylmethoxy, 2,2-difluoroethoxy, or completely or predominantly fluorine-substituted 1-2C-alkoxy,
R2 is 1-2C-alkoxy, 3-5C-cycloalkoxy, 3-5C-cycloalkylmethoxy, 2,2-difluoroethoxy, or completely or predominantly fluorine-substituted 1-2C-alkoxy,
R3 is hydrogen,
R31 is hydrogen;
R4 is —O—R41, in which
R41 is 1-4C-alkylcarbonyl or hydrogen,
R5 is hydrogen;
In one embodimental detail according to this invention,
Har is Cyc1, in which
Cyc1 is a group of formula Z

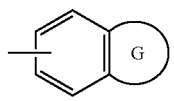

(Z)

in which
G is optionally substituted by R6 and/or R7, and is a 5- or 6-membered saturated or partially unsaturated heterocyclic ring comprising one or two heteroatoms independently selected from the group consisting of nitrogen, oxygen and sulfur,
whereby said Cyc1 ring system is attached to the parent molecular group via any substitutable carbon atom of the benzene ring,
in which
R6 is halogen, such as e.g. fluorine,
R7 is halogen, such as e.g. fluorine;
or, in another embodimental detail according to this invention,
Har is Cyc2, in which
Cyc2 is optionally substituted by R6 and/or R7 and/or R8, and is a 9- or 10-membered fused bicyclic fully aromatic ring system containing one to four heteroatoms each of which is selected from nitrogen, oxygen and sulphur, and which Cyc2 ring system is made up of
a first constituent (constituent m) being a benzene or pyridine ring, and fused to said first constituent m,
a second constituent (constituent n) being a 5- or 6-membered monocylic heteroaryl ring comprising one to three heteroatoms independently selected from the group consisting of nitrogen, oxygen and sulphur,
whereby said Cyc2 ring system is attached to the parent molecular group via any substitutable ring carbon atom of the constituent m,
in which
R6 is 1-4C-alkyl or 1-4C-alkoxy,
R7 is 1-4C-alkoxy,
R8 is 1-4C-alkyl;
or, in yet another embodimental detail according to this invention,
either
Har is optionally substituted by R6 and/or R7 and/or R8, and is a 6-membered monocyclic unsaturated heteroaryl radical comprising one or two nitrogen atoms, such as e.g. pyridinyl, pyrimidinyl or pyrazinyl,
in which
R6 is 1-4C-alkyl, 1-4C-alkoxy, cyano, 1-4C-alkoxycarbonyl, carboxyl, or -A-N(R61)R62, in which
A is a bond,
R61 and R62 together and with inclusion of the nitrogen atom, to which they are attached, form a heterocyclic ring Het1, in which
either, in one facet,
Het1 is optionally substituted by R611 on a ring nitrogen atom, and is a 5- to 7-membered saturated monocyclic heterocyclic ring radical comprising the nitrogen atom, to which R61 and R62 are bonded, and optionally one further heteroatom selected from the group consisting of oxygen, nitrogen and sulfur, such as e.g. piperidin-1-yl or morpholin-4-yl, in which
R611 is 1-2C-alkyl,
or, in another facet,
Het1 is a 5-membered unsaturated monocyclic heteroaryl radical comprising the nitrogen atom, to which R61 and R62 are bonded, and optionally one to three further nitrogen atoms, such as e.g. imidazol-1-yl or pyrazol-1-yl,
R7 is 1-4C-alkoxy,
R8 is halogen or 1-4C-alkoxy;
or
Har is optionally substituted by R6 and/or R7, and is a 5-membered monocyclic unsaturated heteroaryl radical comprising one to four heteroatoms selected independently from from the group consisting of oxygen, nitrogen and sulphur,
such as e.g. isoxazolyl, oxazolyl, imidazolyl or thiazolyl,
in which
R6 is 1-4C-alkyl or pyridyl
R7 is 1-4C-alkyl;
and the salts, the N-oxides and the salts of the N-oxides of these compounds.

Compounds of formula I according to aspect A in more particular worthy to be mentioned in a sub-aspect (subaspect A3) are those in which
R1 is 1-2C-alkoxy, 2,2-difluoroethoxy, or completely or predominantly fluorine-substituted 1-2C-alkoxy,
R2 is 1-2C-alkoxy, 2,2-difluoroethoxy, or completely or predominantly fluorine-substituted 1-2C-alkoxy,
R3 is hydrogen,
R31 is hydrogen;

R4 is —O—R41, in which
R41 is 1-4C-alkylcarbonyl such as e.g. acetyl, or, particularly, hydrogen,
R5 is hydrogen;
in one embodimental detail according to this invention,
Har is Cyc1, in which
Cyc1 is dihydrobenzo[1,4]dioxinyl, benzo[1,3]dioxolyl or 2,2-difluoro-benzo[1,3]dioxolyl;
or, in another embodimental detail according to this invention,
Har is Cyc2, in which
Cyc2 is optionally substituted by R6 and/or R7, and is quinolinyl, benzofurazanyl, benzothiazolyl, 1-(1-4C-alkyl)-1H-benzotriazolyl or 1-(1-4C-alkyl)-1H-pyrazolo[3,4-b]pyridinyl, in which
R6 is 1-4C-alkyl or 1-4C-alkoxy,
R7 is 1-4C-alkoxy;
or, in yet another embodimental detail according to this invention,
either
Har is optionally substituted by R6, and is pyridinyl, pyrimidinyl, pyrazinyl, isoxazolyl, 1-(1-4C-alkyl)-1H-imidazolyl or thiazolyl, in which
R6 is 1-4C-alkyl or pyridyl,
or
Har is substituted by R6 and/or R7 and/or R8, and is pyrimidinyl, in which
R6 is 1-4C-alkoxy,
R7 is 1-4C-alkoxy,
R8 is 1-4C-alkoxy,
or
Har is substituted by R6 and/or R7 and/or R8, and is pyridinyl, in which
R6 is 1-4C-alkoxy or 1-4C-alkoxycarbonyl,
R7 is 1-4C-alkoxy,
R8 is 1-4C-alkoxy or halogen,
or
Har is substituted by R6, and is pyridinyl, in which
R6 is morpholin-4-yl, piperidin-1-yl, pyrazol-1-yl or imidazol-1-yl;
and the salts, the N-oxides and the salts of the N-oxides of these compounds.

Compounds of formula I according to aspect A in still more particular worthy to be mentioned in a sub-aspect (subaspect A4) are those in which
R1 is 1-2C-alkoxy, 2,2-difluoroethoxy, or completely or predominantly fluorine-substituted 1-2C-alkoxy,
R2 is 1-2C-alkoxy, 2,2-difluoroethoxy, or completely or predominantly fluorine-substituted 1-2C-alkoxy,
R3 is hydrogen,
R31 is hydrogen;
R4 is —O—R41, in which
R41 is hydrogen
R5 is hydrogen;
in one embodimental detail according to this invention,
Har is Cyc1, in which
Cyc1 is dihydrobenzo[1,4]dioxinyl, benzo[1,3]dioxolyl or 2,2-difluoro-benzo[1,3]dioxolyl, such as e.g. dihydrobenzo[1,4]dioxin-6-yl, benzo[1,3]dioxol-5-yl, or 2,2-difluoro-benzo[1,3]dioxol-5-yl;
or, in another embodimental detail according to this invention,
Har is Cyc2, in which
either
Cyc2 is quinolinyl, benzofurazanyl or benzothiazolyl,
such as e.g. quinolin-6-yl, benzofurazan-5-yl or benzothiazol-6-yl,
or
Cyc2 is 1-(1-4C-alkyl)-1H-benzotriazolyl or 1-(1-4C-alkyl)-4-methoxy-3-methyl-1H-pyrazolo[3,4-b]pyridinyl,
such as e.g. 1-methyl-1H-benzotriazol-5-yl or 4-methoxy-1,3-dimethyl-1H-pyrazolo[3,4-b]pyridin-5-yl;
or, in yet another embodimental detail according to this invention,
either
Har is pyridinyl, pyrimidinyl, isoxazolyl, 1-(1-4C-alkyl)-1H-imidazolyl, methyl-pyrazinyl or pyridyl-thiazolyl,
such as e.g. pyridin-3-yl, pyridin-4-yl, pyrimidin-5-yl, pyrazin-2-yl, 5-methyl-pyrazin-2-yl, isoxazol-5-yl, 1-methyl-imidazol-2-yl, 1-methyl-imidazol-5-yl or 2-(pyridin-3-yl)-thiazol-4-yl,
or
Har is substituted by R6 and/or R7 and/or R8, and is pyrimidinyl, in which
R6 is 1-4C-alkoxy,
R7 is 1-4C-alkoxy,
R8 is 1-4C-alkoxy,
such as e.g. 2,6-dimethoxypyrimidin-4-yl, 2-methoxy-pyrimidin-5-yl, 2,4,6-trimethoxy-pyrimidin-5-yl, 2,4-dimethoxy-pyrimidin-5-yl or 2,6-dimethoxy-pyrimidin-4-yl,
or
Har is substituted by R6, and is pyridinyl, in which
R6 is 1-4C-alkoxycarbonyl,
such as e.g. 6-(methoxycarbonyl)-pyridin-3-yl or 5-(methoxycarbonyl)-pyridin-2-yl,
or
Har is substituted by R6, and is pyridinyl, in which
R6 is morpholin-4-yl, piperidin-1-yl, pyrazol-1-yl or imidazol-1-yl, such as e.g. 6-(morpholin-4-yl)-pyridin-3-yl, 6-(piperidin-1-yl)-pyridin-3-yl, 6-(pyrazol-1-yl)-pyridin-3-yl or 6-(imidazol-1-yl)-pyridin-3-yl,
or
Har is substituted by R6 and/or R7, and is pyridinyl, in which
R6 is 1-4C-alkoxy,
R7 is 1-4C-alkoxy,
such as e.g. 2,6-dimethoxy-pyridin-4-yl, 2,6-dimethoxy-pyridin-3-yl or 2-methoxy-pyridin-3-yl,
or
Har is substituted by R6 and R7 and R8, and is pyridinyl, in which
R6 is 1-4C-alkoxy,
R7 is 1-4C-alkoxy,
R8 is chlorine,
such as e.g. 3-chloro-2,6-dimethoxy-pyridin-4-yl;
and the salts, the N-oxides and the salts of the N-oxides of these compounds.

Yet compounds of formula I according to aspect A more worthy to be mentioned in a sub-aspect (sub-aspect A1') are those, in which
R1 is 1-2C-alkoxy, 3-5C-cycloalkoxy, 3-5C-cycloalkyl-methoxy, 2,2-difluoroethoxy, or completely or predominantly fluorine-substituted 1-2C-alkoxy,
R2 is 1-2C-alkoxy, 3-5C-cycloalkoxy, 3-5C-cycloalkyl-methoxy, 2,2-difluoroethoxy, or completely or predominantly fluorine-substituted 1-2C-alkoxy,
R3 is hydrogen,
R31 is hydrogen;
either, in a first embodiment (embodiment a) according to the present invention,
R4 is —O—R41, in which
R41 is hydrogen or 1-4C-alkylcarbonyl, and
R5 is hydrogen, or, in a second embodiment (embodiment b) according to the present invention,
R4 is hydrogen, and
R5 is —O—R51, in which
R51 is hydrogen or 1-4C-alkylcarbonyl;
in one embodimental detail according to this invention,
Har is optionally substituted by R6 and/or R7, and is a 9- or 10-membered fused bicyclic partially saturated heteroaryl radical comprising a heteroatom-free benzene ring and, in the other ring, 1 or 2 heteroatoms independently selected from oxygen, nitrogen and sulfur,
  whereby said Har ring system is attached to the parent molecular group via any substitutable carbon atom of the benzene ring,
in which
R6 is 1-4C-alkyl or halogen,
R7 is halogen;
or, in another embodimental detail according to this invention,
Har is Cyc2, in which
Cyc2 is optionally substituted by R6 and/or R7 and/or R8, and is a 9- or 10-membered fused bicyclic fully aromatic ring system containing one to four heteroatoms each of which is selected from nitrogen, oxygen and sulphur, and which Cyc2 ring system is made up of
  a first constituent (constituent m) being a benzene or pyridine ring,
  and fused to said first constituent m,
  a second constituent (constituent n) being a 5- or 6-membered monocylic heteroaryl ring comprising one to three heteroatoms independently selected from the group consisting of nitrogen, oxygen and sulphur,
  whereby said Cyc2 ring system is attached to the parent molecular group via any substitutable ring carbon atom of the constituent m,
in which
R6 is 1-4C-alkyl or 1-4C-alkoxy,
R7 is 1-4C-alkoxy,
R8 is 1-4C-alkyl;
or, in yet another embodimental detail according to this invention,
either
Har is optionally substituted by R6 and/or R7 and/or R8, and is a 6-membered monocyclic unsaturated heteroarly radical comprising one or two nitrogen atoms,
or
Har is optionally substituted by R6 and/or R7, and is a 5-membered monocyclic unsaturated heteroarly radical comprising one to four heteroatoms selected independently from the group consisting of oxygen, nitrogen and sulphur,
in which
R6 is halogen, 1-4C-alkyl, 1-4C-alkoxy, 1-4C-alkoxy-2-4C-alkoxy, 1-4C-alkylthio, sulfanyl, cyano, 1-4C-alkoxycarbonyl, carboxyl, hydroxyl, oxo, -A-N(R61)R62, or pyridyl, in which
A is a bond or 1-4C-alkylene,
R61 is hydrogen or 1-4C-alkyl,
R62 is hydrogen or 1-4C-alkyl,
or R61 and R62 together and with inclusion of the nitrogen atom, to which they are attached, form a heterocyclic ring Het1, in which
either, in one facet,
Het1 is optionally substituted by R611 on a ring nitrogen atom, and is a 5- to 7-membered saturated monocyclic heterocyclic ring radical comprising the nitrogen atom, to which R61 and R62 are bonded, and optionally one further heteroatom selected from the group consisting of oxygen, nitrogen and sulfur, in which
R611 is 1-4C-alkyl,
or, in another facet,
Het1 is a 5-membered unsaturated monocyclic heteroaryl radical comprising the nitrogen atom, to which R61 and R62 are bonded, and optionally one to three further nitrogen atoms,
R7 is 1-4C-alkyl, 1-4C-alkoxy, 1-4C-alkoxy-2-4C-alkoxy, 1-4C-alkylthio, sulfanyl, hydroxyl, oxo, amino, or mono- or di-1-4C-alkylamino,
R8 is halogen, 1-4C-alkyl or 1-4C-alkoxy,
and the enantiomers, as well as the salts, the N-oxides and the salts of the N-oxides of these compounds and enantiomers.

Yet compounds of formula I according to aspect A in particular worthy to be mentioned in a sub-aspect (subaspect A2') are those, in which
R1 is 1-2C-alkoxy, 2,2-difluoroethoxy, or completely or predominantly fluorine-substituted 1-2C-alkoxy,
R2 is 1-2C-alkoxy, 2,2-difluoroethoxy, or completely or predominantly fluorine-substituted 1-2C-alkoxy,
R3 is hydrogen,
R31 is hydrogen;
either, in a first embodiment (embodiment a) according to the present invention,
R4 is —O—R41, in which
R41 is hydrogen or 1-4C-alkylcarbonyl, and
R5 is hydrogen,
or, in a second embodiment (embodiment b) according to the present invention,
R4 is hydrogen, and
R5 is —O—R51, in which
R51 is hydrogen or 1-4C-alkylcarbonyl;
in one embodimental detail according to this invention,
Har is Cyc1, in which
Cyc1 is optionally substituted by halogen on its benzene ring, and is indolinyl, isoindolinyl, tetrahydroquinolinyl, tetrahydroisoquinolinyl, 3,4-dihydrobenzo[1,4]oxazinyl, 1-methyl-indolinyl, 2-methyl-isoindolinyl, 1-methyl-tetrahydroquinolinyl, 2-methyl-tetrahydroisoquinolinyl, 4-methyl-3,4-dihydrobenzo[1,4]oxazinyl, 2,3-dihydrobenzofuranyl, 2,3-dihydrobenzothiophenyl, benzo[1,3]dioxolyl, dihydro-benzo[1,4]dioxinyl, chromanyl, chromenyl, or 2,2-difluoro-benzo[1,3]dioxolyl,
whereby said Cyc1 ring system is attached to the parent molecular group via any substitutable carbon atom of the benzene ring;
or, in another embodimental detail according to this invention,
Har is Cyc2, in which
Cyc2 is optionally substituted by R6 and/or R7 and/or R8, and is a 9- or 10-membered fused bicyclic fully aromatic ring system containing one to three heteroatoms each of which is selected from nitrogen, oxygen and sulphur, and which Cyc2 ring system is made up of
  a first constituent (constituent m) being a benzene or pyridine ring,
  and fused to said first constituent m,
  a second constituent (constituent n) being a 5- or 6-membered monocytic heteroaryl ring comprising one to three heteroatoms independently selected from the group consisting of nitrogen, oxygen and sulphur,
  whereby said Cyc2 ring system is attached to the parent molecular group via any substitutable ring carbon atom of the constituent m, in which
R6 is 1-4C-alkyl or 1-4C-alkoxy,
R7 is 1-4C-alkoxy,
R8 is 1-4C-alkyl;
or, in yet another embodimental detail according to this invention,
Har is optionally substituted by R6 and/or R7 and/or R8, and is a pyridinyl, pyrimidinyl, pyrazinyl or pyridazinyl radical, in which
R6 is halogen, 1-4C-alkyl, 1-4C-alkoxy, 1-4C-alkylthio, 1-4C-alkoxycarbonyl, carboxyl, hydroxyl, oxo, or -A-N(R61)R62, in which
A is a bond or 1-4C-alkylene,
R61 is 1-4C-alkyl,
R62 is 1-4C-alkyl,
or R61 and R62 together and with inclusion of the nitrogen atom, to which they are attached, form a heterocyclic ring Het1, in which
either
Het1 is piperidin-1-yl, pyrrolidin-1-yl, morpholin-4-yl, thiomorpholin-4-yl, piperazin-1-yl or 4N-methyl-piperazin-1-yl,
or
Het1 is pyrrol-1-yl, pyrazol-1-yl, triazol-1-yl or imidazol-1-yl,
R7 is 1-4C-alkyl, 1-4C-alkoxy, 1-4C-alkylthio, hydroxyl, oxo, or di-1-4C-alkylamino,
R8 is halogen, 1-4C-alkyl or 1-4C-alkoxy;
or, in still yet another embodimental detail according to this invention,
Har is optionally substituted by R6 and/or R7, and is a 5-membered monocyclic unsaturated heteroarly radical comprising one to four heteroatoms selected independently from the group consisting of oxygen, nitrogen and sulphur,
in which
R6 is 1-4C-alkyl, or pyridyl,
R7 is 1-4C-alkyl,
and the enantiomers, as well as the salts, the N-oxides and the salts of the N-oxides of these compounds and enantiomers.

Yet compounds of formula I according to aspect A in more particular worthy to be mentioned in a sub-aspect (subaspect A3') are those, in which
one of R1 and R2 is methoxy or ethoxy, and the other is methoxy, ethoxy, 2,2-difluoroethoxy or difluoromethoxy,
R3 is hydrogen,
R31 is hydrogen;
R4 is —O—R41, in which
R41 is hydrogen or 1-4C-alkylcarbonyl, and
R5 is hydrogen,
in one embodimental detail according to this invention,
Har is Cyc1, in which
Cyc1 is optionally substituted by chlorine on its benzene ring, and is indolinyl, isoindolinyl, tetrahydroquinolinyl, tetrahydroisoquinolinyl, or 3,4-dihydrobenzo[1,4]oxazinyl, 1-methyl-indolinyl, 2-methyl-isoindolinyl, 1-methyl-tetrahydroquinolinyl, 2-methyl-tetrahydroisoquinolinyl, or 4-methyl-3,4-dihydrobenzo[1,4]oxazinyl, 2,3-dihydrobenzofuranyl, 2,3-dihydrobenzothiophenyl, benzo[1,3]dioxolyl, dihydro-benzo[1,4]dioxinyl, chromanyl, chromenyl, or 2,2-difluoro-benzo[1,3]dioxolyl,
whereby said Cyc1 ring system is attached to the parent molecular group via any substitutable carbon atom of the benzene ring;

or, in another embodimental detail according to this invention,
Har is Cyc2, in which
Cyc2 is optionally substituted by R6 and/or R7, and is either
pyrazolopyridinyl or 1-methyl-pyrazolopyridinyl,
whereby these radicals may be attached to the parent molecular group via the pyridine ring,
or
benzothiazolyl, benzoxazolyl, benzimidazolyl, indazolyl, 1-methyl-benzimidazolyl, 1-methyl-indazolyl, benzoxadiazolyl, benzotriazolyl, 1H-methyl-benzotriazolyl, benzothiadiazolyl, quinolinyl, isoquinolinyl, quinoxalinyl, quinazolinyl or cinnolinyl,
whereby these radicals may be attached to the parent molecular group via the benzene ring,
in which
R6 is 1-4C-alkyl or 1-4C-alkoxy,
R7 is 1-4C-alkoxy;
or, in yet another embodimental detail according to this invention,
Har is optionally substituted by R6 and/or R7 and/or R8, and is a pyridinyl, pyrimidinyl, pyrazinyl or pyridazinyl radical, in which
R6 is halogen, 1-4C-alkyl, 1-4C-alkoxy, 1-4C-alkylthio, 1-4C-alkoxycarbonyl, carboxyl, hydroxyl, oxo, or -A-N(R61)R62, in which
A is a bond or 1-4C-alkylene,
R61 is 1-4C-alkyl,
R62 is 1-4C-alkyl,
or R61 and R62 together and with inclusion of the nitrogen atom, to which they are attached, form a heterocyclic ring Het1, in which
either
Het1 is piperidin-1-yl, pyrrolidin-1-yl, morpholin-4-yl, thiomorpholin-4-yl, piperazin-1-yl or 4N-methyl-piperazin-1-yl,
or
Het1 is pyrrol-1-yl, pyrazol-1-yl, triazol-1-yl or imidazol-1-yl,
R7 is 1-4C-alkyl, 1-4C-alkoxy, 1-4C-alkylthio, hydroxyl, oxo, or di-1-4C-alkylamino,
R8 is halogen, 1-4C-alkyl or 1-4C-alkoxy;
or, in still yet another embodimental detail according to this invention,
Har is optionally substituted by R6 and/or R7, and is a 5-membered monocyclic unsaturated heteroarly radical comprising one to four heteroatoms selected independently from the group consisting of oxygen, nitrogen and sulphur,
in which
R6 is 1-4C-alkyl, or pyridyl,
R7 is 1-4C-alkyl,
and the enantiomers, as well as the salts, the N-oxides and the salts of the N-oxides of these compounds and enantiomers.

Yet compounds of formula I according to aspect A in still more particular worthy to be mentioned in a sub-aspect (sub-aspect A4') are those, in which
R1 is methoxy or ethoxy,
R2 is methoxy, ethoxy, 2,2-difluoroethoxy or difluoromethoxy,
R3 is hydrogen,
R31 is hydrogen;
R4 is —O—R41, in which
R41 is hydrogen or acetyl, and
R5 is hydrogen, in one embodimental detail according to this invention,
Har is Cyc1, in which
Cyc1 is benzo[1,3]dioxol-5-yl, dihydrobenzo[1,4]dioxin-5-yl, 2,2-difluoro-benzo[1,3]dioxol-5-yl, or 5-chloro-4-methyl-3,4-dihydrobenzo[1,4]oxazin-7-yl;
or, in another embodimental detail according to this invention,
Har is Cyc2, in which
Cyc2 is quinolin-6-yl, benzofurazan-5-yl, benzothiazol-6-yl, 1-methyl-1H-benzotriazol-5-yl or 4-methoxy-1,3-dimethyl-1H-pyrazolo[3,4-b]pyridin-5-yl, benzo[1,2,3]thiadiazol-5-yl or quinoxalin-5-yl;
or, in yet another embodimental detail according to this invention,
Har is optionally substituted by R6 and/or R7 and/or R8, and is a pyridinyl, pyrimidinyl, pyrazinyl or pyridazinyl radical, in which
R6 is chlorine, methyl, methoxy, ethoxy, methylthio, methoxycarbonyl, carboxyl, hydroxyl, oxo, or -A-N(R61)R62, in which
A is a bond or ethylene,
R61 is methyl,
R62 is methyl,
or R61 and R62 together and with inclusion of the nitrogen atom, to which they are attached, form a heterocyclic ring Het1, in which
either
Het1 is piperidin-1-yl, pyrrolidin-1-yl or morpholin-4-yl, or
Het1 is pyrazol-1-yl or imidazol-1-yl,
R7 is methyl, methoxy, ethoxy, methylthio or dimethylamino,
R8 is chlorine or methoxy;
or, in still yet another embodimental detail according to this invention,
Har is isoxazolyl, 1-methylimidazolyl, or pyridyl-thiazolyl; and the enantiomers, as well as the salts, the N-oxides and the salts of the N-oxides of these compounds and enantiomers.

Particular compounds of formula I according to aspect A to be mentioned in a sub-aspect (subaspect A5) are those, in which
R1 is methoxy,
R2 is methoxy, ethoxy, 2,2-difluoroethoxy or difluoromethoxy,
R3 is hydrogen,
R31 is hydrogen;
R4 is —O—R41, in which
R41 is hydrogen or acetyl, and
R5 is hydrogen,
in one embodimental detail according to this invention,
Har is Cyc1, in which
Cyc1 is benzo[1,3]dioxol-5-yl, dihydrobenzo[1,4]dioxin-5-yl, 2,2-difluoro-benzo[1,3]dioxol-5-yl, or 5-chloro-4-methyl-3,4-di hydrobenzo[1,4]oxazin-7-yl;
or, in another embodimental detail according to this invention,
Har is Cyc2, in which
Cyc2 is quinolin-6-yl, benzofurazan-5-yl, benzothiazol-6-yl, 1-methyl-1H-benzotriazol-5-yl or 4-methoxy-1,3-dimethyl-1H-pyrazolo[3,4-b]pyridin-5-yl, benzo[1,2,3]thiadiazol-5-yl or quinoxalin-5-yl;
or, in yet another embodimental detail according to this invention,
Har is pyridin-3-yl, pyridin-4-yl, 6-(piperidin-1-yl)-pyridin-3-yl, 6-(pyrazol-1-yl)-pyridin-3-yl, 6-(imidazol-1-yl)-pyridin-3-yl, 6-methoxycarbonyl-pyridin-3-yl, 3-methoxycarbonyl-pyridin-2-yl, 2-methoxy-pyridin-3-yl, 6-methoxy-pyridin-3-yl, 2-methylsulfanyl-pyridin-3-yl, 6-hydroxy-pyridin-3-yl, 6-carboxy-pyridin-3-yl, pyrimidin-5-yl, 2-methoxy-pyrimidin-5-yl, 2-dimethylamino-pyrimidin-5-yl, 2-methylsulfanyl-pyrimidin-5-yl, pyrazin-2-yl, 5-methyl-pyrazin-2-yl, 2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl, 1-methyl-1H-pyridin-2-one-5-yl, 2,6-dimethoxy-pyrimidin-4-yl, 2,4-dimethoxy-pyrimidin-5-yl, 4,6-di methoxy-pyrimidin-5-yl, 4-methyl-2-methylsulfanyl-pyrimidin-5-yl, 5-chloro-2-methylsulfanyl-pyrimidin-4-yl, 4-chloro-2-dimethylamino-pyrimidin-5-yl, 2-dimethylamino-4-methoxy-pyrimidin-5-yl, 1-methyl-1H-pyrimidin-2-one-5-yl, 3,6-dimethoxy-pyridazin-4-yl, 4-chloro-2,6-dimethoxy-pyridin-3-yl, 3-chloro-2,6-dimethoxy-pyridin-4-yl, 5-chloro-2,6-bisdimethylamino-pyrimidin-4-yl, or 2,4,6-trimethoxy-pyrimidin-5-yl;
or, in still yet another embodimental detail according to this invention,
Har is isoxazol-5-yl, 1-methylimidazol-2-yl, 1-methylimidazol-5-yl, or 2-(pyridin-3-yl)-thiazol-4-yl; and the enantiomers, as well as the salts, the N-oxides and the salts of the N-oxides of these compounds and enantiomers.

More particular compounds of formula I according to aspect A to be mentioned in a sub-aspect (sub-aspect A6) are those, in which
R1 is methoxy,
R2 is ethoxy, 2,2-difluoroethoxy or difluoromethoxy,
R3 is hydrogen,
R31 is hydrogen;
R4 is —O—R41, in which
R41 is hydrogen, and
R5 is hydrogen,
in one embodimental detail according to this invention,
Har is Cyc1, in which
Cyc1 is benzo[1,3]dioxol-5-yl, dihydrobenzo[1,4]dioxin-5-yl, 2,2-difluoro-benzo[1,3]dioxol-5-yl, or 5-chloro-4-methyl-3,4-dihydrobenzo[1,4]oxazin-7-yl;
or, in another embodimental detail according to this invention,
Har is Cyc2, in which
Cyc2 is quinolin-6-yl, benzofurazan-5-yl, benzothiazol-6-yl, 1-methyl-1H-benzotriazol-5-yl or 4-methoxy-1,3-dimethyl-1H-pyrazolo[3,4-b]pyridin-5-yl, benzo[1,2,3]thiadiazol-5-yl or quinoxalin-5-yl;
or, in yet another embodimental detail according to this invention,
Har is pyridin-3-yl, pyridin-4-yl, 6-(morpholin-4-yl)-pyridin-3-yl, 6-(piperidin-1-yl)-pyridin-3-yl, 6-(pyrazol-1-yl)-pyridin-3-yl, 6-(imidazol-1-yl)-pyridin-3-yl, 6-methoxycarbonyl-pyridin-3-yl, 3-methoxycarbonyl-pyridin-2-yl, 2-methoxy-pyridin-3-yl, 6-methoxy-pyridin-3-yl, 2-methylsulfanyl-pyridin-3-yl, 6-hydroxy-pyridin-3-yl, 6-carboxy-pyridin-3-yl, pyrimidin-5-yl, 2-methoxy-pyrimidin-5-yl, 2-dimethylamino-pyrimidin-5-yl, 2-methylsulfanyl-pyrimidin-5-yl, pyrazin-2-yl, 5-methyl-pyrazin-2-yl, 6-[2-(pyrrolidin-1-yl)-ethyl]-pyridin-3-yl, 2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl, 1-methyl-1H-pyridin-2-one-5-yl, 2,6-dimethoxy-pyrimidin-4-yl, 2,4-dimethoxy-pyrimidin-5-yl, 4,6-dimethoxy-pyrimidin-5-yl, 4-methyl-2-methylsulfanyl-pyrimidin-5-yl, 5-chloro-2-methylsulfanyl-pyrimidin-4-yl, 4-chloro-2-dimethylamino-pyrimidin-5-yl, 2-dimethylamino-4-methoxy-pyrimidin-5-yl, 1-methyl-1H-pyrimidin-2-one-5-yl, 3,6-dimethoxy-pyridazin-4-yl, 4-chloro-2,6- dimethoxy-pyridin-3-yl, 3-chloro-2,6-dimethoxy-pyridin-4-yl, 5-chloro-2,6-bisdimethylamino-pyrimidin-4-yl, or 2,4,6-trimethoxy-pyrimidin-5-yl;

or, in still yet another embodimental detail according to this invention,

Har is isoxazol-5-yl, 1-methylimidazol-2-yl, 1-methylimidazol-5-yl, or 2-(pyridin-3-yl)-thiazol-4-yl;

and the enantiomers, as well as the salts, the N-oxides and the salts of the N-oxides of these compounds and enantiomers.

Compounds of formula I according to aspect B more worthy to be mentioned in a sub-aspect (subaspect B1) are those in which R1 is 1-2C-alkoxy, 3-5C-cycloalkoxy, 3-5C-cycloalkylmethoxy, 2,2-difluoroethoxy, or completely or predominantly fluorine-substituted 1-2C-alkoxy, R2 is 1-2C-alkoxy, 3-5C-cycloalkoxy, 3-5C-cycloalkylmethoxy, 2,2-difluoroethoxy, or completely or predominantly fluorine-substituted 1-2C-alkoxy, R3 is hydrogen, R31 is hydrogen, either, in a first embodiment (embodiment a) according to the present invention, R4 is —O—R41, in which R41 is hydrogen or 1-4C-alkylcarbonyl, and R5 is hydrogen, or, in a second embodiment (embodiment b) according to the present invention, R4 is hydrogen, and R5 is —O—R51, in which R51 is hydrogen or 1-4C-alkylcarbonyl, Har is optionally substituted by R6 and/or R7 and/or R8, and is a 9- or 10-membered benzofused bicyclic partially saturated heteroaryl radical comprising 1 or 2 heteroatoms selected independently from the group consisting of oxygen, nitrogen and sulfur, or a 9- or 10-membered fused bicyclic unsaturated heteroaryl radical comprising 1 to 4 heteroatoms selected independently from the group consisting of oxygen, nitrogen and sulfur, or a 5- or 6-membered monocyclic unsaturated heteroaryl radical comprising 1 to 4 heteroatoms selected independently from the group consisting of oxygen, nitrogen and sulfur, in which R6 is halogen, 1-4C-alkyl, 1-4C-alkoxy, 1-4C-alkoxy-2-4C-alkoxy, 1-4C-alkylthio, cyano, 1-4C-alkoxycarbonyl, carboxyl, hydroxyl, -A-N(R61)R62, pyridyl, or completely or partially fluorine-substituted 1-4C-alkyl, in which A is a bond or 1-4C-alkylene, R61 is hydrogen or 1-4C-alkyl, R62 is hydrogen or 1-4C-alkyl, or R61 and R62 together and with inclusion of the nitrogen atom, to which they are attached, form a heterocyclic ring Het1, in which either, in one facet, Het1 is optionally substituted by R611 on a ring nitrogen atom, and is a 3- to 7-membered saturated monocyclic heterocyclic ring radical comprising the nitrogen atom, to which R61 and R62 are bonded, and optionally one further heteroatom selected from the group consisting of oxygen, nitrogen and sulfur, in which R611 is 1-4C-alkyl, or, in another facet, Het1 is a 5-membered unsaturated monocyclic heterocyclic ring radical comprising the nitrogen atom, to which R61 and R62 are bonded, and optionally one to three further nitrogen atoms, R7 is 1-4C-alkoxy, 1-4C-alkoxy-2-4C-alkoxy, 1-4C-alkylthio, hydroxyl, amino or mono- or di-1-4C-alkylamino, R8 is halogen, and the salts, the N-oxides and the salts of the N-oxides of these compounds.

Compounds of formula I according to aspect B in particular worthy to be mentioned in a sub-aspect (subaspect B2) are those in which R1 is 1-2C-alkoxy, 3-5C-cycloalkoxy, 3-5C-cycloalkylmethoxy, 2,2-difluoroethoxy, or completely or predominantly fluorine-substituted 1-2C-alkoxy, R2 is 1-2C-alkoxy, 3-5C-cycloalkoxy, 3-5C-cycloalkylmethoxy, 2,2-difluoroethoxy, or completely or predominantly fluorine-substituted 1-2C-alkoxy, R3 is hydrogen, R31 is hydrogen, R4 is —O—R41, in which R41 is 1-4C-alkylcarbonyl or, in particular, in an individual embodiment according to this invention, hydrogen, R5 is hydrogen, in one embodimental detail according to this invention, Har is optionally substituted by R6 and/or R7, and is a 9- or 10-membered benzofused bicyclic partially saturated heteroaryl radical comprising 1 or 2 heteroatoms selected independently from the group consisting of oxygen, nitrogen and sulfur, in which R6 is 1-2C-alkyl or halogen, R7 is halogen;

or, in another embodimental detail according to this invention,

Har is optionally substituted by R6, and is a 9- or 10-membered fused bicyclic unsaturated heteroaryl radical comprising 1 to 3 heteroatoms selected independently from the group consisting of oxygen, nitrogen and sulfur, in which R6 is 1-4C-alkyl;

or, in yet another embodimental detail according to this invention,

Har is optionally substituted by R6 and/or R7 and/or R8, and is a 5- or 6-membered monocyclic unsaturated heteroaryl radical comprising 1 to 3 heteroatoms selected independently from the group consisting of oxygen, nitrogen and sulfur, in which R6 is halogen, 1-4C-alkyl, 1-4C-alkoxy, 1-4C-alkoxyethoxy, 1-2C-alkylthio, cyano, 1-2C-alkoxycarbonyl, carboxyl, hydroxyl, -A-N(R61)R62, pyridyl, or completely or partially fluorine-substituted 1-2C-alkyl, in which A is a bond or 1-2C-alkylene, R61 is hydrogen or 1-2C-alkyl, R62 is hydrogen or 1-2C-alkyl, or R61 and R62 together and with inclusion of the nitrogen atom, to which they are attached, form a heterocyclic ring Het1, in which either, in one facet, Het1 is optionally substituted by R611 on a ring nitrogen atom, and is a 5- to 7-membered saturated monocyclic heterocyclic ring radical comprising the nitrogen atom, to which R61 and R62 are bonded, and optionally one further heteroatom selected from the group consisting of oxygen, nitrogen and sulfur, in which R611 is 1-2C-alkyl, or, in another facet, Het1 is a 5-membered unsaturated monocyclic heterocyclic ring radical comprising the nitrogen atom, to which R61 and R62 are bonded, and optionally one or two further nitrogen atoms, R7 is 1-4C-alkoxy, 1-4C-alkoxy-ethoxy, 1-2C-alkylthio, hydroxyl, amino, or mono- or di-1-2C-alkylamino, R8 is halogen;

and the salts, the N-oxides and the salts of the N-oxides of these compounds.

Compounds of formula I according to aspect B in more particular worthy to be mentioned in a sub-aspect (subaspect B3) are those in which R1 is 1-2C-alkoxy, 3-5C-cycloalkoxy, 3-5C-cycloalkyl-methoxy, 2,2-difluoroethoxy, or completely or predominantly fluorine-substituted 1-2C-alkoxy, R2 is 1-2C-alkoxy, 3-5C-cycloalkoxy, 3-5C-cycloalkyl-methoxy, 2,2-difluoroethoxy, or completely or predominantly fluorine-substituted 1-2C-alkoxy, R3 is hydrogen, R31 is hydrogen, R4 is —O—R41, in which R41 is hydrogen, R5 is hydrogen, in one embodimental detail according to this invention, Har is optionally substituted by R6 and/or R7, and is a 9- or 10-membered benzofused bicyclic partially saturated heteroaryl radical comprising 1 or 2 heteroatoms selected independently from the group consisting of oxygen, nitrogen and sulfur, in which R6 is 1-2C-alkyl or halogen, R7 is halogen;

or, in another embodimental detail according to this invention,

Har is optionally substituted by R6, and is a 9- or 10-membered fused bicyclic unsaturated heteroaryl radical comprising 1 to 3 heteroatoms selected independently from the group consisting of oxygen, nitrogen and sulfur, in which R6 is 1-4C-alkyl;

or, in yet another embodimental detail according to this invention, either

Har is optionally substituted by R6, and is a 5-membered monocyclic unsaturated heteroaryl radical comprising 1 to 3 heteroatoms selected independently from the group consisting of oxygen, nitrogen and sulfur, in which R6 is 1-4C-alkyl or pyridyl, or Har is optionally substituted by R6 and/or R7, and is a 6-membered monocyclic unsaturated heteroaryl radical comprising 1 or 2 nitrogen atoms, in which R6 is 1-4C-alkoxy, 1-2C-alkoxy-ethoxy or -A-N(R61)R62, in which A is a bond, R61 and R62 together and with inclusion of the nitrogen atom, to which they are attached, form a heterocyclic ring Het1, in which either, in one facet, Het1 is optionally substituted by R611 on a ring nitrogen atom, and is a 5- to 7-membered saturated monocyclic heterocyclic ring radical comprising the nitrogen atom, to which R61 and R62 are bonded, and optionally one further heteroatom selected from the group consisting of oxygen, nitrogen and sulfur, in which R611 is 1-2C-alkyl, or, in another facet, Het1 is a 5-membered unsaturated monocyclic heterocyclic ring radical comprising the nitrogen atom, to which R61 and R62 are bonded, and optionally one or two further nitrogen atoms, R7 is 1-4C-alkoxy or 1-2C-alkoxy-ethoxy;

and the salts, the N-oxides and the salts of the N-oxides of these compounds.

Compounds of formula I according to aspect B in still more particular worthy to be mentioned in a sub-aspect (subaspect B4) are those in which R1 is 1-2C-alkoxy, 2,2-difluoroethoxy, or completely or predominantly fluorine-substituted 1-2C-alkoxy, R2 is 1-2C-alkoxy, 2,2-difluoroethoxy, or completely or predominantly fluorine-substituted 1-2C-alkoxy, R3 is hydrogen, R31 is hydrogen, R4 is —O—R41, in which R41 is hydrogen, R5 is hydrogen, in one embodimental detail according to this invention, Har is optionally substituted by R6 and/or R7, and is benzo[1,4]dioxanyl or benzo[1,3]dioxolyl, in which R6 is fluorine, R7 is fluorine;

or, in another embodimental detail according to this invention,

Har is quinolinyl, benzofurazanyl or benzothiazolyl;

or, in yet another embodimental detail according to this invention, either

Har is optionally substituted by R6 and/or R7, and is pyridinyl, in which

R6 is 1-4C-alkoxy, -A-N(R61)R62, in which

A is a bond,

R61 and R62 together and with inclusion of the nitrogen atom, to which they are attached, form a heterocyclic ring Het1, in which Het1 is morpholinyl, thiomorpholinyl, N—(R611)-piperazinyl or 4-N—(R611)-homopiperazinyl, in which R611 is 1-2C-alkyl, R7 is 1-4C-alkoxy, or Har is optionally substituted by R6, and is isoxazolyl, imidazolyl or thiazolyl, in which R6 is 1-4C-alkyl or pyridyl;

and the salts, the N-oxides and the salts of the N-oxides of these compounds.

Compounds of formula I according to aspect C more worthy to be mentioned in a sub-aspect (subaspect C1) are those, in which R1 is 1-2C-alkoxy, 3-5C-cycloalkoxy, 3-5C-cycloalkyl-methoxy, 2,2-difluoroethoxy, or completely or predominantly fluorine-substituted 1-2C-alkoxy, R2 is 1-2C-alkoxy, 3-5C-cycloalkoxy, 3-5C-cycloalkyl-methoxy, 2,2-difluoroethoxy, or completely or predominantly fluorine-substituted 1-2C-alkoxy, R3 is hydrogen, R31 is hydrogen, either, in a first embodiment (embodiment a) according to the present invention, R4 is —O—R41, in which R41 is hydrogen or 1-4C-alkylcarbonyl, and R5 is hydrogen, or, in a second embodiment (embodiment b) according to the present invention,
R4 is hydrogen, and
R5 is —O—R51, in which
R51 is hydrogen or 1-4C-alkylcarbonyl,
Har is optionally substituted by R6 and/or R7 and/or R8, and is a pyridinyl, pyrimidinyl, pyrazinyl or pyridazinyl radical, in which
R6 is halogen, 1-4C-alkyl, 1-4C-alkoxy, 1-4C-alkoxy-2-4C-alkoxy, 1-4C-alkylthio, sulfanyl, cyano, 1-4C-alkoxycarbonyl, carboxyl, hydroxyl, oxo, or -A-N(R61)R62, in which
A is a bond or 1-4C-alkylene,
R61 is hydrogen or 1-4C-alkyl,
R62 is hydrogen or 1-4C-alkyl,
or R61 and R62 together and with inclusion of the nitrogen atom, to which they are attached, form a heterocyclic ring Het1, in which
either
Het1 is piperidin-1-yl, pyrrolidin-1-yl, morpholin-4-yl, thiomorpholin-4-yl, piperazin-1-yl or 4N-(1-4C-alkyl)-piperazin-1-yl,
or
Het1 is pyrrol-1-yl, pyrazol-1-yl, triazol-1-yl, or imidazol-1-yl,
R7 is 1-4C-alkyl, 1-4C-alkoxy, 1-4C-alkoxy-2-4C-alkoxy, 1-4C-alkylthio, sulfanyl, hydroxyl, oxo, amino or di-1-4C-alkylamino,
R8 is halogen, 1-4C-alkyl or 1-4C-alkoxy,
and the enantiomers, as well as the salts, the N-oxides and the salts of the N-oxides of these compounds and enantiomers.

Compounds of formula I according to aspect C in particular worthy to be mentioned in a sub-aspect (subaspect C2) are those, in which
R1 is 1-2C-alkoxy, 2,2-difluoroethoxy, or completely or predominantly fluorine-substituted 1-2C-alkoxy,
R2 is 1-2C-alkoxy, 2,2-difluoroethoxy, or completely or predominantly fluorine-substituted 1-2C-alkoxy,
R3 is hydrogen,
R31 is hydrogen,
R4 is —O—R41, in which
R41 is hydrogen or 1-4C-alkylcarbonyl,
R5 is hydrogen,
Har is optionally substituted by R6 and/or R7 and/or R8, and is a pyridinyl, pyrimidinyl, pyrazinyl or pyridazinyl radical, in which
R6 is halogen, 1-4C-alkyl, 1-4C-alkoxy, 1-4C-alkylthio, 1-4C-alkoxycarbonyl, carboxyl, hydroxyl, oxo, or -A-N(R61)R62, in which
A is a bond or 1-4C-alkylene,
R61 is 1-4C-alkyl,
R62 is 1-4C-alkyl,
or R61 and R62 together and with inclusion of the nitrogen atom, to which they are attached, form a heterocyclic ring Het1, in which
either
Het1 is piperidin-1-yl, pyrrolidin-1-yl, morpholin-4-yl, thiomorpholin-4-yl, piperazin-1-yl or 4N-methyl-piperazin-1-yl,
or
Het1 is pyrrol-f-yl, pyrazol-1-yl, triazol-1-yl or imidazol-1-yl,
R7 is 1-4C-alkyl, 1-4C-alkoxy, 1-4C-alkylthio, hydroxyl, oxo, or di-1-4C-alkylamino,
R8 is halogen, 1-4C-alkyl or 1-4C-alkoxy,
and the enantiomers, as well as the salts, the N-oxides and the salts of the N-oxides of these compounds and enantiomers.

Compounds of formula I according to aspect C in more particular worthy to be mentioned in a sub-aspect (subaspect C3) are those, in which one of R1 and R2 is methoxy or ethoxy, and the other is methoxy, ethoxy, difluoromethoxy or 2,2-difluoroethoxy, and
R3 is hydrogen,
R31 is hydrogen,
R4 is —O—R41, in which
R41 is hydrogen,
R5 is hydrogen,
Har is optionally substituted by R6 and/or R7 and/or R8, and is a pyridinyl, pyrimidinyl, pyrazinyl or pyridazinyl radical, in which
R6 is halogen, 1-4C-alkyl, 1-4C-alkoxy, 1-4C-alkylthio, 1-4C-alkoxycarbonyl, carboxyl, hydroxyl, oxo, or -A-N(R61)R62, in which
A is a bond or 1-2C-alkylene,
R61 is 1-4C-alkyl,
R62 is 1-4C-alkyl,
or R61 and R62 together and with inclusion of the nitrogen atom, to which they are attached, form a heterocyclic ring Het1, in which
either
Het1 is piperidin-1-yl, pyrrolidin-1-yl or morpholin-4-yl,
or
Het1 is pyrazol-1-yl or imidazol-1-yl,
R7 is 1-4C-alkyl, 1-4C-alkoxy, 1-4C-alkylthio, hydroxyl, oxo, or di-1-4C-alkylamino,
R8 is halogen or 1-4C-alkoxy,
and the enantiomers, as well as the salts, the N-oxides and the salts of the N-oxides of these compounds and enantiomers.

Compounds of formula I according to aspect C in still more particular worthy to be mentioned in a sub-aspect (subaspect C4) are those, in which
R1 is methoxy or ethoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is substituted by R6, and is a pyridinyl, pyrimidinyl, pyrazinyl or pyridazinyl radical, in which
R6 is methyl, methoxy, ethoxy, methylthio, methoxycarbonyl, carboxyl, hydroxyl, or -A-N(R61)R62, in which
A is a bond, methylene or ethylene,
R61 is methyl,
R62 is methyl,
or R61 and R62 together and with inclusion of the nitrogen atom, to which they are attached, form a heterocyclic ring Het1, in which
either
Het1 is piperidin-1-yl, pyrrolidin-1-yl or morpholin-4-yl,
or
Het1 is pyrazol-1-yl or imidazol-1-yl,
and the enantiomers, as well as the salts, the N-oxides and the salts of the N-oxides of these compounds and enantiomers.

Particular compounds of formula I according to subaspect C4 of this invention are those, in which
R1 is methoxy,
R2 is methoxy, ethoxy, difluoromethoxy or 2,2-difluoroethoxy,
R3 is hydrogen,
R31 is hydrogen, R4 is —O—R41, in which
R41 is hydrogen,
R5 is hydrogen,
Har is substituted by R6, and is pyridinyl, in which
R6 is methoxy, ethoxy, methylthio, methoxycarbonyl, hydroxyl, carboxyl, or -A-N(R61)R62, in which
A is a bond, or ethylene,
R61 is methyl,
R62 is methyl,
or R61 and R62 together and with inclusion of the nitrogen atom, to which they are attached, form a heterocyclic ring Het1, in which
either
Het1 is piperidin-1-yl, pyrrolidin-1-yl or morpholin-4-yl,
or
Het1 is pyrazol-1-yl or imidazol-1-yl,
and the enantiomers, as well as the salts, the N-oxides and the salts of the N-oxides of these compounds and enantiomers.

Other particular compounds of formula I according to sub-aspect C4 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is substituted by R6, and is pyrimidinyl, in which
R6 is methoxy, ethoxy, methylthio, or -A-N(R61)R62, in which
A is a bond,
R61 is methyl,
R62 is methyl,
and the enantiomers, as well as the salts, the N-oxides and the salts of the N-oxides of these compounds and enantiomers.

More particular compounds of formula I according to sub-aspect C4 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is 6-(morpholin-4-yl)-pyridin-3-yl, 6-(piperidin-1-yl)-pyridin-3-yl, 6-(pyrazol-1-yl)-pyridin-3-yl, 6-(imidazol-1-yl)-pyridin-3-yl, 6-methoxycarbonyl-pyridin-3-yl, 3-methoxycarbonyl-pyridin-2-yl, 2-methoxy-pyridin-3-yl, 6-methoxy-pyridin-3-yl, 2-methylsulfanyl-pyridin-3-yl, 6-hydroxy-pyridin-3-yl, 6-carboxy-pyridin-3-yl, 2-methoxy-pyrimidin-5-yl, 2-dimethylamino-pyrimidin-5-yl, 2-methylsulfanyl-pyrimidin-5-yl, 5-methyl-pyrazin-2-yl, or 6-[2-(pyrrolidin-1-yl)-ethyl]-pyridin-3yl,
and the enantiomers, as well as the salts, the N-oxides and the salts of the N-oxides of these compounds and enantiomers.

Compounds of formula I according to subaspect C4 of this invention to be emphasized are those, in which
R1 is methoxy,
R2 is ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is methoxy-pyrimidinyl, methylthio-pyrimidinyl, dimethylamino-pyrimidinyl, or imidazol-1-yl-pyridinyl,
and the enantiomers, as well as the salts, the N-oxides and the salts of the N-oxides of these compounds and enantiomers.

Compounds of formula I according to aspect C4 of this invention to be more emphasized are those, in which
R1 is methoxy,
R2 is ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is 6-(imidazol-1-yl)-pyridin-3-yl, 2-methoxy-pyrimidin-5-yl, 2-dimethylamino-pyrimidin-5-yl, or 2-methylsulfanyl-pyrimidin-5-yl,
and the enantiomers, as well as the salts, the N-oxides and the salts of the N-oxides of these compounds and enantiomers.

Further compounds of formula I according to aspect C in still more particular worthy to be mentioned in a sub-aspect (subaspect C5) are those, in which
R1 is methoxy or ethoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
either
Har is substituted by R6 and R7, and is a pyridinyl, pyrimidinyl, pyrazinyl or pyridazinyl radical, in which
R6 is chlorine, methoxy, ethoxy, methylthio, oxo, or -A-N(R61)R62, in which
A is a bond,
R61 is methyl,
R62 is methyl, and
R7 is methyl, methoxy, ethoxy, methylthio, or dimethylamino,
or
Har is substituted by R6 and R8, and is a pyridinyl, pyrimidinyl, pyrazinyl or pyridazinyl radical, in which
R6 is -A-N(R61)R62, in which
A is a bond,
R61 is methyl,
R62 is methyl, and
R8 is chlorine,
and the enantiomers, as well as the salts, the N-oxides and the salts of the N-oxides of these compounds and enantiomers.

Particular compounds of formula I according to subaspect C5 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
either
Har is substituted by R6 and R7, and is a pyridinyl, pyrimidinyl, pyridazinyl or pyrazinyl radical, in which
R6 is methoxy or ethoxy, and
R7 is methoxy or ethoxy, or
R6 is oxo, and
R7 is methyl,
or
R6 is methylthio, and
R7 is methyl,
or
R6 is chlorine, and
R7 is methylthio,
or
R6 is dimethylamino, and
R7 is methoxy or ethoxy,
or
R6 is dimethylamino, and
R7 is dimethylamino,
or
Har is substituted by R6 and R8, and is a pyridinyl, pyrimidinyl, pyridazinyl or pyrazinyl radical, in which
R6 is dimethylamino, and
R8 is chlorine,
and the enantiomers, as well as the salts, the N-oxides and the salts of the N-oxides of these compounds and enantiomers.

More particular compounds of formula I according to subaspect C5 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is substituted by R6 and R7, and is pyridinyl, in which
either
R6 is methoxy or ethoxy, and
R7 is methoxy or ethoxy,
or
R6 is oxo, and
R7 is methyl,
and the enantiomers, as well as the salts, the N-oxides and the salts of the N-oxides of these compounds and enantiomers.

Other more particular compounds of formula I according to subaspect C5 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
either
Har is substituted by R6 and R7, and is pyrimidinyl, in which
R6 is methoxy or ethoxy, and
R7 is methoxy or ethoxy,
or
R6 is oxo, and
R7 is methyl,
or
R6 is methylthio, and
R7 is methyl,
or
R6 is chlorine, and
R7 is methylthio,
or
R6 is dimethylamino, and
R7 is methoxy or ethoxy,
or
Har is substituted by R6 and R8, and is pyrimidinyl, in which
R6 is dimethylamino, and
R8 is chlorine,
and the enantiomers, as well as the salts, the N-oxides and the salts of the N-oxides of these compounds and enantiomers.

Other more particular compounds of formula I according to subaspect C5 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is substituted by R6 and R7, and is pyridazinyl, in which
R6 is methoxy or ethoxy, and
R7 is methoxy or ethoxy,
and the enantiomers, as well as the salts, the N-oxides and the salts of the N-oxides of these compounds and enantiomers.

Yet more particular compounds of formula I according to subaspect C5 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is 2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl, 1-methyl-1H-pyridin-2-one-5-yl, 2,6-dimethoxy-pyrimidin-4-yl, 2,4-dimethoxy-pyrimidin-5-yl, 4,6-dimethoxy-pyrimidin-5-yl, 4-methyl-2-methylsulfanyl-pyrimidin-5-yl, 5-chloro-2-methylsulfanyl-pyrimidin-4-yl, 4-chloro-2-dimethylamino-pyrimidin-5-yl, 2-dimethylamino-4-methoxy-pyrimidin-5-yl, 1-methyl-1H-pyrimidin-2-one-5-yl, or 3,6-dimethoxy-pyridazin-4-yl,
and the enantiomers, as well as the salts, the N-oxides and the salts of the N-oxides of these compounds and enantiomers.

Compounds of formula I according to aspect C5 of this invention to be emphasized are those, in which
R1 is methoxy,
R2 is ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is dimethoxypyrimidinyl, dimethoxypyridinyl, dimethoxypyridazinyl, N-methylpyridonyl, N-methylpyrimidonyl, or methoxy-dimethylamino-pyrimidinyl,
and the enantiomers, as well as the salts, the N-oxides and the salts of the N-oxides of these compounds and enantiomers.

Compounds of formula I according to subaspect C5 of this invention to be more emphasized are those, in which
R1 is methoxy,
R2 is ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is 2,6-dimethoxy-pyrimidin-4-yl, 2,4-dimethoxy-pyrimidin-5-yl, 4,6-dimethoxy-pyrimidin-5-yl, 2,6- dimethoxy-pyridin-3-yl, 2,6-dimethoxy-pyridin-4-yl, 4,6-dimethoxy-pyridin-3-yl, 5,6-dimethoxy-pyridin-3-yl, 3,6-dimethoxy-pyridazin-4-yl, 1-methyl-1H-pyridin-2-one-5-yl, 1-methyl-1H-pyrimidin-2-one-5-yl, or 2-dimethylamino-4-methoxy-pyrimidin-5-yl,
and the enantiomers, as well as the salts, the N-oxides and the salts of the N-oxides of these compounds and enantiomers.

Further compounds of formula I according to aspect C in still more particular worthy to be mentioned in a sub-aspect (subaspect C6) are those, in which
R1 is methoxy or ethoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is substituted by R6 and R7 and R8, and is a pyridinyl, pyrimidinyl, pyrazinyl or pyridazinyl radical, in which
R6 is methoxy, or dimethylamino,
R7 is methoxy, or dimethylamino,
R8 is chlorine or methoxy,
and the enantiomers, as well as the salts, the N-oxides and the salts of the N-oxides of these compounds and enantiomers.

Particular compounds of formula I according to subaspect C6 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
either
Har is substituted by R6 and R7 and R8, and is pyridinyl, in which
R6 is methoxy,
R7 is methoxy,
R8 is chlorine,
or
Har is substituted by R6 and R7 and R8, and is pyrimidinyl, in which
R6 is methoxy,
R7 is methoxy,
R8 is methoxy,
or
Har is substituted by R6 and R7 and R8, and is pyrimidinyl, in which
R6 is dimethylamino,
R7 is dimethylamino,
R8 is chlorine,
and the enantiomers, as well as the salts, the N-oxides and the salts of the N-oxides of these compounds and enantiomers.

More particular compounds of formula I according to sub-aspect C6 of this invention are those, in which
R1 is methoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is 3-chloro-2,6-dimethoxy-pyridin-4-yl, 4-chloro-2,6-dimethoxy-pyridin-3-yl, 2,4,6-trimethoxy-pyrimidin-5-yl, or 5-chloro-2,6-bisdimethylamino-pyrimidin-4-yl,
and the enantiomers, as well as the salts, the N-oxides and the salts of the N-oxides of these compounds and enantiomers.

Further compounds of formula I according to aspect C in still more particular worthy to be mentioned in a sub-aspect (subaspect C7) are those, in which
R1 is methoxy or ethoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is unsubstituted, and is a pyridinyl, pyrimidinyl, pyrazinyl or pyridazinyl radical,
and the enantiomers, as well as the salts, the N-oxides and the salts of the N-oxides of these compounds and enantiomers.

Particular compounds of formula I according to subaspect C7 of this invention are those, in which
R1 is methoxy or ethoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is unsubstituted, and is pyridin-3-yl, pyridin-4-yl, pyrimidin-5-yl, or pyrazin-2-yl,
and the enantiomers, as well as the salts, the N-oxides and the salts of the N-oxides of these compounds and enantiomers.

More particular compounds of formula I according to sub-aspect C7 of this invention are those, in which
R1 is methoxy or ethoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is unsubstituted, and is pyridin-3-yl, pyridin-4-yl, pyrimidin-5-yl, or pyrazin-2-yl,
and the enantiomers, as well as the salts, the N-oxides and the salts of the N-oxides of these compounds and enantiomers.

Compounds of formula I according to aspect C to be emphasized in a sub-aspect (subaspect C8) are those, in which
R1 is methoxy or ethoxy,
R2 is methoxy, ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is any one selected from
pyridin-3-yl, pyridin-4-yl,
6-(morpholin-4-yl)-pyridin-3-yl, 6-(piperidin-1-yl)-pyridin-3-yl, 6-(pyrazol-1-yl)-pyridin-3-yl, 6-(imidazol-1-yl)-pyridin-3-yl, 6-methoxycarbonyl-pyridin-3-yl, 3-methoxycarbonyl-pyridin-2-yl,
2-methoxy-pyridin-3-yl, 6-methoxy-pyridin-3-yl,
2-methylsulfanyl-pyridin-3-yl,
6-hydroxy-pyridin-3-yl, 6-carboxy-pyridin-3-yl,
pyrimidin-5-yl,
2-methoxy-pyrimidin-5-yl, 2-dimethylamino-pyrimidin-5-yl, 2-methylsulfanyl-pyrimidin-5-yl, pyrazin-2-yl, 5-methyl-pyrazin-2-yl,
6-[2-(pyrrolidin-1-yl)-ethyl]-pyridin-3-yl,
2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl,
1-methyl-1H-pyridin-2-one-5-yl,
2,6-dimethoxy-pyrimidin-4-yl, 2,4-dimethoxy-pyrimidin-5-yl, 4,6-dimethoxy-pyrimidin-5-yl, 4-methyl-2-methylsulfanyl-pyrimidin-5-yl, 5-chloro-2-methylsulfanyl-pyrimidin-4-yl, 4-chloro-2-dimethylamino-pyrimidin-5-yl, 2-dimethylamino-4-methoxy-pyrimidin-5-yl, 1-methyl-1H-pyrimidin-2-one-5-yl,
3,6-dimethoxy-pyridazin-4-yl
4-chloro-2,6-dimethoxy-pyridin-3-yl, 3-chloro-2,6-dimethoxy-pyridin-4-yl, 5-chloro-2,6-bisdimethylamino-pyrimidin-4-yl, and
2,4,6-trimethoxy-pyrimidin-5-yl,
and the enantiomers, as well as the salts, the N-oxides and the salts of the N-oxides of these compounds and enantiomers.

Compounds of formula I according to aspect C to be more emphasized in a sub-aspect (subaspect C9) are those, in which
R1 is methoxy,
R2 is ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is any one selected from
pyridin-3-yl, pyridin-4-yl,
6-(morpholin-4-yl)-pyridin-3-yl, 6-(piperidin-1-yl)-pyridin-3-yl, 6-(pyrazol-1-yl)-pyridin-3-yl, 6-(imidazol-1-yl)-pyridin-3-yl,
6-methoxycarbonyl-pyridin-3-yl, 3-methoxycarbonyl-pyridin-2-yl,
2-methoxy-pyridin-3-yl, 6-methoxy-pyridin-3-yl,
2-methylsulfanyl-pyridin-3-yl,
6-hydroxy-pyridin-3-yl, 6-carboxy-pyridin-3-yl
pyrimidin-5-yl,
2-methoxy-pyrimidin-5-yl, 2-dimethylamino-pyrimidin-5-yl, 2-methylsulfanyl-pyrimidin-5-yl, pyrazin-2-yl, 5-methyl-pyrazin-2-yl,
2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl,
1-methyl-1H-pyridin-2-one-5-yl,
2,6-dimethoxy-pyrimidin-4-yl, 2,4-dimethoxy-pyrimidin-5-yl, 4,6-dimethoxy-pyrimidin-5-yl,
4-methyl-2-methylsulfanyl-pyrimidin-5-yl, 5-chloro-2-methylsulfanyl-pyrimidin-4-yl, 4-chloro-2-dimethylamino-pyrimidin-5-yl; 2-dimethylamino-4-methoxy-pyrimidin-5-yl, 1-methyl-1H-pyrimidin-2-one-5-yl,
3,6-dimethoxy-pyridazin-4-yl
4-chloro-2,6-dimethoxy-pyridin-3-yl, 3-chloro-2,6-dimethoxy-pyridin-4-yl, 5-chloro-2,6-bisdimethylamino-pyrimidin-4-yl, and
2,4,6-trimethoxy-pyrimidin-5-yl,
and the enantiomers, as well as the salts, the N-oxides and the salts of the N-oxides of these compounds and enantiomers.

Compounds of formula I according to aspect C to be in particular emphasized in a sub-aspect (subaspect C10) are those, in which
R1 is methoxy,
R2 is ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is any one selected from
6-(imidazol-1-yl)-pyridin-3-yl, pyrimidin-5-yl,
2-methoxy-pyrimidin-5-yl, 2-dimethylamino-pyrimidin-5-yl, 2-methylsulfanyl-pyrimidin-5-yl, 2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl,
1-methyl-1H-pyridin-2-one-5-yl,
2,6-dimethoxy-pyrimidin-4-yl, 2,4-dimethoxy-pyrimidin-5-yl, 4,6-dimethoxy-pyrimidin-5-yl,
2-dimethylamino-4-methoxy-pyrimidin-5-yl, 1-methyl-1H-pyrimidin-2-one-5-yl, and
3,6-dimethoxy-pyridazin-4-yl,
and the enantiomers, as well as the salts, the N-oxides and the salts of the N-oxides of these compounds and enantiomers.

Compounds of formula I according to aspect C to be in more particular emphasized in a sub-aspect (subaspect C11) are those, in which
R1 is methoxy,
R2 is ethoxy, difluoromethoxy or 2,2-difluoroethoxy,
R3 is hydrogen,
R31 is hydrogen,
R4 is —O—R41, in which
R41 is hydrogen,
R5 is hydrogen,
Har is any one selected from
6-(imidazol-1-yl)-pyridin-3-yl, pyrimidin-5-yl,
2-methoxy-pyrimidin-5-yl, 2-dimethylamino-pyrimidin-5-yl, 2-methylsulfanyl-pyrimidin-5-yl,
2,6-dimethoxy-pyridin-3-yl, 4,6-dimethoxy-pyridin-3-yl, 1-methyl-1H-pyridin-2-one-5-yl,
2,4-dimethoxy-pyrimidin-5-yl, 2-dimethylamino-4-methoxy-pyrimidin-5-yl, 1-methyl-1H-pyrimidin-2-one-5-yl, and 3,6-dimethoxy-pyridazin-4-yl,
and the enantiomers, as well as the salts, the N-oxides and the salts of the N-oxides of these compounds and enantiomers.

A special interest in the compounds according to this invention relates to those compounds which are included—within the meaning of this invention—by one or, when possible, by more of the following embodiments:

A special embodiment of the compounds of the present invention include those compounds of formula I in which R1 and R2 are independently 1-2C-alkoxy, 2,2-difluoroethoxy, or completely or predominantly fluorine-substituted 1-2C-alkoxy.

Another special embodiment of the compounds of the present invention include those compounds of formula I in which R1 and R2 are independently 1-2C-alkoxy, 2,2-difluoroethoxy, or completely or predominantly fluorine-substituted 1-2C-alkoxy, and R3 and R31 are both hydrogen.

Another special embodiment of the compounds of the present invention include those compounds of formula I in which one of R1 and R2 is methoxy, and the other is methoxy, ethoxy, difluoromethoxy or 2,2-difluoroethoxy, and R3 and R31 are both hydrogen.

Another special embodiment of the compounds of the present invention include those compounds of formula I in which R1 is ethoxy or, particularly, methoxy, and R2 is methoxy, or, particularly, ethoxy, difluoromethoxy or 2,2-difluoroethoxy, and R3 and R31 are both hydrogen.

Another special embodiment of the compounds of the present invention include those compounds of formula I in which R1 is methoxy, and R2 is methoxy, ethoxy, difluoromethoxy or 2,2-difluoroethoxy, and R3 and R31 are both hydrogen.

Another special embodiment of the compounds of the present invention include those compounds of formula I in which R1 is methoxy, and R2 is ethoxy, difluoromethoxy or 2,2-difluoroethoxy, and R3 and R31 are both hydrogen.

Another special embodiment of the compounds of the present invention include those compounds of formula I in which one of R1 and R2 is 2,2-difluoroethoxy, and the other is different from 2,2-difluoroethoxy, and R3 and R31 are both hydrogen.

Another special embodiment of the compounds of the present invention include those compounds of formula I in which R1 is ethoxy or, particularly, methoxy, and R2 is 2,2-difluoroethoxy, and R3 and R31 are both hydrogen.

Another special embodiment of the compounds of the present invention include those compounds of formula I in which R1 is methoxy, and R2 is 2,2-difluoroethoxy, and R3 and R31 are both hydrogen.

Another special embodiment of the compounds of the present invention include those compounds of formula I in which R1 is methoxy, and R2 is ethoxy, and R3 and R31 are both hydrogen.

Another special embodiment of the compounds of the present invention include those compounds of formula I in which R1 is methoxy, and R2 is difluoromethoxy, and R3 and R31 are both hydrogen.

Another special embodiment of the compounds of the present invention include those compounds of formula I, in which R5 or, particularly, R4 is the radical (1-4C-alkylcarbonyl)-O— such as e.g. acetoxy, or hydroxyl, and all the other substituents are as defined in any compound which is said to be mentioned above in aspect A or B or C, or in any one of the sub-aspects thereof.

Another special embodiment of the compounds of the present invention include those compounds of formula I in which R5 or, particularly, R4 is hydroxyl.

Another special embodiment of the compounds of the present invention include those compounds of formula I, in which Har is optionally substituted by R6 and/or R7 and/or R8, and is
a 9- or 10-membered fused bicyclic partially saturated heteroaryl radical comprising a benzene ring and 1 or 2 heteroatoms independently selected from the group consisting of oxygen, nitrogen and sulphur, or
a 9- or 10-membered fused bicyclic unsaturated heteroaryl radical comprising 1 to 4, particularly 1, 2 or 3, heteroatoms independently selected from the group consisting of oxygen, nitrogen and sulphur, or
a 6-membered monocyclic unsaturated heteroaryl radical comprising 1 to 3, particularly 1 or 2, nitrogen atoms, or
a 5-membered monocyclic unsaturated heteroaryl radical comprising 1 to 4, particularly 1, 2 or 3, heteroatoms independently selected from the group consisting of oxygen, nitrogen and sulphur,
in which
R6 is halogen, 1-4C-alkyl, 1-4C-alkoxy, cyano, oxo, 1-4C-alkoxycarbonyl, pyridyl, morpholino, piperidino, imidazol-1-yl or pyrazol-1-yl,
R7 is 1-4C-alkyl or 1-4C-alkoxy,
R8 is halogen, 1-4C-alkyl or 1-4C-alkoxy.

Another special embodiment of the compounds of the present invention include those compounds of formula I, in which Har is
benzo[1,4]dioxanyl, benzo[1,3]dioxolyl or 2,2-difluoro-benzo[1,3]dioxolyl;
quinolinyl, benzofurazanyl, benzothiazolyl, 1-methyl-1H-benzotriazolyl or 4-methoxy-1,3-dimethyl-1H-pyrazolo[3,4-b]pyridinyl; or
pyridinyl, pyrimidinyl, pyrazinyl, 5-methyl-pyrazinyl, isoxazolyl, 1-methyl-imidazolyl, 2-(pyridinyl)-thiazolyl,
2,6-dimethoxy-pyridinyl, 2-methoxy-pyridinyl,
6-(methoxycarbonyl)-pyridinyl, 5-(methoxycarbonyl)-pyridinyl,
2,6-dimethoxypyrimidinyl, 2-methoxy-pyrimidinyl, 2,4,6-trimethoxy-pyrimidinyl, 2,4-dimethoxy-pyrimidinyl,
6-(morpholin-4-yl)-pyridinyl, 6-(piperidin-1-yl)-pyridinyl, 6-(pyrazol-1-yl)-pyridinyl, 6-(imidazol-1-yl)-pyridinyl, or
3-chloro-2,6-dimethoxy-pyridinyl.

Another special embodiment of the compounds of the present invention include those compounds of formula I, in which Har is
benzo[1,4]dioxan-6-yl, benzo[1,3]dioxol-5-yl or 2,2-difluoro-benzo[1,3]dioxol-5-yl;
quinolin-6-yl, benzofurazan-5-yl, benzothiazol-6-yl, 1-methyl-1H-benzotriazol-5-yl or 4-methoxy-1,3-dimethyl-1H-pyrazolo[3,4-b]pyridin-5-yl; or
pyridin-3-yl, pyridin-4-yl, pyrimidin-5-yl, pyrazin-2-yl, 5-methyl-pyrazin-2-yl, isoxazol-5-yl, 1-methyl-imidazol-2-yl, 1-methyl-imidazol-5-yl, 2-(pyridin-3-yl)-thiazol-4-yl,
2,6-dimethoxy-pyridin-4-yl, 2,6-dimethoxy-pyridin-3-yl, 2-methoxy-pyridin-3-yl,
6-(methoxycarbonyl)-pyridin-3-yl, 5-(methoxycarbonyl)-pyridin-2-yl,
2,6-dimethoxypyrimidin-4-yl, 2-methoxy-pyrimidin-5-yl, 2,4,6-trimethoxy-pyrimidin-5-yl, 2,4-dimethoxy-pyrimidin-5-yl, 2,6-dimethoxy-pyrimidin-4-yl,
6-(morpholin-4-yl)-pyridin-3-yl, 6-(piperidin-1-yl)-pyridin-3-yl, 6-(pyrazol-1-yl)-pyridin-3-yl, 6-(imidazol-1-yl)-pyridin-3-yl, or
3-chloro-2,6-dimethoxy-pyridin-4-yl.

Another special embodiment of the compounds of the present invention include those compounds of formula I, in which Har is optionally substituted by R6 and/or R7 and/or R8, and is pyridinyl, pyrazinyl, pyridazinyl or pyrimidinyl, in which R6, R7, R8 and all the other substituents are as defined in any compound which is disclosed herein, such as e.g. any compound which is said to be mentioned above in aspect A or B or C, or in any One of the sub-aspects thereof.

Another special embodiment of the compounds of the present invention include those compounds of formula I, in which Har is optionally substituted by R6 and/or R7 and/or R8, and is pyridinyl, in which R6, R7, R8 and all the other substituents are as defined in any compound which is disclosed herein.

Another special embodiment of the compounds of the present invention include those compounds of formula I, in which
Har is substituted by R6 and R7 and R8, or
Har is substituted by R6 and R7, or
Har is substituted by R6 and R8, or
Har is substituted by R7 and R8, and is pyridinyl, in which R6, R7, R8 and all the other substituents are as defined in any compound which is disclosed herein.

Another special embodiment of the compounds of the present invention include those compounds of formula I, in which Har is substituted by R6 and R7, and is pyridinyl, in which R6 and R7 and all the other substituents are as defined in any compound which is disclosed herein.

Another special embodiment of the compounds of the present invention include those compounds of formula I, in which Har is optionally substituted by R6 and/or R7 and/or R8, and is pyrimidinyl, in which R6, R7, R8 and all the other substituents are as defined in any compound which is disclosed herein.

Another special embodiment of the compounds of the present invention include those compounds of formula I; in which Har is optionally substituted by R6 and/or R7, and is pyrimidinyl or pyridazinyl, in which R6 and R7 and all the other substituents are as defined in any compound which is disclosed herein.

Another special embodiment of the compounds of the present invention include those compounds of formula I, in which R6 and/or R7 is an oxo group.

Another special embodiment of the compounds of the present invention include those compounds of formula I, in which Har is pyridinyl, pyrimidinyl, pyrazinyl or pyridazinyl, each of which is substituted by R6 and/or R7 and/or R8, in which R6 or R7 is an oxo group, and one of the other substituents is 1-4C-alkyl, e.g. methyl, bonded to a ring nitrogen atom to form a cyclic amide structure.

Another special embodiment of the compounds of the present invention include those compounds of formula I, in which R6 and/or R7 is a 1-4C-alkylthio, such as e.g. methylthio, group.

Another special embodiment of the compounds of the present invention include those compounds of formula I, in which R6 is -A-N(R61)R62, in which A is a bond, and R61 and R62 together and with inclusion of the nitrogen atom to which they are attached, form a heterocyclic ring Het1, particularly Het1 according to facet 2, such as e.g. pyrrol-1-yl, triazol-1-yl or, especially, pyrazol-1-yl or imidazol-1-yl.

Another special embodiment of the compounds of the present invention include those compounds of formula I, in which A is a bond.

Another special embodiment of the compounds of the present invention include those compounds of formula I, in which Har is substituted by R6 and/or R7, and is pyridinyl, in which, R6 is 1-4C-alkoxy, 1-4C-alkoxycarbonyl or carboxyl,
R7 is 1-4C-alkoxy.

Another special embodiment of the compounds of the present invention include those compounds of formula I, in which either Har is N-methyl-pyridonyl or N-methyl-pyrimidonyl, or Har is substituted by R6, and is pyridinyl or pyrimidinyl, in which R6 is imidazol-1-yl-pyridinyl, pyrazol-1-yl-pyridinyl, methylthio, methoxy, ethoxy, dimethylamino, or Har is substituted by R6 and R7, and is pyridinyl, pyrimidinyl or pyridazinyl, in which R6 is methoxy, ethoxy or dimethylamino, and
R7 is methoxy or ethoxy.

Another special embodiment of the compounds of the present invention include those compounds of formula I, in which Har is either N-methyl-pyrid-2-onyl or N-methyl-pyrimid-2-onyl,
or imidazol-1-yl-pyridinyl or pyrazol-1-yl-pyridinyl,
or methylthio-pyrimidinyl, methoxy-pyrimidinyl, dimethylamino-pyrimidinyl or pyrimidinyl, or Har is substituted by R6 and R7, and is pyridinyl, in which
R6 is methoxy or ethoxy, and
R7 is methoxy or ethoxy, or Har is substituted by R6 and R7, and is pyrimidinyl or pyridazinyl, in which
R6 is methoxy, ethoxy or dimethylamino, and
R7 is methoxy or ethoxy.

Another special embodiment of the compounds of the present invention include those compounds of formula I, in which Har is pyridinyl bisubstituted by 1-4C-alkoxy, such as, for example, 2,6-dimethoxypyridinyl (e.g. 2,6-dimethoxypyridin-3-yl).

A preferred embodiment according to the present invention is embodiment a.

A further preferred embodiment of the compounds of the present invention include compounds according to embodiment a, in which R5 and R41 are both hydrogen, and in which R1 and R2 are independently 1-2C-alkoxy, 2,2-difluoroethoxy, or completely or predominantly fluorine-substituted 1-2-C-alkoxy, and R3 and R31 are hydrogen.

A yet further preferred embodiment of the compounds of the present invention include compounds according to embodiment a, in which R5 is hydrogen, and in which R1 is methoxy, and R2 is ethoxy, difluoromethoxy or 2,2-difluoroethoxy, and R3 and R31 are both hydrogen.

A still yet further preferred embodiment of the compounds of the present invention include compounds according to embodiment a, in which R5 and R41 are both hydrogen, and in which R1 is methoxy, and R2 is ethoxy, difluoromethoxy or 2,2-difluoroethoxy, and R3 and R31 are both hydrogen.

Another preferred embodiment according to the present invention is aspect C.

In this context, a special embodiment of the compounds of the present invention include those compounds of formula I, in which Har is pyridinyl substituted by R6 and R7, in which
R6 is 1-4C-alkoxy, particularly methoxy or ethoxy,
R7 is 1-4C-alkoxy, particularly methoxy or ethoxy,
such as, for example, dimethoxy-pyridinyl or ethoxy-(methoxy-)pyridinyl, e.g. dimethoxy-pyridin-3-yl or dimethoxy-pyridin-4-yl or ethoxy-(methoxy-)pyridine-3-yl, like 2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, or 5-ethoxy-6-methoxy-pyridin-3-yl.

A further special embodiment of the compounds of the present invention include those compounds of formula I, in which Har is pyrimidinyl monosubstituted by 1-4C-alkoxy, particularly methoxy or ethoxy, such as, for example, methoxy-pyrimidinyl, e.g. methoxy-pyrimidin-5-yl, like 2-methoxy-pyrimidin-5-yl.

A further special embodiment of the compounds of the present invention include those compounds of formula I, in which Har is pyrimidinyl monosubstituted by di-1-4C-alkylamino, particularly di-1-2C-alkylamino, such as, for example, dimethylamino-pyrimidinyl, e.g. dimethylamino-pyrimidin-5-yl, like 2-dimethylamino-pyrimidin-5-yl.

A further special embodiment of the compounds of the present invention include those compounds of formula I, in which Har is pyrimidinyl substituted by R6 and R7, in which R6 is 1-4C-alkoxy, particularly methoxy or ethoxy,
R7 is 1-4C-alkoxy, particularly methoxy or ethoxy,
such as, for example, dimethoxy-pyrimidinyl, e.g. dimethoxy-pyrimidin-5-yl or dimethoxy-pyrimidin-4-yl, like 2,6-dimethoxy-pyrimidin-4-yl, 2,4-dimethoxy-pyrimidin-5-yl, or 4,6-dimethoxy-pyrimidin-5-yl.

A further special embodiment of the compounds of the present invention include those compounds of formula I, in which Har is pyridazinyl substituted by R6 and R7, in which R6 is 1-4C-alkoxy, particularly methoxy or ethoxy,
R7 is 1-4C-alkoxy, particularly methoxy or ethoxy,
such as, for example, dimethoxy-pyridazinyl, e.g. dimethoxy-pyridazin-4-yl, like 3,6-dimethoxy-pyridazin-4-yl.

A further special embodiment of the compounds of the present invention include those compounds of formula I, in which Har is pyrimidinyl substituted by R6 and R7, in which R6 is 1-2C-alkoxy, particularly methoxy,
R7 is di-1-2C-alkylamino, particularly dimethylamino,
such as, for example, methoxy-(dimethylamino-)pyrimidinyl, e.g. methoxy-(dimethylamino-)pyrimidin-5-yl, like 4-methoxy-2-dimethylamino-pyrimidin-5-yl.

A further special embodiment of the compounds of the present invention include those compounds of formula I, in which Har is N-(1-4C-alkyl)-pyridonyl, such as, for example, N-methyl-pyridonyl, e.g. 1-methyl-1H-pyridin-2-onyl, like 1-methyl-1H-pyridin-2-one-5-yl (i.e. 1-methyl-6-oxo-1H-pyridin-3-yl).

A further special embodiment of the compounds of the present invention include those compounds of formula I, in which Har is N-(1-4C-alkyl)-pyrimidonyl, such as, for example, N-methyl-pyrimidonyl, e.g. 1-methyl-1H-pyrimidin-2-onyl, like 1-methyl-1H-pyrimidin-2-one-5-yl (i.e. 1-methyl-2-oxo-1H-pyrimidin-5-yl).

A further special embodiment of the compounds of the present invention include those compounds of formula I, in which Har is pyridinyl substituted by two methoxy radicals, such as, for example, 2,6-dimethoxy-pyridin-3-yl.

Another special embodiment of the compounds of the present invention include those compounds of formula I, in which Har is pyrimidinyl substituted by two methoxy radicals, such as; for example, 2,4-dimethoxy-pyrimidin-5-yl.

A further special embodiment of the compounds of the present invention include those compounds of formula I, in which Har is pyrimidinyl monosubstituted by methoxy, such as, for example, 2-methoxy-pyrimidin-5-yl.

A further special embodiment of the compounds of the present invention include those compounds of formula I, in which Har is pyridazinyl substituted by two methoxy radicals, such as, for example, 3,6-dimethoxy-pyridazin-4-yl.

A further special embodiment of the compounds of the present invention include those compounds of formula I, in which Har is
pyridin-3-yl, pyridin-4-yl,
6-(morpholin-4-yl)-pyridin-3-yl, 6-(piperidin-1-yl)-pyridin-3-yl, 6-(pyrazol-1-yl)-pyridin-3-yl, 6-(imidazol-1-yl)-pyridin-3-yl,
6-methoxycarbonyl-pyridin-3-yl, 3-methoxycarbonyl-pyridin-2-yl,
2-methoxy-pyridin-3-yl, 6-methoxy-pyridin-3-yl,
2-methylsulfanyl-pyridin-3-yl,
6-hydroxy-pyridin-3-yl, 6-carboxy-pyridin-3-yl, pyrimidin-5-yl,
2-methoxy-pyrimidin-5-yl, 2-dimethylamino-pyrimidin-5-yl, 2-methylsulfanyl-pyrimidin-5-yl, pyrazin-2-yl, 5-methyl-pyrazin-2-yl,
6-[2-(pyrrolidin-1-yl)-ethyl]-pyridin-3-yl,
2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl,
1-methyl-1H-pyridin-2-one-5-yl,
2,6-dimethoxy-pyrimidin-4-yl, 2,4-dimethoxy-pyrimidin-5-yl, 4,6-dimethoxy-pyrimidin-5-yl,
4-methyl-2-methylsulfanyl-pyrimidin-5-yl, 5-chloro-2-methylsulfanyl-pyrimidin-4-yl, 4-chloro-2-dimethylamino-pyrimidin-5-yl, 2-dimethylamino-4-methoxy-pyrimidin-5-yl, 1-methyl-1H-pyrimidin-2-one-5-yl,
3,6-dimethoxy-pyridazin-4-yl,
4-chloro-2,6-dimethoxy-pyridin-3-yl, 3-chloro-2,6-dimethoxy-pyridin-4-yl, 5-chloro-2,6-bisdimethylamino-pyrimidin-4-yl, or
2,4,6-trimethoxy-pyrimidin-5-yl.

A yet further special embodiment of the compounds of the present invention include those compounds of formula I, in which Har is
6-(imidazol-1-yl)-pyridin-3-yl, pyrimidin-5-yl,
2-methoxy-pyrimidin-5-yl, 2-dimethylamino-pyrimidin-5-yl, 2-methylsulfanyl-pyrimidin-5-yl,
2,6-dimethoxy-pyridin-3-yl, 2,6-dimethoxy-pyridin-4-yl, 4,6-dimethoxy-pyridin-3-yl, 5,6-dimethoxy-pyridin-3-yl, 4,6-diethoxy-pyridin-3-yl, 5-ethoxy-6-methoxy-pyridin-3-yl,
1-methyl-1H-pyridin-2-one-5-yl,
2,6-dimethoxy-pyrimidin-4-yl, 2,4-dimethoxy-pyrimidin-5-yl, 4,6-dimethoxy-pyrimidin-5-yl,
2-dimethylamino-4-methoxy-pyrimidin-5-yl, 1-methyl-1H-pyrimidin-2-one-5-yl,
3,6-di methoxy-pyridazin-4-yl.

A still yet further special embodiment of the compounds of the present invention include those compounds of formula I, in which Har is
6-(imidazol-1-yl)-pyridin-3-yl, pyrimidin-5-yl,
2-methoxy-pyrimidin-5-yl, 2-dimethylamino-pyrimidin-5-yl, 2-methylsulfanyl-pyrimidin-5-yl,
2,6-dimethoxy-pyridin-3-yl, 4,6-dimethoxy-pyridin-3-yl, 1-methyl-1H-pyridin-2-one-5-yl,
2,4-dimethoxy-pyrimidin-5-yl, 2-dimethylamino-4-methoxy-pyrimidin-5-yl, 1-methyl-1H-pyrimidin-2-one-5-yl, or 3,6-dimethoxy-pyridazin-4-yl.

Suitable compounds according to the present invention more worthy to be mentioned include those compounds of formula I, in which R5 or, particularly, R4 is hydroxyl.

Exemplary compounds according to the present invention may include, without being restricted thereto, compounds selected from the group consisting of those compounds mentioned in the following examples as final compounds, particularly those embodimental examples which are from formula I according to embodiment a, in which R3, R31, R41 and R5 are all hydrogen, and/or those compounds listed in the Table A in the appended "Biological Investigations", the enantiomers, as well as the salts, the N-oxides and the salts of the N-oxides of these compounds and enantiomers.

Preferably, any or all of those compounds of formula I according to embodiment a, in which R3, R31, R41 and R5 are all hydrogen, which are described by way of example as final compounds in the following examples and, particularly, the enantiomers thereof, particularly those having the formula Ia*****, as well as the salts of these compounds and enantiomers, are to be mentioned as a particular interesting aspect of the present invention.

The compounds of formula I are chiral compounds having chiral centers at least in positions 4a and 10b and depending on the meanings of R3, R31, R4 and R5 additional chiral centers in positions 1, 2, 3 and 4.

Numbering

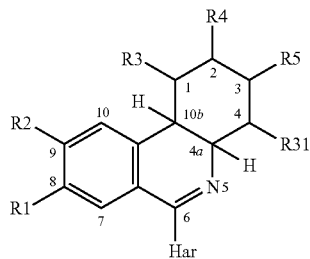

(I)

The invention includes all conceivable stereoisomers in pure form as well as in any mixing ratio. Preference is given to compounds of formula I in which the hydrogen atoms in positions 4a and 10b are in the cis position relative to one another. The pure cis enantiomers and their mixtures in any mixing ratio and including the racemates are more preferred in this context.

Particularly preferred in this context are those compounds of formula I, which have with respect to the positions 4a and 10b the configuration shown in formula (I*):

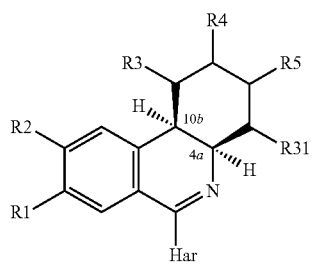

(I*)

If, for example, in compounds of formula I* R3, R31 and R5 have the meaning hydrogen and R4 has the meaning —OR41, then the configuration—according to the rules of Cahn, Ingold and Prelog—is R in the 4a position and R in the 10b position.

Further preferred compounds of the formula I according to embodiment a are those which have, with respect to the positions 2, 4a and 10b, the same configuration as shown in the formulae Ia and Ia* and Ia****:

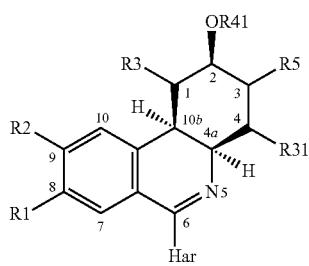

(Ia**)

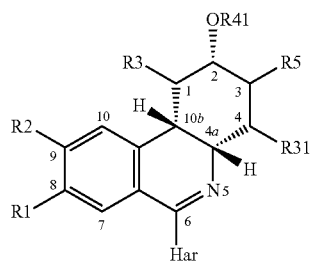

(Ia***)

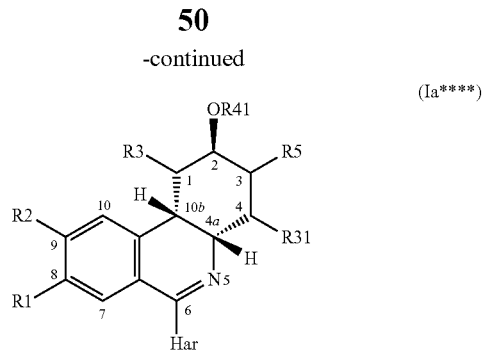

(Ia****)

If, for example in compounds of the formula Ia** R3, R31 and R5 have the meaning hydrogen, then the configuration—according the rules of Cahn, Ingold and Prelog—is S in the position 2, R in the position 4a and R in the position 10b.

If for example in compounds of the formula Ia*** R3, R31 and R5 have the meaning hydrogen, then the configuration—according the rules of Cahn, Ingold and Prelog—is R in the position 2, S in the position 4a and S in the position 10b.

If, for example in compounds of the formula Ia**** R3, R31 and R5 have the meaning hydrogen, then the configuration—according the rules of Cahn, Ingold and Prelog—is S in the position 2, S in the position 4a and S in the position 10b.

In more particular preferred compounds of the formula I according embodiment a are those which have, with respect to the positions 2, 4a and 10b, the same configuration as shown in the formula Ia*****:

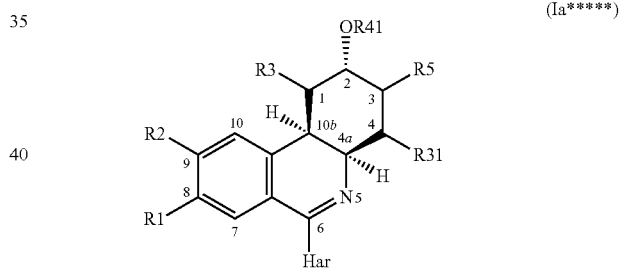

(Ia*****)

If, for example in compounds of the formula Ia***** R3, R31 and R5 have the meaning hydrogen, then the configuration—according the rules of Cahn, Ingold and Prelog—is R in the position 2, R in the position 4a and R in the position 10b.

Preferred compounds of the formula I according to embodiment b are those which have, with respect to the positions 3, 4a and 10b, the same configuration as shown in the formulae Ib and Ib* and Ib****:

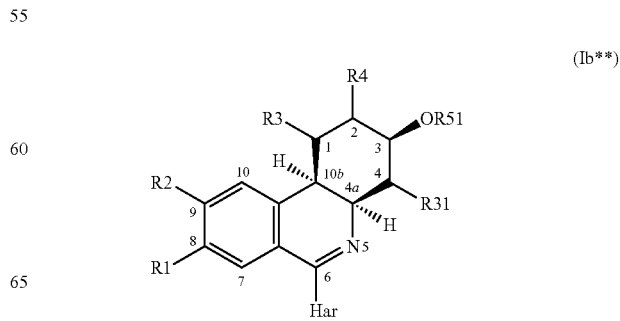

(Ib**)

compounds having a free amino group such as starting compounds of formulae IVa or VIIb as defined below.

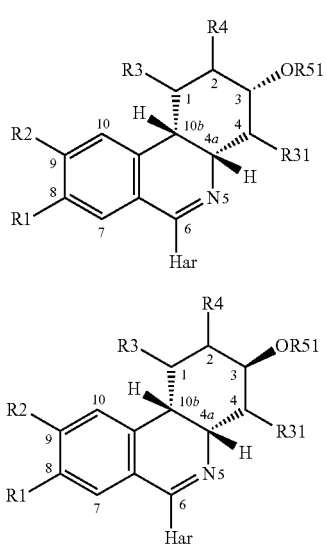

(Ib***)

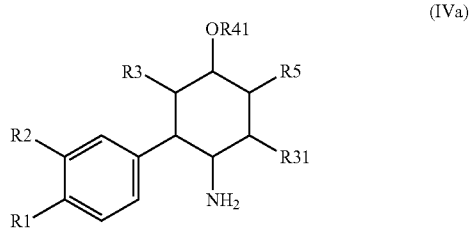

(IVa)

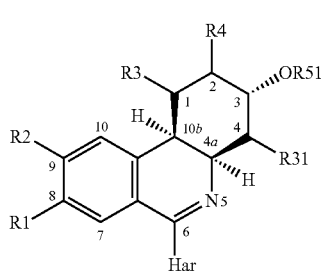

(Ib****)

If, for example in compounds of the formula Ib** R3, R31 and R5 have the meaning hydrogen, then the configuration—according the rules of Cahn, Ingold and Prelog—is R in the position 3, R in the position 4a and R in the position 10b.

If, for example in compounds of the formula Ib*** R3, R31 and R6 have the meaning hydrogen, then the configuration—according the rules of Cahn, Ingold and Prelog—is S in the position 3, S in the position 4a and S in the position 10b.

If, for example in compounds of the formula Ib*** R3, R31 and R5 have the meaning hydrogen, then the configuration—according the rules of Cahn, Ingold and Prelog—is R in the position 3, S in the position 4a and S in the position 10b.

More preferred compounds of the formula I according to embodiment b are those which have, with respect to the positions 3, 4a and 10b, the same configuration as shown in the formula Ib*****:

(Ib*****)

If, for example in compounds of the formula Ib***** R3, R31 and R5 have the meaning hydrogen, then the configuration—according the rules of Cahn, Ingold and Prelog—is S in the position 3, R in the position 4a and R in the position 10b.

Within the meaning of the embodiments a and b according to this invention, compounds of formula Ia***** are in particular to be emphasized.

The enantiomers can be separated in a manner known per se (for example by preparation and separation of appropriate diastereoisomeric compounds). Thus, e.g. an enantiomer separation can be carried out at the stage of the starting compounds having a free amino group such as starting compounds of formulae IVa or VIIb as defined below.

Separation of the enantiomers can be carried out, for example, by means of salt formation of the racemic compounds of the formulae IVa or VIIb with optically active acids, preferably carboxylic acids, subsequent resolution of the salts and release of the desired compound from the salt. Examples of optically active carboxylic acids which may be mentioned in this connection are the enantiomeric forms of mandelic acid, tartaric acid, O,O'-dibenzoyltartaric acid, camphoric acid, quinic acid, glutamic acid, pyroglutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid. Alternatively, enantiomerically pure starting compounds of the formulae IVa or VIIb can be prepared via asymmetric syntheses. Enantiomerically pure starting compounds as well as enantiomerically pure compounds of the formula I can be also obtained by chromatographic separation on chiral separating columns; by derivatization with chiral auxiliary reagents, subsequent diastereomer separation and removal of the chiral auxiliary group; or by (fractional) crystallization from a suitable solvent.

The compounds according to the invention can be prepared, for example, as shown in the reaction schemes below and according to the following specified reaction steps, or, particularly, in a manner as described by way of example in the following examples, or analogously or similarly thereto according to preparation procedures or synthesis strategies known to the person skilled in the art.

Compounds of formula I, in which R1, R2, R3, R31, R4, R5 and Har have the meanings mentioned above, according to embodiment a or b (i.e. compounds of formulae Ia or Ib, respectively) can be obtained as described as follows.

Compounds of formula Ia according to embodiment a, in which R1, R2, R3, R31, R41, R5 and Har have the meanings mentioned above in embodiment a whereby R41 is other than hydrogen, can be prepared as described and shown in reaction scheme 1 below.

In the first reaction step of the synthesis route shown in scheme 1, compounds of the formula Va, in which R1, R2, R3, R31, R41 and R5 have the meanings mentioned above in embodiment a whereby R41 is other than hydrogen, are prepared from the corresponding compounds of the formula VIa by introduction of the group R41 whereby R41 is other than hydrogen. The introduction reaction is carried out in a manner habitual per se for an etherification or esterification reaction, or as described by way of example in the following examples.

Reaction scheme 1:

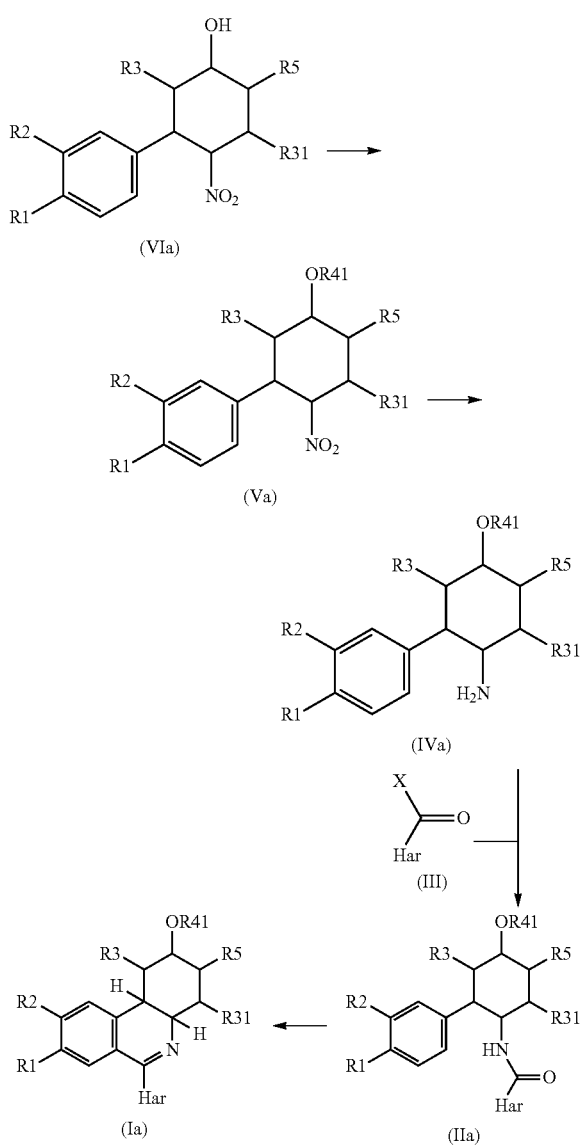

In the next reaction step of the synthesis route shown in reaction scheme 1, the nitro group of compounds of the formula Va, in which R1, R2, R3, R31, R41 and R5 have the meanings mentioned above in embodiment a whereby R41 is other than hydrogen, is reduced to the amino group of the corresponding compounds of the formula IVa. Said reduction is carried out in a manner known to the person skilled in the art, for example as described in J. Org. Chem. 1962, 27, 4426 or as described in the following examples. In more detail, the reduction can be carried out, for example, by catalytic hydrogenation, e.g. in the presence of Raney nickel or a noble metal catalyst such as palladium on active carbon, in a suitable solvent such as methanol or ethanol at room temperature and under normal or elevated pressure. Optionally, a catalytic amount of an acid, such as, for example, hydrochloric acid, can be added to the solvent. Preferably, however, the reduction is carried out using a hydrogen-producing mixture, for example, metals such as zinc, zinc-copper couple or iron with organic acids such as acetic acid or mineral acids such as hydrochloric acid. More preferably, the reduction is carried out using a zinc-copper couple in the presence of an organic or an inorganic acid. Such a zinc-copper couple is accessible in a way known to the person of ordinary skill in the art.

Compounds of the formula IVa, in which R1, R2, R3, R31, R41 and R5 have the meanings indicated above in embodiment a whereby R41 is other than hydrogen and which are sensitive against catalytic hydrogenation, can be prepared from the corresponding compounds of the formula Va by selective reduction of the nitro group in a manner known to the person skilled in the art, for example by hydrogen transfer reaction in the presence of a metal catalyst, for example palladium or, preferably, Raney nickel, in a lower alcohol as solvent using, for example, ammonium formiate or, preferably, hydrazine hydrate as hydrogen donor.

Compounds of the formula IIa, in which R1, R2, R3, R31, R41, R5 and Har have the meanings indicated above in embodiment a whereby R41 is other than hydrogen, are accessible from the corresponding compounds of the formula IVa by reaction with corresponding compounds of the formula III, in which X represents a suitable leaving group, preferably a chlorine atom.

Alternatively, compounds of the formula IIa can also be prepared from the corresponding compounds of the formula IVa and corresponding compounds of the formula III, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N, N,N', N'-tetramethyluronium tetrafluoroborate or O-(benzotriazol-1yl)-N,N,N',N'-tetramthyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

Compounds of the formula III are either known or can be prepared in a known manner.

Compounds of the formula Ia, in which R1, R2, R3, R31, R41, R5 and Har have the meanings mentioned in embodiment a whereby R41 is other than hydrogen, can be obtained by cyclocondensation of corresponding compounds of the formula IIa.

Said cyclocondensation reaction is carried out in a manner known per se to the person skilled in the art or as described by way of example in the following examples, according to Bischler-Napieralski (e.g. as described in J. Chem. Soc., 1956, 4280-4282) in the presence of a suitable condensing agent, such as, for example, polyphosphoric acid, phosphorus pentachloride, phosphorus pentoxide or phosphorus oxychloride, in a suitable inert solvent, e.g. in a chlorinated hydrocarbon such as chloroform, or in a cyclic hydrocarbon such as toluene or xylene, or another inert solvent such as isopropyl acetate or acetonitrile, or without further solvent using an excess of condensing agent, at reduced temperature, or at room temperature, or at elevated temperature or at the boiling temperature of the solvent or condensing agent used. If necessary, said cyclocondensation reaction can be carried out in the presence of one or more suitable Lewis Acids such as, for example, suitable metal halogenides (e.g. chlorides) or sulphonates (e.g. triflates), including rare earth metal salts, such as e.g. anhydrous aluminum tri-chloride, aluminum tribromide, zinc chloride, boron trifluoride ethereate, titanium tetrachloride or, in particular, tin tetrachloride, and the like.

Parallel to the cyclization in the presence of a chlorine-containing condensing agent (such as e.g. phosphorus pentachloride), a nucleophilic or electrophilic substitution of the Har moiety giving the corresponding chlorine substituted Har moiety can take place, especially in the case of electron rich Har groups, such as e.g. the dimethoxypyridinyl radical, like the 2,6-dimethoxypyridin-4-yl or the 2,6-dimethoxy-pyridin-3-yl radical, an electrophilic substitution can take place, and especially in the case of Har radicals incorporating cyclic amide structures (e.g. NH-pyridones or NH-pyrimidones) a nucleophilic substitution of the oxo group can take place.

Below reaction scheme 2 shows the synthesis of compounds of the formula VIa, in which R1, R2, R3, R31 and R5 have the meanings indicated above in embodiment a, from corresponding compounds of the formula VIIa via reduction reaction of the carbonyl group. Suitable reducing agents for the abovementioned reduction reaction may include, for example, metal hydride compounds such as, for example, diisopropylaluminium hydride, borane, sodium borohydride, sodium triacetoxyborohydride, sodium cyanoborohydride, zinc borohydride, potassium tri-sec-butylborohydride, sodium tri-sec-butylborohydride, lithium td-sec-butylborohydride, β-isopinocampheyl-9-borabicyclo[3.3.1]nonane and the like. The preferred examples of said reducing agents are sodium cyanoborohydride, 3-isopinocampheyl-9-borabicyclo[3.3.1]nonane and potassium tri-sec-butylborohydride. The most preferred examples of the abovementioned reducing agents are p-isopinocampheyl-9-borabicyclo[3.3.1]nonane and potassium tri-sec-butylborohydride, which both allow to prepare compounds of the formula VIa stereoselectively. "Stereoselectively" in this connection means that those compounds of the formula VIa, in which the hydrogen atoms in positions 1 and 3 are located at the opposite side of the plane defined by the cyclohexane ring, are obtained preferentially.

The compounds of the formula VIIa, in which R1, R2, R3, R31 and R5 have the meanings mentioned in embodiment a, are either known or can be obtained by the reaction of compounds of the formula IXa, in which R1 and R2 have the meanings mentioned above, with compounds of the formula VIIIa, in which R3, R31 and R5 have the meanings mentioned above in embodiment a. The cycloaddition reaction is carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formulae VIa or Va, in which the phenyl ring and the nitro group are trans to one another, can be converted in a manner known to the person skilled in the art into the corresponding cis compounds, e.g. as described in J. Amer. Chem. Soc. 1957, 79, 6559 or as described in the following examples.

The compounds of the formulae VIIIa and IXa are either known or can be prepared in a known manner. The compounds of the formula IXa can be prepared, for example, in a manner known to the person skilled in the art from corresponding compounds of the formula Xa as described, for example, in J. Chem. Soc. 1951, 2524 or in J. Org. Chem. 1944, 9, 170 or as described in the following examples.

The compounds of the formula Xa, in which R1 and R2 have the meanings indicated above in embodiment a, are either known or can be prepared in a manner known to the person skilled in the art, as described, for example, in Ber. Dtsch. Chem. Ges. 1925, 58, 203.

Compounds of formula Ib according to embodiment b, in which R1, R2, R3, R31, R4, R51 and Har have the meanings indicated above in embodiment b whereby R51 is other than hydrogen, can be prepared as described and shown in reaction scheme 3 below.

In the first reaction step in reaction scheme 3, the nitro group of compounds of the formula VIIIb, in which R1, R2, R3, R31 and R4 have the meanings indicated in embodiment b above, is reduced to obtain corresponding compounds of the formula VIIb. Said reduction reaction is carried out in a manner known to the person skilled in the art, for example as described in J. Org. Chem. 1962, 27, 4426 or as described in the following examples. More specifically, the reduction can be carried out, for example, by contacting compounds of the formula VIIIb with a hydrogen-producing mixture such as, preferably, metallic zinc in a mildly acidic medium such as acetic acid in a lower alcohol such as methanol or ethanol at room temperature or at elevated temperature or, preferably, at the boiling temperature of the solvent mixture. Alternatively, the reduction can be carried out by selective reduction of the nitro group in a manner known to the person skilled in the art, for example by hydrogen transfer reaction in the presence of a metal catalyst, for example palladium or preferably Raney nickel, in a suitable solvent, preferably a lower alcohol, using, for example ammonium formiate or preferably hydrazine hydrate as hydrogen donor.

Reaction scheme 2:

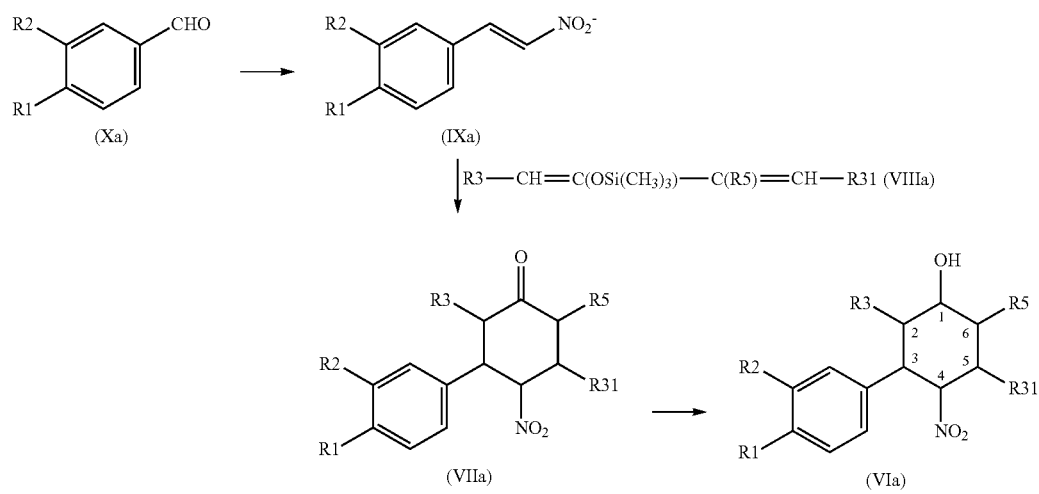

Reaction scheme 3:

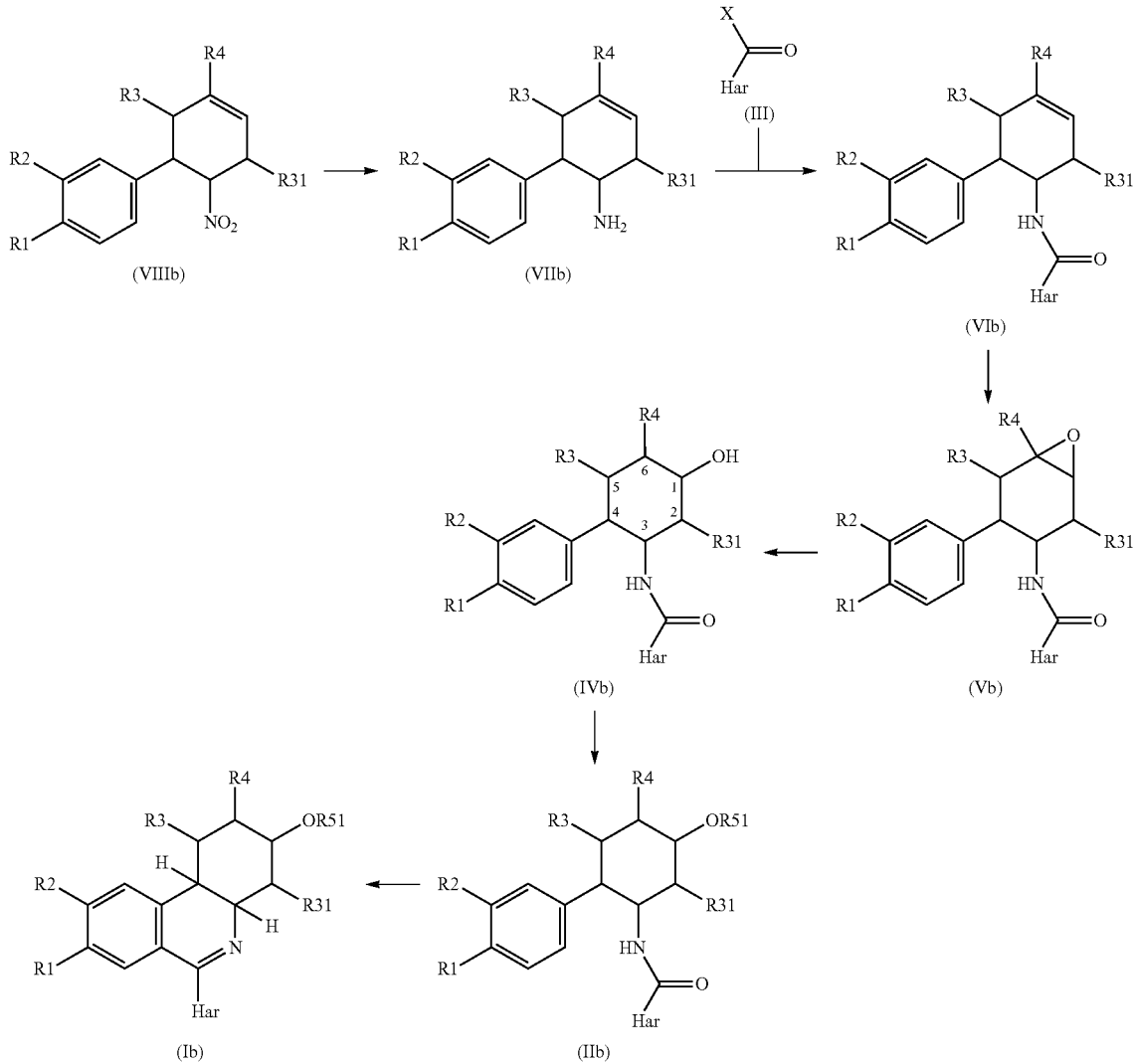

Compounds of the formula VIIb obtained can be reacted, for example, as described by way of example in the following examples with compounds of the formula III, in which R6 and R7 have the meanings given above and X represents a suitable leaving group, preferably a chlorine atom, to give corresponding compounds of the formula VIb.

Alternatively, compounds of the formula VIb, in which R1, R2, R3, R31, R4 and Har have the meanings given above in embodiment b, can also be prepared, for example, from corresponding compounds of the formula VIIb and corresponding compounds of the formula III, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1yl)-N,N,N',N'-tetramthyl-uroriium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

In the next step compounds of the formula VIb are converted into corresponding compounds of the formula Vb by epoxidation reaction, which can be carried out as described in the following examples or in a manner known to one of ordinary skill in the art employing, for example, suitable epoxidation methods or suitable epoxidation reagents such as, for example, peracids (e.g. m-chloroperbenzoic acid) or organic or inorganic peroxides (e. g. dimethyldioxirane, hydrogene peroxide or persulfates).

Compounds of the formula Vb obtained can be reduced by art-known methods to corresponding compounds of the formula IVb. More specifically, said reduction reaction can be performed employing, for example, as described by way of example in the following examples sodium borohydride as reductant. Alternatively, said reduction reaction can be also carried out using, for example, lithium aluminium hydride or a reductive mixture comprising noble metals, such as platinium dioxide or palladium, and a suitable hydrogen donor. With the aid of each of those said reduction methods, compounds of the formula Vb can be converted largely regio- and diastereoselectively into compounds of the formula IVb, wherein the hydroxyl radical in position 1 and the amido radical in position 3 are located at the same side of the plane defined by the cyclohexane ring.

It is moreover known to one of ordinary skill of the art, that the absolute configuration of a chiral carbon atom, preferably, to which a hydroxyl group and a hydrogen atom are bonded, can be inverted. Thus the configuration of the carbon atom in position 1 of compounds of the formula IVb can be optionally inverted. Said inversion of configuration of position 1 of compounds of the formula IVb can be achieved in a manner familiar to the person skilled in the art, for example by derivatization of position 1 with a suitable leaving group and subsequent replacement of said leaving group by a suitable nucleophile in a nucleophilic substitution reaction according to SN2 mechanism. Alternatively, said inversion of configuration of position 1 of compounds of the formula IVb can be also obtained, for example, as described by Way of example in the following examples according to subsequently specified two step procedure shown in reaction scheme 4 below. In more detail, in the first step of said procedure shown in reaction scheme 4, exemplary compounds of the formula IVb*, in which R1, R2 and Har have the meanings indicated above in embodiment b, and R3, R31 and R4 are hydrogen and position 1 has the R configuration, are converted by oxidation reaction into corresponding compounds of the formula IXb. Said oxidation is likewise carried out under conditions customary per se using, for example, chloranil, atmospheric oxygen, manganese dioxide or, preferably, chromium oxides as an oxidant. Then in the second step, compounds of the formula IXb obtained are converted by art-known reduction reaction of the keto group, preferably with metal hydride compounds or, more specifically, metal borohydrides, such as, for example, sodium borohydride, into corresponding compounds of formula IVb**, in which position 1 has now S configuration and thus the configuration of the carbon atom in position 1 is now inverted regarding to said compounds of the formula IVb*.

Reaction scheme 4:

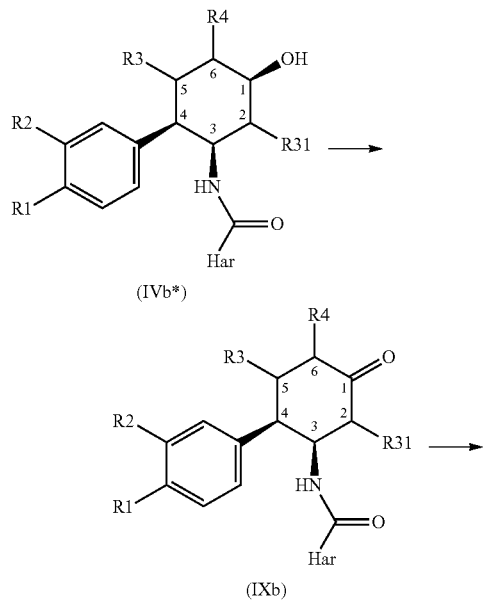

(IVb*)

(IXb)

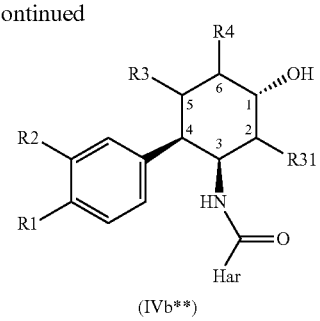

(IVb**)

In the next reaction step of the synthesis route shown in reaction scheme 3 shown above, compounds of the formula IVb are converted into corresponding compounds of the formula IIb by introduction of the group R51 whereby R61 is other than hydrogen. The introduction reaction is carried out in a manner habitual per se (e.g. via alkylation or acylation reaction) or as described by way of example in the following examples.

The cyclization reaction leading to compounds of the formula Ib, in which R1, R2, R3, R31, R4, R51 and Har have the meanings given above in embodiment b whereby R51 is other than hydrogen, can be carried out, for example, as described by way of example in the following examples or analogously or similarly thereto, or as mentioned above for compounds according to embodiment a.

Compounds of the formula VIIIb, in which R1, R2, R3, R31 and R4 have the meanings mentioned above in embodiment b, are either known or can be obtained, for example as shown in reaction scheme 5, by the reaction of compounds of the formula IXa, in which R1 and R2 have the abovementioned meanings, with compounds of the formula Xb, in which R3, R31 and R4 have the meanings indicated above in embodiment b.

Reaction scheme 5:

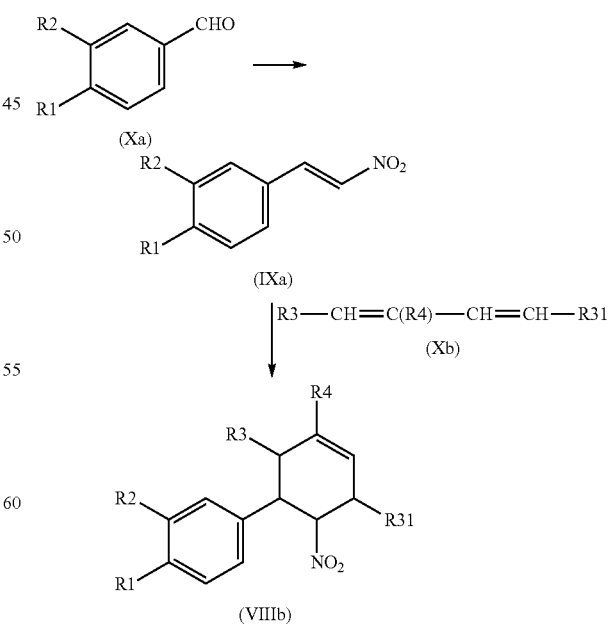

The cycloaddition is in this case carried out in a manner known to the person skilled in the art according to Diels- Alder, e.g. as described in J. Amer. Chem. Soc. 1957, 79, 6559 or in J. Org. Chem. 1952, 17, 581 or as described in the following examples.

Compounds of the formula VIIIb, in which the phenyl ring and the nitro group are trans to one another, can be converted such as known to the person skilled in the art into the corresponding cis compounds, e.g. as described in J. Amer. Chem. Soc. 1957, 79, 6559 or as described in the following examples.

The compounds of the formula Xb are either known or can be prepared in a known manner.

In an alternative, compounds of the formula IIb, in which R1, R2, R3, R31, R4, R51 and Har have the meanings given above in embodiment b whereby R51 is other than hydrogen (particularly compounds of formula IIb, in which R1, R2 and R51 have the meanings given above in embodiment b whereby R51 is other than hydrogen, and R3, R31 and R4 are all hydrogen) can also be obtained as shown in reaction scheme 6 and as described by way of example in the following examples.

In the first reaction step of the route outlined in reaction scheme 6, the amino group of compounds of the formula VIIb is protected with an art-known protective group PG1, such as e.g. the tert-butoxycarbonyl group. The protected compounds are subjected to hydroboration reaction to obtain over two steps compounds of formula XIb. Said hydroboration reaction is carried out as described in the following examples using an appropriate (hydro)borating agent, such as e.g. 9-BBN, isopinocampheyl-borane or the like, or, particularly, borane-tetrahydrofuran ($H_3B$-THF), advantageously at ambient temperature.

The compounds obtained are then converted into compounds of the formula XIb by introduction of the group R51 whereby R51 is other than hydrogen in a manner analogously as described above.

In the next reaction step of the synthesis route shown in reaction scheme 6, compounds of formula XIb are converted into corresponding compounds of the formula IIb by deprotection of the protective group PG1 and amidification with compounds of the formula III. Said reactions are carried out in a manner habitual per se or as described in the specification of this invention or in the following examples.

If necessary, the product obtained via said hydroboration reaction or, suitably, the R51-substituted de-rivative thereof is purified from resulting stereo- and/or regioisomeric side products by methods known to the person skilled in the art, such as e.g. by chromatographic separation techniques.

Reaction scheme 6:

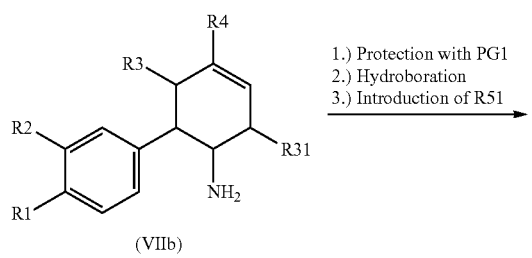

(VIIb)

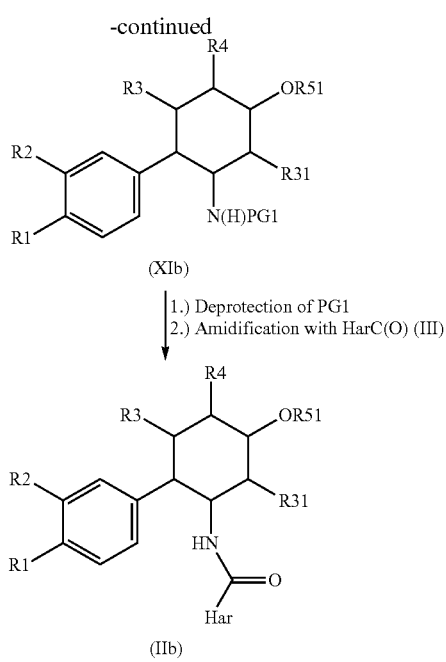

Optionally, compounds of the formula I can be also converted into further compounds of the formula I by methods known to one of ordinary skill in the art. More specifically, for example, from compounds of the formula I in which a) R41 or R51 is hydrogen, the corresponding ester compounds can be obtained by esterification reactions;
b) R41 or R51 is hydrogen, the corresponding ether compounds can be obtained by etherification reactions;
c) R41 or R51 is an acyl group, such as e.g. acetyl, the corresponding hydroxyl compounds can be obtained by deesterification (e.g. saponification) reactions;
d) R6 and/or R7 is chlorine, further compounds of formula I can be obtained via nucleophilic substitution reactions with N, S or O nucleophiles;
e) R6 is an ester group, the corresponding carboxylic acid can be obtained via saponification
f) R6 is a cyano group, the corresponding ester compounds can be obtained via alcoholysis and then hydrolysis, e.g. in acid medium, of the resulting intermediate imino esters.
g) R6 is a cyano group, the corresponding acid compounds can be obtained via alcoholysis and then hydrolysis, e.g. in base medium, of the resulting intermediate imino esters.

The methods mentioned under a), b), c), d), e.), f.) and g.) are expediently carried out analogously to the methods known to the person skilled in the art or as described by way of example in the following examples.

Optionally, compounds of the formula I can be converted into their salts, or, optionally, salts of the compounds of the formula I can be converted into the free compounds.

In addition, the compounds of the formula I can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

It is moreover known to the person skilled in the art that if there are a number of reactive centers on a starting or intermediate compound it may be necessary to block one or more reactive centers tempo-rarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by aci-dification. In this manner, pharmacologically unacceptable salts can be converted into pharmacologically acceptable salts.

The solvates or particularly hydrates of the compounds according to this invention can be prepared in a manner known per se, e.g. in the presence of the appropriate solvent. Hydrates may be obtained from water or from mixtures of water with polar organic solvents (for example alcohols, e.g. methanol, ethanol or isopropanol, or ketones, e.g. acetone).

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of the formula I. All these other possible synthesis routes are also part of this invention.

Having described the invention in detail, the scope of the present invention is not limited only to those described characteristics or embodiments. As will be apparent to persons skilled in the art, modifica-tions, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples serve to illustrate the invention further without restricting it. Likewise, further compounds of the formula I, whose preparation is not explicitly described, can be prepared in an analogous or similar manner or in a manner familiar per se to the person skilled in the art using customary process techniques.

Any or all of the compounds which are mentioned as final compounds in the following examples as well as their salts, N-oxides and salts of the N-oxides are a preferred subject of the present invention.

In the examples, m.p. stands for melting point, h for hour(s), min for minutes, $R_f$ for rentention factor in thin layer chromatography, s.p. for sintering point, EF for empirical formula, MW for molecular weight, MS for mass spectrum, M for molecular ion, fnd. for found, catc. for calculated, other abbreviations have their meanings customary per se to the skilled person.

According to common practice in stereochemistry, the symbols RS and SR are used to denote the specific configuration of each of the chiral centers of a racemate. In more detail, for example, the term "(2RS,4aRS,10bRS)" stands for a racemate (racemic mixture) comprising the one enantiomer having the configuration (2R,4aR,10bR) and the other enantiomer having the configuration (2S,4aS,10bS).

EXAMPLES

Final Compounds 1. (2RS,4aRS,10bRS)-6-(2,6-Dimethoxy-pyridin-3-yl)-9-ethoxy-8-methoxy-1,2,3,4,4a,10b-hexahydro-phenanthridin-2-ol 423 mg of acetic acid (2RS,4aRS,10bRS)-6-(2,6-dimethoxy-pyridin-3-yl)-9-ethoxy-8-methoxy-1,2,3,4,4a,10b-hexahydro-phenanthridin-2-yl ester (Example 18) dissolved in 1 ml of dichloromethane and 9 ml of methanol are added to 152 mg of cesium carbonate and the solution stirred for 19 h. The reaction mixture is adsorbed to silica gel and purified by flash chromatography to give 229 mg of the title compound as a colourless foam.

EF: $C_{23}H_{28}N_2O_5$; MW: calc.: 412.49

MS: fnd.: 413.3 (MH$^+$)

Starting from the appropriate ester compounds, which are mentioned or described explicitly below (compounds 18 to 34), or which can be prepared in a manner known to the person skilled in the art or analogously or similarly to the examples described herein, the following compounds 2 to 17, and also further relevant, non-explicitly described similar compounds are obtained according to the procedure as in Example 1.

2. (2RS,4aRS,10bRS)-9-Ethoxy-8-methoxy-6-(3-methyl-3H-imidazol-4-yl)-1,2,3,4,4a,10b-hexahydro-phenanthridin-2-ol EF: $C_{20}H_{25}N_3O_3$; MW: calc.: 355.44

MS: fnd.: 356.3 (MH$^+$)

3. (2RS,4aRS,10bRS)-9-Ethoxy-8-methoxy-6-(2-pyridin-3-yl-thiazol-4-yl)-1,2,3,4,4a,10b-hexahydro-phenanthridin-2-ol EF: $C_{24}H_{25}N_3O_3S$; MW: calc.: 435.55

MS: fnd.: 436.2 (MH$^+$)

4. (2RS,4aRS,10bRS)-9-Ethoxy-6-isoxazol-5-yl-8-methoxy-1,2,3,4,4a,10b-hexahydro-phenanthridin-2-ol EF: $C_{19}H_{22}N_2O_4$; MW: calc.: 342.4

MS: fnd.: 343.2 (MH$^+$)

5. (2RS,4aRS,10bRS)-8,9-Dimethoxy-6-pyridin-4-yl-1,2,3,4,4a,10b-hexahydro-phenanthridin-2-ol EF: $C_{20}H_{22}N_2O_3$; MW: calc.: 338.41

MS: fnd.: 339.4 (MH$^+$)

6. (2RS,4aRS,10bRS)-8,9-Dimethoxy-6-pyridin-3-yl-1,2,3,4,4a,10b-hexahydro-phenanthridin-2-ol EF: $C_{20}H_{22}N_2O_3$; MW: calc.: 338.41
MS: fnd.: 339.3 (MH$^+$)

7. (2RS,4aRS,10bRS)-8,9-Dimethoxy-6-(6-morpholin-4-yl-pyridin-3-yl)-1,2,3,4,4a,10b-hexahydro-phenanthridin-2-ol EF: $C_{24}H_{29}N_3O_4$; MW: calc.: 423.52
MS: fnd.: 424.4 (MH$^+$)

8. (2RS,4aRS,10bRS)-6-Benzo[1,2,5]oxadiazol-5-yl-9-(1,1-difluoro-methoxy)-8-methoxy-1,2,3,4,4a,10b-hexahydro-phenanthridin-2-ol EF: $C_{21}H_{19}F_2N_3O_4$; MW: calc.: 415.4
MS: fnd.: 416.2 (MH$^+$)

9. (2RS,4aRS,10bRS)-6-Benzo[1,2,5]oxadiazol-5-yl-9-(2,2-difluoro-ethoxy)-8-methoxy-1,2,3,4,4a,10b-hexahydro-phenanthridin-2-ol EF: $C_{22}H_{21}F_2N_3O_4$; MW: calc.: 429.43
MS: fnd.: 430.3 (MH$^+$)

10. (2RS,4aRS,10bRS)-6-Benzo[1,2,5]oxadiazol-5-yl-8-(1,1-difluoro-methoxy)-9-methoxy-1,2,3,4,4a,10b-hexahydro-phenanthridin-2-ol EF: $C_{21}H_{19}F_2N_3O_4$; MW: calc.: 415.4
MS: fnd.: 416.3 (MH$^+$)

11. (2RS,4aRS,10bRS)-6-(2,3-Dihydro-benzo[1,4]dioxin-6-yl)-9-ethoxy-8-methoxy-1,2,3,4,4a,10b-hexahydro-phenanthridin-2-01

EF: $C_{24}H_{27}NO_5$; MW: calc.: 409.49
MS: fnd.: 410.3 (MH$^+$)

12. (2RS,4aRS,10bRS)-6-Benzo[1,3]dioxol-5-yl-9-ethoxy-8-methoxy-1,2,3,4,4a,1 b-hexahydro-phenanthridin-2-ol EF: $C_{23}H_{25}NO_5$; MW: calc.: 395.46
MS: fnd.: 396.2 (MH$^+$)

13. (2RS,4aRS,10bRS)-6-Benzothiazol-6-yl-9-ethoxy-8-methoxy-1,2,3,4,4a,10b-hexahydro-phenanthridin-2-ol EF: $C_{23}H_{24}N_2O_3S$; MW: calc.: 408.52
MS: fnd.: 409.2 (MH$^+$)

14. (2RS,4aRS,10bRS)-8,9-Dimethoxy-6-quinolin-6-yl-1,2,3,4,4a,10b-hexahydro-phenanthridin-2-ol EF: $C_{24}H_{24}N_2O_3$; MW: calc.: 388.47
MS: fnd.: 389.4 (MH$^+$)

15. (2RS,4aRS,10bRS)-6-(2,2-Difluoro-benzo[1,3]dioxol-5-yl)-8,9-dimethoxy-1,2,3,4,4a,10b-hexahydro-phenanthridin-2-ol EF: $C_{22}H_{21}F_2NO_5$; MW: calc.: 417.41
MS: fnd.: 418.4 (MH$^+$)

16. (2RS,4aRS,10bRS)-6-Benzo[1,2,5]oxadiazol-5-yl-9-ethoxy-8-methoxy-1,2,3,4,4a,10b-hexahydro-phenanthridin-2-ol EF: $C_{22}H_{23}N_3O_4$; MW: calc.: 393.45
MS: fnd.: 394.3 (MH$^+$)

17. (2RS,4aRS,10bRS)-9-Ethoxy-8-methoxy-6-(1-methyl-1H-Imidazol-2-yl)-1,2,3,4,4a,10b-hexahydro-phenanthridin-2-ol 18. Acetic acid (2RS,4aRS,10bRS)-6-(2,6-dimethoxy-pyridin-3-yl)-9-ethoxy-8-methoxy-1,2,3,4,4a,10b-hexahydro-phenanthridin-2-yl ester 1.67 g of phosphorus pentachloride are suspended in 5 ml of dichloromethane. 1.227 g of crude acetic acid (1RS,3RS,4RS)-4-{[1-(2,6-dimethoxy-pyridin-3-yl)methanoyl]amino}-3-(3-ethoxy-4-methoxyphenyl)cyclohexyl ester (compound A1) dissolved in 15 ml of dichloromethane are added and the reaction mixture stirred at room temperature over night. The reaction mixture is cooled with an ice bath and 20 ml of triethylamine are added, than cautiously 10 ml of water with vigorous stirring. The organic layer is separated, concentrated and the crude product purified by flash chromatography to give 715 mg of the title compound.

EF: $C_{25}H_{30}N_2O_6$; MW: calc.: 454.53
MS: fnd.: 455.2 (MH$^+$)

Starting from the appropriate starting compounds, which are mentioned or described explicitly below (compounds A2 to A17), or which can be prepared in a manner known to the person skilled in the art or analogously or similarly to the examples described herein, the following compounds 19 to 34, and also further relevant, non-explicitly described similar compounds are obtained according to the procedure as in Example 18. If necessary, the cyclization reaction can be carried out in the presence of a catalytic amount of a Lewis acid such e.g. tin tetrachloride.

19. Acetic acid (2RS,4aRS,10bRS)-9-ethoxy-8-methoxy-6-(3-methyl-3H-imidazol-4-yl)-1,2,3,4,4a,10b-hexahydro-phenanthridin-2-yl ester EF: $C_{22}H_{27}N_3O_4$; MW: calc.: 397.48
MS: fnd.: 398.2 (MH$^+$)

20. Acetic acid (2RS,4aRS,10bRS)-9-ethoxy-8-methoxy-6-(2-pyridin-3-yl-thiazol-4-yl)-1,2,3,4,4a,10b-hexahydro-phenanthridin-2-yl ester EF: $C_{26}H_{27}N_3O_4S$; MW: calc.: 477.59
MS: fnd.: 478.2 (MH$^+$)

21. Acetic acid (2RS,4aRS,10bRS)-9-ethoxy-6-isoxazol-5-yl-8-methoxy-1,2,3,4,4a,10b-hexahydro-phenanthridin-2-yl ester EF: $C_{21}H_{24}N_2O_5$; MW: calc.: 384.44
MS: fnd.: 385.2 (MH$^+$)

22. Acetic acid (2RS,4aRS,10bRS)-8,9-dimethoxy-6-pyridin-4-yl-1,2,3,4,4a,10b-hexahydro-phenanthridin-2-yl ester EF: $C_{22}H_{24}N_2O_4$; MW: calc.: 380.45
MS: fnd.: 381.3 (MH$^+$)

23. Acetic acid (2RS,4aRS,10bRS)-8,9-dimethoxy-6-pyridin-3-yl-1,2,3,4,4a,1 b-hexahydro-phenanthridin-2-yl ester EF: $C_{22}H_{24}N_2O_4$; MW: calc.: 380.45
MS: fnd.: 381.3 (MH$^+$)

24. Acetic acid (2RS,4aRS,10bRS)-8,9-dimethoxy-6-(6-morpholin-4-yl-pyridin-3-yl)-1,2,3,4,4a,1 b-hexahydro-phenanthridin-2-yl ester EF: $C_{26}H_{31}N_3O_5$; MW: calc.: 465.44
MS: fnd.: 466.4 (MH$^+$)

25. Acetic acid (2RS,4aRS,10bRS)-6-benzo[1,2,5]oxadiazol-5-yl-9-(1,1-difluoro-methoxy)-8-methoxy-1,2,3,4,4a,10b-hexahydro-phenanthridin-2-yl ester EF: $C_{23}H_{21}F_2N_3O_5$; MW: calc.: 457.44
MS: fnd.: 458.2 (MH$^+$)

26. Acetic acid (2RS,4aRS,10bRS)-6-benzo[1,2,5]oxadiazol-5-yl-9-(2,2-difluoro-ethoxy)-8-methoxy-1,2,3,4,4a,10b-hexahydro-phenanthridin-2-yl ester EF: $C_{24}H_{23}F_2N_3O_5$; MW: calc.: 471.46
MS: fnd.: 472.2 (MH$^+$)

27. Acetic acid (2RS,4aRS,10bRS)-6-benzo[1,2,5]oxadiazol-5-yl-8-(1,1-difluoro-methoxy)-9-methoxy-1,2,3,4,4a,10b-hexahydro-phenanthridin-2-yl ester EF: $C_{23}H_{21}F_2N_3O_3$; MW: calc.: 457.44
MS: fnd.: 458.2 (MH$^+$)

28. Acetic acid (2RS,4aRS,10bRS)-6-(2,3-dihydro-benzo[1,4]dioxin-6-yl)-9-ethoxy-8-methoxy-1,2,3,4,4a,1 b-hexahydro-phenanthridin-2-yl ester EF: $C_{26}H_{29}F_2NO_6$; MW: calc.: 451.52
MS: fnd.: 452.3 (MH$^+$)

29. Acetic acid (2RS,4aRS,10bRS)-6-benzo[1,3]dioxol-5-yl-9-ethoxy-8-methoxy-1,2,3,4,4a,1b-hexahydro-phenanthridin-2-yl ester EF: $C_{25}H_{27}NO_6$; MW: calc.: 437.5
MS: fnd.: 438.2 (MH$^+$)

30. Acetic acid (2RS,4aRS,10bRS)-6-benzothiazol-6-yl-9-ethoxy-8-methoxy-1,2,3,4,4a,10b-hexahydro-phenanthridin-2-yl ester EF: $C_{25}H_{26}N_2O_4S$; MW: calc.: 450.56
MS: fnd.: 451.2 (MH$^+$)

31. Acetic acid (2RS,4aRS,10bRS)-8,9-dimethoxy-6-quinolin-6-yl-1,2,3,4,4a,10b-hexahydro-phenanthridin-2-yl ester EF: $C_{26}H_{26}N_2O_4$; MW: calc.: 430.51
MS: fnd.: 431.3 (MH$^+$)

32. Acetic acid (2RS,4aRS,10bRS)-6-(2,2-difluoro-benzo[1,3]dioxol-5-yl)-8,9-dimethoxy-1,2,3,4,4a,10b-hexahydro-phenanthridin-2-yl ester EF: $C_{24}H_{23}F_2NO_6$; MW: calc.: 459.48
MS: fnd.: 460.3 (MH$^+$)

33. Acetic acid (2RS,4aRS,10bRS)-6-benzo[1,2,5]oxadiazol-5-yl-9-ethoxy-8-methoxy-1,2,3,4,4a,10b-hexahydro-phenanthridin-2-yl ester EF: $C_{24}H_{25}N_3O_5$; MW: calc.: 435.48
MS: fnd.: 436.3 (MH$^+$)

34. Acetic acid (2 RS,4aRS,10b RS)-9-ethoxy-8-methoxy-6-(1-methyl-1H-imidazol-2-yl)-1,2,3,4,4a,10b-hexahydro-phenanthridin-2-yl ester EF: $C_{22}H_{27}N_3O_4$; MW: calc.: 397.48
MS: fnd.: 398.2 (MH$^+$)

35. 5-((2RS,4aRS,10bRS)-9-Ethoxy-2-hydroxy-8-methoxy-1,2,3,4,4a,10b-hexahydro-phenanthridin-6-yl)-pyridine-2-carboxylic acid methyl ester 532 mg of acetic acid (2RS,4aRS,10bRS)-6-(6-cyano-pyridin-3-yl)-9-ethoxy-8-methoxy-1,2,3,4,4a,10b-hexahydro-phenanthridin-2-yl ester (compound 44) and 248 mg of cesium carbonate are stirred in 10 ml of methanol (optionally 2 ml of dichloromethane can be added) for 19 h. The solvent is removed and the residue purified by chromatography to give 434 mg of the corresponding imino ester (mass calc. 409.49. found MH$^+$410.3).

183 mg of the imino ester are dissolved in 15 ml of 1 M HCl and stirred for 5 h. Na$_2$HPO$_4$ is added (pH=10-11) and extracted with dichloromethane. After drying (Na$_2$SO$_4$) the solvent is removed to give 161 mg of the title compound as a colorless foam.

EF: $C_{23}H_{26}N_2O_5$; MW: calc.: 410.47
MS: fnd.: 411.3

36. (2RS,4aRS,10bRS)-9-(2,2-Difluoro-ethoxy)-6-(2,6-dimethoxy-pyridin-3-yl)-8-methoxy-1,2,3,4,4a,10b-hexahydro-phenanthridin-2-ol Starting from compound 45 the title compound is obtained in an analogous manner as described for Example 1.
EF: $C_{23}H_{26}F_2N_2O_5$; MW: calc.: 448.47
MS: fnd.: 449.3

37. (2RS,4aRS,10bRS)-9-(2,2-Difluoro-ethoxy)-8-methoxy-6-(2-methoxy-pyridin-3-yl)-1,2,3,4,4a,10b-hexahydro-phenanthridin-2-ol Starting from compound 46 the title compound is obtained in an analogous manner as described for Example 1.
EF: $C_{22}H_{24}F_2N_2O_4$; MW: calc.: 418.44
MS: fnd.: 419.2

38. (2RS,4aRS,10bRS)-9-(2,2-Difluoro-ethoxy)-8-methoxy-6-(6-morpholin-4-yl-pyridin-3-yl)-1,2,3,4,4a,10b-hexahydro-phenanthridin-2-ol Starting from compound 47 the title compound is obtained in an analogous manner as described for Example 1.
EF: $C_{25}H_{29}F_2N_3O_4$; MW: calc.: 473.52
MS: fnd.: 474.3

39. (2RS,4aRS,10bRS)-9-(2,2-Difluoro-ethoxy)-8-methoxy-6-pyridin-3-yl-1,2,3,4,4a,10b-hexahydro-phenanthridin-2-ol Starting from compound 48 the title compound is obtained in an analogous manner as described for Example 1.
EF: $C_{21}H_{22}F_2N_2O_3$; MW: calc.: 388.42
MS: fnd.: 389.3

40. (2RS,4aRS,10bRS)-9-(2,2-Difluoro-ethoxy)-6-(2,6-dimethoxy-pyrimidin-4-yl)-8-methoxy-1,2,3,4,4a,10b-hexahydro-phenanthridin-2-ol Starting from compound 49 the title compound is obtained in an analogous manner as described for Example 1.
EF: $C_{22}H_{25}F_2N_3O_5$; MW: calc.: 449.46
MS: fnd.: 450.2

41. (2RS,4aRS,1013RS)-8-(2,2-Difluoro-ethoxy)-6-(2,6-dimethoxy-pyridin-3-yl)-9-methoxy-1,2,3,4,4a,10b-hexahydro-phenanthridin-2-ol Starting from compound 50 the title compound is obtained in an analogous manner as described for Example 1.
EF: $C_{23}H_{26}F_2N_2O_5$; MW: calc.: 448.47
MS: fnd.: 449.3

42. (2RS,4aRS,10bRS)-6-(2,6-Dimethoxy-pyridin-3-yl)-8,9-dimethoxy-1,2,3,4,4a,10b-hexahydro-phenanthridin-2-ol Starting from compound 51 the title compound is obtained in an analogous manner as described for Example 1.
EF: $C_{22}H_{26}N_2O_5$; MW: calc.: 398.46
MS: fnd.: 399.4

43. (2RS,4aRS,10bRS)-6-(2,6-Dimethoxy-pyridin-4-yl)-9-ethoxy-8-methoxy-1,2,3,4,4a,10b-hexahydro-phenanthridin-2-ol Starting from compound 52 the title compound is obtained in an analogous manner as described for Example 1.
EF: $C_{23}H_{28}N_2O_5$; MW: calc.: 412.49 MS: fnd.: 413.2

Starting from the corresponding starting compounds, which are mentioned or described explicitly below (compounds A18 to A26), the following compounds 44 to 52 are obtained according to the procedure as in Example 18. If necessary, the cyclization reaction can be carried out in the presence of a catalytic amount of a Lewis acid such e.g. tin tetrachloride.

44. Acetic acid (2RS,4aRS,10bRS)-6-(6-cyano-pyridin-3-yl)-9-ethoxy-8-methoxy-1,2,3,4,4a,10b-hexahydro-phenanthridin-2-yl ester EF: $C_{24}H_{25}N_3O_4$; MW: calc.: 419.48

45. Acetic acid (2RS,4aRS,10bRS)-9-(2,2-difluoro-ethoxy)-6-(2,6-dimethoxy-pyridin-3-yl)-8-methoxy-1,2,3,4,4a,10b-hexahydro-phenanthridin-2-yl ester EF: $C_{25}H_{28}F_2N_2O_6$; MW: calc.: 490.51
MS: fnd.: 491.2

46. Acetic acid (2RS,4aRS,10bRS)-9-(2,2-difluoro-ethoxy)-8-methoxy-6-(2-methoxy-pyridin-3-yl)-1,2,3,4,4a,10b-hexahydro-phenanthridin-2-yl ester EF: $C_{24}H_{26}F_2N_2O_5$; MW: calc.: 460.48
MS: fnd.: 461.2

47. Acetic acid (2RS,4aRS,10bRS)-9-(2,2-difluoro-ethoxy)-8-methoxy-6-(6-morpholin-4-yl-pyridin-3-yl)-1,2,3,4,4a,10b-hexahydro-phenanthridin-2-yl ester EF: $C_{27}H_{31}F_2N_3O_5$; MW: calc.: 516.56

48. Acetic acid (2RS,4aRS,10bRS)-9-(2,2-difluoro-ethoxy)-8-methoxy-6-pyridin-3-yl-1,2,3,4,4a,10b-hexahydro-phenanthridin-2-yl ester EF: $C_{23}H_{24}F_2N_2O_4$; MW: calc.: 430.46
MS: fnd.: 431.3

49. Acetic acid (2RS,4aRS,10bRS)-9-(2,2-difluoro-ethoxy)-6-(2,6-dimethoxy-pyrimidin-4-yl)-8-methoxy-1,2,3,4,4a,10b-hexahydro-phenanthridin-2-yl ester EF: $C_{24}H_{27}F_2N_3O_6$; MW: calc.: 491.50
MS: fnd.: 492.2

50. Acetic acid (2RS,4aRS,10bRS)-8-(2,2-difluoro-ethoxy)-6-(2,6-dimethoxy-pyridin-3-yl)-9-methoxy-1,2,3,4,4a,10b-hexahydro-phenanthridin-2-yl ester EF: $C_{25}H_{28}F_2N_2O_6$; MW: calc.: 490.51
MS: fnd.: 431.3

51. Acetic acid (2RS,4aRS,10bRS)-6-(2,6-dimethoxy-pyridin-3-yl)-8,9-dimethoxy-1,2,3,4,4a,10b-hexahydro-phenanthridin-2-yl ester EF: $C_{24}H_{28}N_2O_6$; MW: calc.: 440.5
MS: fnd.: 441.3

52. Acetic acid (2RS,4aRS,10bRS)-6-(2,6-dimethoxy-pyridin-4-yl)-9-ethoxy-8-methoxy-1,2,3,4,4a,10b-hexahydro-phenanthridin-2-yl ester EF: $C_{25}H_{30}N_2O_6$; MW: calc.: 454.53
MS: fnd.: 455.2

53. (2RS,4a RS, 10b RS)-6-(3-Chloro-2,6-d methoxy-pyridn-4-yl)-9-(2,2-difluoro-ethoxy)-8-methoxy-1,2,3,4,4a,10b-hexahydro-phenanthridin-2-ol Starting from compound 54 the title compound is obtained in an analogous manner as described for Example 1.
EF: $C_{23}H_{25}Cl\,F_2N_2O_5$; MW: calc.: 482.92
MS: fnd.: 483.2/485.2

54. Acetic acid (2RS,4aRS,10bRS)-6-(3-chloro-2,6-dimethoxy-pyridin-4-yl)-9-(2,2-difluoro-ethoxy)-8-methoxy-1,2,3,4,4a,10b-hexahydro-phenanthridin-2-yl ester Starting from compound A27 the title compound is obtained according to the procedure as in Example 18. If necessary, the cyclization reaction can be carried out in the presence of a catalytic amount of a Lewis acid such e.g. tin tetrachloride.
EF: $C_{25}H_{27}ClF_2N_2O_6$; MW: calc.: 524.95
MS: fnd.: 525.3

55. (2R,4aR,10bR)-9-Ethoxy-8-methoxy-6-pyrimidin-5-yl-1,2,3,4,4a,10b-hexahydro-phenanthridin-2-ol Starting from compound 68 the title compound is obtained in an analogous manner as described for Example 1.
EF: $C_{20}H_{23}N_3O_3$; MW: calc.: 353.42
MS: fnd.: 354.3

56. (2R,4aR,10bR)-9-Ethoxy-8-methoxy-6-(6-pyrazol-1-yl-pyridin-3-yl)-1,2,3,4,4a,10b-hexahydro-phenanthridin-2-ol Starting from compound 69 the title compound is obtained in an analogous manner as described for Example 1.
EF: $C_{24}H_{26}N_4O_3$; MW: calc.: 418.5
MS: fnd.: 419.4
$[\alpha]^{20}_D = -84°$

57. (2R,4aR,10bR)-9-Ethoxy-8-methoxy-6-(3,4,5,6-tetrahydro-2H-[1,2]bipyridinyl-5-yl)-1,2,3,4,4a,10b-hexahydro-phenanthridin-2-ol Starting from compound 70 the title compound is obtained in an analogous manner as described for Example 1.
EF: $C_{26}H_{33}N_3O_3$; MW: calc.: 435.57
MS: fnd.: 436.4

58. 6-((2R,4aR,10bR)-9-Ethoxy-2-hydroxy-8-methoxy-1,2,3,4,4a,10b-hexahydro-phenanthridin-6-yl)-nicotinic acid methyl ester Starting from compound 71 the title compound is obtained in an analogous manner as described for Example 1.
EF: $C_{23}H_{26}N_2O_5$; MW: calc.: 410.47
MS: fnd.: 411.3
$[\alpha]^{20}_D = -82°$

59. (2R,4aR,10bR)-9-Ethoxy-8-methoxy-6-(2-methoxy-pyrimidin-5-yl)-1,2,3,4,4a,10b-hexahydro-phenanthridin-2-ol Starting from compound 72 the title compound is obtained in an analogous manner as described for Example 1.
EF: $C_{21}H_{25}N_3O_4$; MW: calc.: 383.45
MS: fnd.: 384.3

60. (2R,4aR,10bR)-9-Ethoxy-8-methoxy-6-(2,4,6-trimethoxy-pyrimidin-5-yl)-1,2,3,4,4a,10b-hexahydro-phenanthridin-2-ol Starting from compound 73 the title compound is obtained in an analogous manner as described for Example 1.
EF: $C_{23}H_{29}N_3O_6$; MW: calc.: 443.5
MS: fnd.: 444.3

61. (2R,4aR,10bR)-6-(2,4-Dimethoxy-pyrimidin-5-yl)-9-ethoxy-8-methoxy-1,2,3,4,4a,10b-hexahydro-phenanthridin-2-ol Starting from compound 74 the title compound is obtained in an analogous manner as described for Example 1.
EF: $C_nH_{27}N_3O_5$; MW: calc.: 413.48
MS: fnd.: 414.3

62. (2R,4aR,10bR)-9-Ethoxy-8-methoxy-6-(5-methyl-pyrazin-2-yl)-1,2,3,4,4a,10b-hexahydro-phenanthridin-2-ol Starting from compound 75 the title compound is obtained in an analogous manner as described for Example 1.
EF: $C_{21}H_{25}N_3O_3$; MW: calc.: 367.45
MS: fnd.: 368.3

63. (2R,4aR,10bR)-6-(2,6-Dimethoxy-pyrimidin-4-yl)-9-ethoxy-8-methoxy-1,2,3,4,4a,10b-hexahydro-phenanthridin-2-ol Starting from compound 76 the title compound is obtained in an analogous manner as described for Example 1.
EF: $C_{22}H_{27}N_3O_5$; MW: calc.: 413.48
MS: fnd.: 414.3
$[\alpha]^{20}_D = -57°$.

64. (2R,4aR,10bR)-9-Ethoxy-6-(6-imidazol-1-yl-pyridin-3-yl)-8-methoxy-1,2,3,4,4a,10b-hexahydro-phenanthridin-2-ol Starting from compound 77 the title compound is obtained in an analogous manner as described for Example 1.
EF: $C_{24}H_{26}N_4O_3$; MW: calc.: 418.5
MS: fnd.: 419.3

65. (2R,4aR,10bR)-9-Ethoxy-8-methoxy-6-pyrazin-2-yl-1,2,3,4,4a,10b-hexahydro-phenanthridin-2-ol Starting from compound 78 the title compound is obtained in an analogous manner as described for Example 1.
EF: $C_{20}H_{23}N_3O_3$; MW: calc.: 353.42
MS: fnd.: 354.3

66. (2R,4aR,10bR)-9-Ethoxy-8-methoxy-6-(1-methyl-1H-benzotriazol-5-yl)-1,2,3,4,4a,10b-hexahydro-phenanthridin-2-ol Starting from compound 79 the title compound is obtained in an analogous manner as described for Example 1.
EF: $C_{23}H_{26}N_4O_3$; MW: calc.: 406.49
MS: fnd.: 407.2
$[\alpha]^{20}_D = -88°$

67. (2R,4aR,10bR)-9-Ethoxy-8-methoxy-6-(4-methoxy-1,3-dimethyl-1H-pyrazolo[3,4-b]pyridin-5-yl)-1,2,3,4,4a,10b-hexahydro-phenanthridin-2-ol Starting from compound 80 the title compound is obtained in an analogous manner as described for Example 1.
EF: $C_{26}H_{30}N_4O_4$; MW: calc.: 450.54
MS: fnd.: 451.4

Starting from the corresponding starting compounds, which are mentioned or described explicitly below (compounds A28 to A40), the following compounds 68 to 80 are obtained according to the procedure as in Example 18. If necessary, the cyclization reaction can be carried out in the presence of a catalytic amount of a Lewis acid such e.g. tin tetrachloride.

68. Acetic acid (2R,4a R,10bR)-9-ethoxy-8-methoxy-6-pyrimidin-5-yl-1,2,3,4,4a,10b-hexahydro-phenanthridin-2-yl ester EF: $C_{22}H_{26}N_3O_4$; MW: calc.: 395.46
MS: fnd.: 396.3

69. Acetic acid (2R,4aR,10bR)-9-ethoxy-8-methoxy-6-(6-pyrazol-1-yl-pyridin-3-yl)-1,2,3,4,4a,10b-hexahydro-phenanthridin-2-yl ester EF: $C_{26}H_{28}N_4O_4$; MW: calc.: 460.54
MS: fnd.: 461.3

70. Acetic acid (2R,4a R,10bR)-9-ethoxy-8-methoxy-6-(3,4,5,6-tetrahydro-2H-[1,2']bipyridyl-5'-yl)-1,2,3,4,4a,10b-hexahydro-phenanthridin-2-yl ester EF: $C_{28}H_{35}N_3O_4$; MW: calc.: 477.61
MS: fnd.: 478.4

71. 6-((2R,4aR,10bR)-2-Acetoxy-9-ethoxy-8-methoxy-1,2,3,4,4a,10b-hexahydro-phenanthridin-6-yl)-nicotinic acid methyl ester EF: $C_{25}H_{28}N_2O_6$; MW: calc.: 452.51
MS: fnd.: 453.3

72. Acetic acid (2R,4aR,10bR)-9-ethoxy-8-methoxy-6-(2-methoxy-pyrimidin-5-yl)-1,2,3,4,4a,10b-hexahydro-phenanthridin-2-yl ester EF: $C_{23}H_{27}N_3O_5$; MW: calc.: 425.49
MS: fnd.: 426.3

73. Acetic acid (2R,4aR,10bR)-9-ethoxy-8-methoxy-6-(2,4,6-trimethoxy-pyrimidin-5-yl)-1,2,3,4,4a,10b-hexahydro-phenanthridin-2-yl ester EF: $C_{25}H_{31}N_3O_7$; MW: calc.: 485.54
MS: fnd.: 486.3

74. Acetic acid (2R,4aR,10bR)-6-(2,4-dimethoxy-pyrimidin-5-yl)-9-ethoxy-8-methoxy-1,2,3,4,4a,10b-hexahydro-phenanthridin-2-yl ester EF: $C_{24}H_{29}N_3O_6$; MW: calc.: 455.52
MS: fnd.: 456.3

75. Acetic acid (2R,4aR,10bR)-9-ethoxy-8-methoxy-6-(5-methyl-pyrazin-2-yl)-1,2,3,4,4a,10b-hexahydro-phenanthridin-2-yl ester EF: $C_{23}H_{27}N_3O_4$; MW: calc.: 409.49
MS: fnd.: 410.3

76. Acetic acid (2R,4aR,10bR)-6-(2,6-dimethoxy-pyrimidin-4-yl)-9-ethoxy-8-methoxy-1,2,3,4,4a,10b-hexahydro-phenanthridin-2-yl ester EF: $C_{24}H_{29}N_3O_6$; MW: calc.: 455.52
MS: fnd.: 456.3

77. Acetic acid (2R,4aR,1013R)-9-ethoxy-6-(6-imidazol-1-yl-pyridin-3-yl)-8-methoxy-1,2,3,4,4a,10b-hexahydro-phenanthridin-2-yl ester EF: $C_{26}H_{28}N_4O_4$; MW: calc.: 460.55
MS: fnd.: 461.3

78. Acetic acid (2R,4aR,10bR)-9-ethoxy-8-methoxy-6-pyrazin-2-yl-1,2,3,4,4a,10b-hexahydro-phenanthridin-2-yl ester EF: $C_{22}H_{25}N_3O_4$; MW: calc.: 395.46
MS: fnd.: 396.3

79. Acetic acid (2R,4aR,10bR)-9-ethoxy-8-methoxy-6-(1-methyl-1H-benzotriazol-5-yl)-1,2,3,4,4a,10b-hexahydro-phenanthridin-2-yl ester EF: $C_{25}H_{28}N_4O_4$; MW: calc.: 448.53
MS: fnd.: 449.3

80. Acetic acid (2R,4aR,10bR)-9-ethoxy-8-methoxy-6-(4-methoxy-1,3-dimethyl-1H-pyrazolo[3,4-b]pyridin-5-yl)-1,2,3,4,4a,10b-hexahydro-phenanthridin-2-yl ester EF: $C_{27}H_{32}N_4O_5$; MW: calc.: 492.58
MS: fnd.: 493.4

81. (2S,4aS,10bS)-6-(2,6-Dim ethoxy-pyridin-3-yl)-9-ethoxy-8-methoxy-1,2,3,4,4a,10b-hexahydro-phenanthridin-2-ol The title compound can be obtained by chromatographical separation of the corresponding racemate (Example 1) using a column as described below at the end of the chapter "Final compounds".
EF: $C_{23}H_{28}N_2O_5$; MW: calc.: 412.49
MS: fnd.: 413.3

82. (2R,4aR,10bR)-6-(2,6-Dimethoxy-pyridin-3-yl)-9-ethoxy-8-methoxy-1,2,3,4,4a,10b-hexahydro-phenanthridin-2-ol Starting from compound 83 the title compound is obtained in an analogous manner as described for Example 1.
Alternatively, the title compound can be obtained by chromatographical separation of the corresponding racemate (Example 1) using a column as described below at the end of the chapter "Final compounds".
EF: $C_{23}H_{28}N_2O_8$; MW: calc.: 412.49
MS: fnd.: 413.3

83. Acetic acid (2R,4a R,10bR)-6-(2,6-dimethoxy-pyrid n-3-yl)-9-ethoxy-8-methoxy-1,2,3,4,4a, 10b-hexahydro-phenanthridin-2-yl ester Starting from compound A41 the title compound is obtained according to the procedure as in Example 18. If necessary, the cyclization reaction can be carried out in the presence of a catalytic amount of a Lewis acid such e.g. tin tetrachloride.
EF: $C_{28}H_{30}N_2O_8$; MW: calc.: 454.53
MS: fnd.: 455.3

84. (3SR,4aRS,10bRS)-8,9-Dimethoxy-6-pyridin-3-yl-1,2,3,4,4a,10b-hexahydro-phenanthridin-3-ol Starting from compound 85 the title compound is obtained in an analogous manner as described for Example 1.

EF: $C_{20}H_{22}N_2O_3$; MW: calc.: 338.41
MS: fnd.: 339.3

85. Acetic acid (3SR,4aRS,10bRS)-8,9-dimethoxy-6-pyridin-3-yl-1,2,3,4,4a,10b-hexahydro-phenanthridin-3-yl ester Starting from compound A42 the title compound is obtained according to the procedure as in Example 18. If necessary, the cyclization reaction can be carried out in the presence of a catalytic amount of a Lewis acid such e.g. tin tetrachloride.
EF: $C_{22}H_{24}N_2O_4$; MW: calc.: 380.45
MS: fnd.: 381.3

86. (2R,4aR,10bR)-6-(4-Chloro-2,6-dimethoxy-pyridin-3-yl)-9-ethoxy-8-methoxy-1,a3,4,4a,10b-hexahydro-phenanthridin-2-ol Starting from compound 87 the title compound is obtained in an analogous manner as described for Example 1.
EF: $C_{23}H_{27}ClN_2O_5$; MW: calc.: 446.94
MS: fnd.: 447.3

87. Acetic acid (2R,4aR,10bR)-6-(4-chloro-2,6-dimethoxy-pyridin-3-yl)-9-ethoxy-8-methoxy-1,2,3,4,4a,10b-hexahydro-phenanthridin-2-yl ester Starting from compound A41 the title compound is obtained according to the procedure as in Example 83 as side product.
EF: $C_{25}H_{29}ClN_2O_6$; MW: calc.: 488.97
MS: fnd.: 489.2

Starting from the appropriate ester compounds, which are mentioned or described explicitly below (compounds 96 to 103), or which can be prepared in a manner known to the person skilled in the art or analogously or similarly to the examples described herein, the following compounds 88 to 95, and also further relevant, non-explicitly described similar compounds are obtained according to the procedure as in Example 1.

88. (2R,4aR,10bR)-9-Ethoxy-8-methoxy-6-(2-methylsulfanyl-pyridin-3-yl)-1,2,3,4,4a,10b-hexahydro-phenanthridin-2-ol $C_{22}H_{26}N_2O_3S$
Calc.: 398.53
Found (MH$^+$): 399.2

89. (2R,4aR,10bR)-9-Ethoxy-8-methoxy-6-(4-methyl-2-methylsulfanyl-pyrimidin-5-yl)-1,2,3,4,4a,10b-hexahydro-phenanthridin-2-ol $C_{22}H_{27}N_3O_3S$
Calc.: 413.54
Found (MH$^+$): 414.2

90. (2R,4aR,10bR)-6-(5-Chloro-2-methylsulfanyl-pyrimidin-4-yl)-9-ethoxy-8-methoxy-1,2,3,4,4a,10b-hexahydro-phenanthridin-2-ol $C_{21}H_{24}ClN_3O_3S$
Calc.: 433.96
Found (MH$^+$): 434.2 and 436.2

91. (2R,4aR,10bR)-9-Ethoxy-8-methoxy-6-(2-methoxy-pyridin-3-yl)-1,2,3,4,4a,10b-hexahydro-phenanthridin-2-ol $C_{22}H_{26}N_2O_4$
Calc.: 382.46
Found (MH$^+$): 383.2

92. 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one $C_{22}H_{26}N_2O_4$
Calc.: 382.46
Found (MH$^+$): 383.2

93. (2R,4aR,10bR)-9-Ethoxy-8-methoxy-6-(6-methoxy-pyridin-3-yl)-1,2,3,4,4a,10b-hexahydro-phenanthridin-2-ol $C_{22}H_{26}N_2O_4$
Calc.: 382.46
Found (MH$^+$): 383.3

94. (2R,4aR,10bR)-6-(4-Chloro-2-dimethylamino-pyrimidin-5-yl)-9-ethoxy-8-methoxy-1,2,3,4,4a,10b-hexahydro-phenanthridin-2-ol $C_{22}H_{27}ClN_4O_3$
Calc.: 430.94
Found (MH$^+$): 431.3 and 433.2

95. (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol $C_{23}H_{30}N_4O_4$
Calc.: 426.52
Found (MH$^+$): 427.3

Starting from the corresponding starting compounds, which are mentioned or described explicitly below (compounds A43 to A50), the following compounds 96 to 103 are obtained according to the procedure as in Example 18. If necessary, the cyclization reaction can be carried out in the presence of a catalytic amount of a Lewis acid such e.g. tin tetrachloride.

96. Acetic acid (2R,4aR,10bR)-9-ethoxy-8-methoxy-6-(2-methylsulfanyl-pyridin-3-yl)-1,2,3,4,4a,10b-hexahydro-phenanthridin-2-yl ester $C_{24}H_{28}N_2O_4S$
Calc.: 440.57
Found (MH$^+$): 441.2

97. Acetic acid (2R,4aR,10bR)-9-ethoxy-8-methoxy-6-(4-methyl-2-methylsulfanyl-pyrimidin-5-yl)-1,2,3,4,4a,10b-hexahydro-phenanthridin-2-yl ester $C_{24}H_{23}N_3O_4S$
Calc.: 455.58
Found (MH$^+$): 456.2

98. Acetic acid (2R,4aR,10bR)-6-(5-chloro-2-methylsulfanyl-pyrimidin-4-yl)-9-ethoxy-8-methoxy-1,2,3,4,4a,10b-hexahydro-phenanthridin-2-yl ester $C_{23}H_{26}ClN_3O_4S$
Calc.: 476.00
Found (MH$^+$): 476.2 and 478.1

99. Acetic acid (2R,4aR,10bR)-9-ethoxy-8-methoxy-6-(2-methoxy-pyridin-3-yl)-1,2,3,4,4a,10b-hexahydro-phenanthridin-2-yl ester $C_{24}H_{28}N_2O_5$
Calc.: 424.50
Found (MH$^+$): 425.3

100. Acetic acid (2R,4aR,10bR)-9-ethoxy-8-methoxy-6-(1-methyl-6-oxo-1,6-dihydro-pyridin-3-yl)-1,2,3,4,4a,10b-hexahydro-phenanthridin-2-yl ester $C_{24}H_{28}N_2O_5$
Calc.: 424.50
Found (MH$^+$): 425.3

101. Acetic acid (2R,4aR,10bR)-9-ethoxy-8-methoxy-6-(6-methoxy-pyridin-3-yl)-1,2,3,4,4a,10b-hexahydro-phenanthridin-2-yl ester $C_{24}H_{28}N_2O_5$
Calc.: 424.50
Found (MH$^+$): 425.2

102. Acetic acid (2R,4aR,10bR)-6-(4-chloro-2-dimethylamino-pyrimidin-5-yl)-9-ethoxy-8-methoxy-1,2,3,4,4a,10b-hexahydro-phenanthridin-2-yl ester The title compound is obtained from compound A50 under the cyclization conditions used.
$C_{24}H_{29}ClN_4O_4$
Calc.: 472.98
Found (MH$^+$): 473.3 and 475.2

103. Acetic acid (2R,4aR,10bR)-6-(2-dimethylamino-4-methoxy-pyrimidin-5-yl)-9-ethoxy-8-methoxy-1,2,3,4,4a,10b-hexahydro-phenanthridin-2-yl ester $C_{25}H_{32}N_4O_5$
Calc.: 468.56
Found (MH$^+$): 469.3

Starting from the appropriate ester compounds, which are mentioned or described explicitly below (compounds 111 to 117), or which can be prepared in a manner known to the person skilled in the art or analogously or similarly to the examples described herein, the following compounds 104 to 110 can be obtained according to the procedure as in Example 1.

104. (2R,4aR,10bR)-6-(4,6-Diethoxy-pyridin-3-yl)-9-ethoxy-8-methoxy-1,2,3,4,4a,10b-hexahydro-phenanthridin-2-ol $C_{25}H_{32}N_2O_5$
Calc.: 440.54
Found (MH$^+$): 441.3

105. (2R,4aR,10bR)-6-(4,6-Dimethoxy-pyridin-3-yl)-9-ethoxy-8-methoxy-1,2,3,4,4a,10b-hexahydro-phenanthridin-2-ol $C_{23}H_{28}N_2O_5$
Calc.: 412.49
Found (MH$^+$): 413.3

106. (2R,4aR,10bR)-6-(2-Dimethylamino-pyrimidin-5-yl)-9-ethoxy-8-methoxy-1,2,3,4,4a,10b-hexahydro-phenanthridin-2-ol $C_{22}H_{28}N_4O_3$
Calc.: 396.49
Found (MH$^+$): 397.3

107. (2R,4aR,10bR)-6-(5,6-Dimethoxy-pyridin-3-yl)-9-ethoxy-8-methoxy-1,2,3,4,4a,10b-hexahydro-phenanthridin-2-ol $C_{23}H_{28}N_2O_5$
Calc.: 412.49

108. (2R,4aR,10bR)-9-Ethoxy-6-(5-ethoxy-6-methoxy-pyridin-3-yl)-8-methoxy-1,2,3,4,4a,10b-hexahydro-phenanthridin-2-ol $C_{24}H_{30}N_2O_5$
Calc.: 426.52

109. (2R,4aR,10bR)-9-Ethoxy-8-methoxy-6-(2-methylsulfanyl-pyrimidin-5-yl)-1,2,3,4,4a,10b-hexahydro-phenanthridin-2-ol $C_{21}H_{25}N_3O_3S$
Calc.: 399.52

110. 5-((2R,4aR,10b R)-9-Ethoxy-2-hydroxy-8-methoxy-1,2,3,4,4a,10b-hexahydro-phenanthridin-6yl)-1-methyl-1H-pyrimidin-2-one $C_{21}H_{25}N_3O_4$
Calc.: 383.45

Starting from the corresponding starting compounds, which are mentioned or described explicitly below (compounds A51 to A57), the following compounds 111 to 117 can be obtained according to the procedure as in Example 18. If necessary, the cyclization reaction can be carried out in the presence of a catalytic amount of a Lewis acid such e.g. tin tetrachloride.

111. Acetic acid (2R,4aR,10bR)-6-(4,6-diethoxy-pyridin-3-yl)-9-ethoxy-8-methoxy-1,2,3,4,4a,10b-hexahydro-phenanthridin-2-yl ester $C_{27}H_{34}N_2O_6$
Calc.: 482.58
Found (MH$^+$): 483.3

112. Acetic acid (2R,4aR,10bR)-6-(4,6-dimethoxy-pyridin-3-yl)-9-ethoxy-8-methoxy-1,2,3,4,4a,10b-hexahydro-phenanthridin-2-yl ester $C_{25}H_{30}N_2O_6$
Calc.: 454.53
Found (MH$^+$): 455.3

113. Acetic acid (2R,4aR,10bR)-6-(2-dimethylamino-pyrimidin-5-yl)-9-ethoxy-8-methoxy-1,2,3,4,4a,10b-hexahydro-phenanthridin-2-yl ester $C_{24}H_{30}N_4O_4$
Calc.: 438.53
Found (MH$^+$): 439.3

114. Acetic acid (2R,4aR,10bR)-6-(5,6-dimethoxy-pyridin-3-yl)-9-ethoxy-8-methoxy-1,2,3,4,4a,10b-hexahydro-phenanthridin-2-yl ester $C_{25}H_{30}N_2O_6$
Calc.: 454.53

115. Acetic acid (2R,4aR,10bR)-9-ethoxy-6-(5-ethoxy-6-methoxy-pyridin-3-yl)-8-methoxy-1,2,3,4,4a,10b-hexahydro-phenanthridin-2-yl ester $C_{26}H_{32}N_2O_6$
Calc.: 468.55

116. Acetic acid (2R,4aR,10bR)-9-ethoxy-8-methoxy-6-(2-methylsulfanyl-pyrimidin-5-yl)-1,2,3,4,4a,10b-hexahydro-phenanthridin-2-yl ester $C_{23}H_{27}N_3O_4S$
Calc.: 441.55

117. Acetic acid (2R,4aR,10bR)-9-ethoxy-8-methoxy-6-(1-methyl-2-oxo-1,2-dihydro-pyrimidin-5-yl)-1,2,3,4,4a,10b-hexahydro-phenanthridin-2-yl ester $C_{23}H_{27}N_3O_6$
Calc.: 425.49

Starting from the appropriate ester compounds, which are mentioned or described explicitly below (compounds 121 to 123), or which can be prepared in a manner known to the person skilled in the art or analogously or similarly to the examples described herein, the following compounds 118 to 120 can be obtained according to the procedure as in Example 1.

118. (2R,4aR,10bR)-9-Ethoxy-6-(6-hydroxy-pyridin-3-yl)-8-methoxy-1,2,3,4,4a,10b-hexahydro-phenanthridin-2-ol $C_{21}H_{24}N_2O_4$
Calc.: 368.44
Found (MH$^+$): 369.3

119. (2R,4aR,10bR)-6-(3,6-Dimethoxy-pyridazin-4-yl)-9-ethoxy-8-methoxy-1,2,3,4,4a,10b-hexahydro-phenanthridin-2-ol $C_2{}_2H_{27}N_3O_5$
Calc.: 413.48
Found (MH$^+$): 414.3

120. (2R,4aR,10bR)-6-(4,6-Dimethoxy-pyrimidin-5-yl)-9-ethoxy-8-methoxy-1,2,3,4,4a,10b-hexahydro-phenanthridin-2-ol $C_{22}H_{27}N_3O_5$
Calc.: 413.48
Found (MH$^+$): 414.3

Starting from the corresponding starting compounds, which are mentioned or described explicitly below (compounds A58 to A60), the following compounds 121 to 123 can be obtained according to the procedure as in Example 18. If necessary, the cyclization reaction can be carried out in the presence of a catalytic amount of a Lewis acid such e.g. tin tetrachloride.

121. Acetic acid (2R,4aR,10bR)-9-ethoxy-6-(6-hydroxy-pyridin-3-yl)-8-methoxy-1,2,3,4,4a,10b-hexahydro-phenanthridin-2-yl ester $C_{23}H_{26}N_2O_6$
Calc.: 410.47
Found (MH$^+$): 411.3

122. Acetic acid (2R,4aR,10bR)-6-(3,6-dimethoxy-pyridazin-4-yl)-9-ethoxy-8-methoxy-1,2,3,4,4a,10b-hexahydro-phenanthridin-2-yl ester $C_{24}H_{29}N_3O_6$
Calc.: 455.52
Found (MH$^+$): 456.3

123. Acetic acid (2R,4aR,10bR)-6-(4,6-dimethoxy-pyrimidin-5-yl)-9-ethoxy-8-methoxy-1,2,3,4,4a,10b-hexahydro-phenanthridin-2-yl ester $C_{24}H_{29}N_3O_6$
Calc.: 455.52
Found (MH$^+$): 456.3

Starting from the appropriate ester compounds, which are mentioned or described explicitly below (compounds 143 to 160), or which can be prepared in a manner known to the person skilled in the art or analogously or similarly to the examples described herein, the following compounds 124 to 142 can be obtained according to the procedure as in Example 1.

124. (2RS,4aRS,10bRS)-9-Ethoxy-8-methoxy-6-pyridin-4-yl-1,2,3,4,4a,10b-hexahydro-phenanthridin-2-ol $C_{21}H_{24}N_2O_3$
Calc.: 352.44
Found (MH+): 353.3

125. (2RS,4aRS,10bRS)-9-Ethoxy-8-methoxy-6-pyridin-3-yl-1,2,3,4,4a,10b-hexahydro-phenanthridin-2-ol $C_{21}H_{24}N_2O_3$
Calc.: 352.44
Found (MH+): 353.3

126. (2RS,4aRS,10bRS)-9-Ethoxy-8-methoxy-6-(6-morpholin-4-yl-pyridin-3-yl)-1,2,3,4,4a,10b-hexahydro-phenanthridin-2-ol $C_{25}H_{31}N_3O_4$
Calc.: 437.54
Found (MH+): 438.4

127. (2RS,4aRS,10bRS)-9-(1,1-Difluoro-methoxy)-6-(2,6-dimethoxy-pyridin-3-yl)-8-methoxy-1,2,3,4,4a,10b-hexahydro-phenanthridin-2-ol $C_{22}H_{24}F_2N_2O_5$
Calc.: 434.44
Found (MH+): 435.3

128. (2RS,4aRS,10bRS)-8-(1,1-Difluoro-methoxy)-6-(2,6-dimethoxy-pyridin-3-yl)-9-methoxy-1,2,3,4,4a,10b-hexahydro-phenanthridin-2-ol $C_{22}H_{24}F_2N_2O_5$
Calc.: 434.44
Found (MH+): 435.2

129. (2RS,4aRS,10bRS)-6-Benzo[1,2,5]oxadiazol-5-yl-8-(1,1-difluoro-methoxy)-9-methoxy-1,2,3,4,4a,10b-hexahydro-phenanthridin-2-ol $C_{21}H_{19}F_2N_3O_4$
Calc.: 415.4
Found (MH+): 416.3

130. (2RS,4aRS,10bRS)-6-(2,6-Dimethoxy-pyrimidin-4-yl)-9-ethoxy-8-methoxy-1,2,3,4,4a,10b-hexahydro-phenanthridin-2-ol $C_{22}H_{27}N_3O_5$
Calc.: 413.48
Found (MH+): 414.2

131. (2RS,4aRS,10bRS)-6-(5-Chloro-2,6-bis-dimethylamino-pyrimidin-4-yl)-9-ethoxy-8-methoxy-1,2,3,4,4a,10b-hexahydro-phenanthridin-2-ol $C_{24}H_{82}ClN_5O_3$
Calc.: 474.01
Found (MH+): 474.2/476.3

132. (2RS,4aRS,10bRS)-9-Ethoxy-8-methoxy-6-pyrimidin-5-yl-1,2,3,4,4a,10b-hexahydro-phenanthridin-2-ol $C_{20}H_{23}N_3O_3$
Calc.: 353.42
Found (MH+): 354.2

133. (2RS,4aRS,10bRS)-9-Ethoxy-8-methoxy-6-pyrazin-2-yl-1,2,3,4,4a,10b-hexahydro-phenanthridin-2-ol $C_{20}H_{23}N_3O_3$
Calc.: 353.42
Found (MH+): 354.3

134. (2RS,4aRS,10bRS)-6-(5-Chloro-4-methyl-3,4-dihydro-2H-benzo[1,4]oxazin-7-yl)-9-ethoxy-8-methoxy-1,2,3,4,4a,10b-hexahydro-phenanthridin-2-ol $C_{25}H_{23}ClN_2O_4$
Calc.: 456.97
Found (MH+): 457.3/459.3

135. (2RS,4aRS,10bRS)-9-Ethoxy-8-methoxy-6-(6-pyrazol-1-yl-pyridin-3-yl)-1,2,3,4,4a,10b-hexahydro-phenanthridin-2-ol $C_{24}H_{26}N_4O_3$
Calc.: 418.5
Found (MH+): 419.3

136. (2RS,4aRS,10bRS)-9-Ethoxy-6-(6-imidazol-1-yl-pyridin-3-yl)-8-methoxy-1,2,3,4,4a,10b-hexahydro-phenanthridin-2-ol $C_{24}H_{26}N_4O_3$
Calc.: 418.5
Found (MH+): 419.2

137. (2RS,4aRS,10bRS)-6-Benzo[1,2,3]thiadiazol-5-yl-9-ethoxy-8-methoxy-1,2,3,4,4a,10b-hexahydro-phenanthridin-2-ol $C_{22}H_{23}N_3O_3S$
Calc.: 409.51
Found (MH+): 410.1

138. (2RS,4aRS,10bRS)-9-Ethoxy-8-methoxy-6-[6-(2-pyrrolidin-1-yl-ethyl)-pyridin-3-yl]-1,2,3,4,4a,10b-hexahydro-phenanthridin-2-ol $C_{27}H_{35}N_3O_3$
Calc.: 449.6
Found (MH+): 450.2

139. (2RS,4aRS,10bRS)-9-Ethoxy-8-methoxy-6-(2-methoxy-pyridin-3-yl)-1,2,3,4,4a,10b-hexahydro-phenanthridin-2-ol $C_{22}H_{26}N_2O_4$
Calc.: 382.46
Found (MH+): 383.2

140. (2RS,4aRS,10bRS)-9-Ethoxy-8-methoxy-6-(1-methyl-1H-benzotriazol-5-yl)-1,2,3,4,4a,10b-hexahydro-phenanthridin-2-ol $C_{23}H_{26}N_4O_3$
Calc.: 406.49
Found (MH+): 407.2

141. (2RS,4aRS,10bRS)-9-Ethoxy-8-methoxy-6-quinoxalin-5-yl-1,2,3,4,4a,10b-hexahydro-phenanthridin-2-ol $C_{24}H_{25}N_3O_3$
Calc.: 403.49
Found (MH+): 404.2

142. (2RS,4aRS,10bRS)-6-(3-Chloro-2,6-dimethoxy-pyridin-4-yl)-9-ethoxy-8-methoxy-1,2,3,4,4a,10b-hexahydro-phenanthridin-2-ol $C_{23}H_{27}ClN_2O_5$
Calc.: 446.94
Found (MH+): 447.3

Starting, unless otherwise mentioned, from the corresponding starting compounds, which can be prepared in a manner known to the person skilled in the art—analogously or similarly to the starting compounds described herein below, the following compounds 143 to 160 can be obtained according to the procedure as in Example 18. If necessary, the cyclization reaction can be carried out in the presence of a catalytic amount of a Lewis acid such e.g. tin tetrachloride.

143. Acetic acid (2RS,4aRS,10bRS)-9-ethoxy-8-methoxy-6-pyridin-4-yl-1,2,3,4,4a,10b-hexahydro-phenanthridin-2-yl ester $C_{23}H_{26}N_2O_4$
Calc.: 394.47
Found (MH+): 395.3

144. Acetic acid (2RS,4aRS,1013RS)-9-ethoxy-8-methoxy-6-pyridin-3-yl-1,2,3,4,4a,10b-hexahydro-phenanthridin-2-yl ester $C_{23}H_{26}N_2O_4$
Calc.: 394.47
Found (MH+): 395.3

145. Acetic acid (2RS,4aRS,10bRS)-9-ethoxy-8-methoxy-6-(6-morpholin-4-yl-pyridin-3-yl)-1,2,3,4,4a,10b-hexahydro-phenanthridin-2-yl ester $C_{27}H_{33}N_3O_5$
Calc.: 479.58
Found (MH+): 480.4

146. Acetic acid (2RS,4aRS,10bRS)-9-(1,1-difluoro-methoxy)-6-(2,6-dimethoxy-pyridin-3-yl)-8-methoxy-1,2,3,4,4a,10b-hexahydro-phenanthridin-2-yl ester $C_{24}H_{26}F_2N_2O_6$
Calc.: 476.48
Found (MH+): 477.4

147. Acetic acid (2RS,4aRS,10bRS)-8-(1,1-difluoro-methoxy)-6-(2,6-dimethoxy-pyridin-3-yl)-9-methoxy-1,2,3,4,4a,10b-hexahydro-phenanthridin-2-yl ester $C_{24}H_{26}F_2N_2O_6$
Calc.: 476.48
Found (MH+): 477.3

148. Acetic acid (2RS,4aRS,10bRS)-6-benzo[1,2,5]oxadiazol-5-yl-8-(11-difluoro-methoxy)-9-methoxy-1,2,3,4,4a,10b-hexahydro-phenanthridin-2-yl ester 149. Acetic acid (2 RS,4aRS,10bRS)-6-(2,6-dimethoxy-pyrimidin-4-yl)-9-ethoxy-8-methoxy-1,2,3,4,4a,10b-hexahydro-phenanthridin-2-yl ester $C_{24}H_{23}N_3O_6$
Calc.: 455.52
Found (MH+): 456.2

150. Acetic acid (2RS,4aRS,10bRS)-6-(5-chloro-2,6-bis-dimethylamino-pyrimidin-4-yl)-9-ethoxy-8-methoxy-1,2,3,4,4a,10b-hexahydro-phenanthridin-2-yl ester The title compound is obtained from acetic acid (1RS,3RS,4RS)-4-{[1-(bis-dimethylamino-pyrimidin-4-yl)-methanoyl]-amino}-3-(3-ethoxy-4-methoxy-phenyl)-cyclohexyl ester under the cyclization conditions used.
$C_{26}H_{34}ClN_5O_4$
Calc.: 516.04
Found (MH+): 516.3/518.3

151. Acetic acid (2RS,4aRS,10bRS)-9-ethoxy-8-methoxy-6-pyrimidin-5-yl-1,2,3,4,4a,10b-hexahydro-phenanthridin-2-yl ester $C_{22}H_{25}N_3O_4$
Calc.: 395.46
Found (MH+): 396.2

152. Acetic acid (2RS,4aRS,10bRS)-9-ethoxy-8-methoxy-6-pyrazin-2-yl-1,2,3,4,4a,10b-hexahydro-phenanthridin-2-yl ester $C_{22}H_{25}N_3O_4$
Calc.: 395.46
Found (MH+): 396.2

153. Acetic acid (2RS,4aRS,10bRS)-6-(5-chloro-4-methyl-3,4-dihydro-2H-benzo[1,4]oxazin-7-yl)-9-ethoxy-8-methoxy-1,2,3,4,4a,10b-hexahydro-phenanthridin-2-yl ester The title compound is obtained from acetic acid (1R,3R,4R)-3-(3-ethoxy-4-methoxy-phenyl)-4-{[1-(4-methyl-3,4-dihydro-2H-benzo[1,4]oxazin-7-yl)-methanoyl]-amino}-cyclohexyl ester under the cyclization conditions used.
$C_{27}H_{31}ClN_2O_5$
Calc.: 499.01
Found (MH+): 499.2/501.2

164. Acetic acid (2RS,4aRS,10bRS)-9-ethoxy-8-methoxy-6-(6-pyrazol-1-yl-pyridin-3-yl)-1,2,3,4,4a,10b-hexahydro-phenanthridin-2-yl ester $C_{28}H_{28}N_4O_4$
Calc.: 460.54
Found (MH+): 461.3

155. Acetic acid (2RS,4aRS,10bRS)-9-ethoxy-6-(6-imidazol-1-yl-pyridin-3-yl)-8-methoxy-1,2,3,4,4a,10b-hexahydro-phenanthridin-2-yl ester $C_{26}H_{28}N_4O_4$
Calc.: 460.54
Found (MH+): 461.3

156. Acetic acid (2RS,4aRS,10bRS)-6-benzo[1,2,3]thiadiazol-5-yl-9-ethoxy-8-methoxy-1,2,3,4,4a,10b-hexahydro-phenanthridin-2-yl ester $C_{24}H_{25}N_3O_4S$
Calc.: 451.55
Found (MH+): 452.1

157. Acetic acid (2RS,4aRS,10bRS)-9-ethoxy-8-methoxy-6-[6-(2-pyrrolidin-1-yl-ethyl)-pyridin-3-yl]-1,2,3,4,4a,10b-hexahydro-phenanthridin-2-yl ester $C_{29}H_{37}N_3O_4$
Calc.: 491.64
Found (MH+): 492.3

158. Acetic acid (2RS,4aRS,10bRS)-9-ethoxy-8-methoxy-6-(2-methoxy-pyridin-3-yl)-1,2,3,4,4a,10b-hexahydro-phenanthridin-2-yl ester $C_{24}H_{28}N_2O_5$
Calc.: 424.5
Found (MH+): 425.2

159. Acetic acid (2RS,4aRS,10bRS)-9-ethoxy-8-methoxy-6-(1-methyl-1H-benzotriazol-5-yl)-1,2,3,4,4a,10b-hexahydro-phenanthridin-2-yl ester $C_{25}H_{28}N_4O_4$
Calc.: 448.53
Found (MH+): 449.2

160. Acetic acid (2RS,4aRS,10bRS)-9-ethoxy-8-methoxy-6-quinoxalin-5-yl-1,2,3,4,4a,10b-hexahydro-phenanthridin-2-yl ester $C_{26}H_{27}N_3O_4$
Calc.: 445.52
Found (MH+): 446.3

Starting from the appropriate ester compounds, which are mentioned or described explicitly below (compounds 163 to 164), or which can be prepared in a manner known to the person skilled in the art or analogously or similarly to the examples described herein, the following compounds 161 to 162 can be obtained according to the procedure as in Example 1.

161. (2RS,4aRS,10bRS)-8-(1,1-Difluoro-methoxy)-9-methoxy-6-pyridin-3-yl-1,2,3,4,4a,10b-hexahydro-phenanthridin-2-ol 162. (2RS,4aRS,10bRS)-8-(1,1-Difluoro-methoxy)-9-methoxy-6-(6-morpholin-4-yl-pyridin-3-yl)-1,2,3,4,4a,10b-hexahydro-phenanthridin-2-ol Starting from the corresponding starting compounds, which can be prepared in a manner known to the person skilled in the art—analogously or similarly to the starting compounds described herein below, the following compounds 163 to 164 can be obtained according to the procedure as in Example 18. If necessary, the cyclization reaction can be carried out in the presence of a catalytic amount of a Lewis acid such e.g. tin tetrachloride.

163. Acetic acid (2RS,4aRS,10bRS)-8-(1,1-difluoromethoxy)-9-methoxy-6-pyridin-3-yl-1,2,3,4,4a,10b-hexahydro-phenanthridin-2-yl ester $C_{22}H_{22}F_2N_2O_4$
Calc.: 416.43
Found (MH+): 417.3

164. Acetic acid (2RS,4aRS,10bRS)-8-(1,1-difluoromethoxy)-9-methoxy-6-(6-morpholin-4-yl-pyridin-3-0)-1,2,3,4,42,10b-hexahydro-phenanthridin-2-yl ester $C_{26}H_{29}F_2N_3O_5$
Calc.: 501.53
Found (MH+): 502.4

165. 5-((2R,4aR,10bR)-9-Ethoxy-2-hydroxy-8-methoxy-1,2,3,4,4a,10b-hexahydro-phenanthridin-6-yl)-pyridine-2-carboxylic acid Analogously as described for Example 35 acidic acid (2R,4aR,10bR)-6-(6-cyano-pyridin-3-yl)-9-ethoxy-8-methoxy-1,2,3,4,4a,10b-hexahydro-phenanthridin-2-yl ester (compound 172) is converted in a first step into the corresponding imino ester 5-((2R,4aR,10bR)-9-ethoxy-2-hydroxy-8-methoxy-1,2,3,4,4a,10b-hexahydro-phenanthridin-6-yl)-pyridine-2-carboximidic acid methyl ester. In a second step, 443 mg (1.08 mmol) of 5-((2R,4aR,10bR)-9-ethoxy-2-hydroxy-8-methoxy-1,2,3,4,4a,10b-hexahydro-phenanthridin-6-yl)-pyridine-2-carboximidic acid methyl ester are dissolved in 3 ml of THF. A solution of 51 mg (2.16 mmol) LiOH.H$_2$O is added and the solution stirred at 60° C. for 18 hrs. The pH is adjusted to 5 using phosphoric acid and Disodiumhydrogenphosphate. The solvent is removed and the solid residue extracted with chloroform/methanol. After filtering off and re-moving the volatiles 350 mg (82%) of the title compound are obtained.

$C_{22}H_{24}N_2O_6$
Calc.: 396.45
Found (MH+): 397.2

166. (2S,4aS,10bS)-6-(2,6-Dimethoxy-pyridin-3-yl)-8,9-dimethoxy-1,2,3,4,4a,10b-hexahydro-phenanthridin-2-ol The title compound can be obtained by chromatographical separation of the corresponding racemate (Example 42) using a column as described below at the end of the chapter "Final compounds".
$C_{22}H_{26}N_2O_6$
Calc.: 398.46
Found (MH+): 399.3

167. (2R,4aR,10bR)-6-(2,6-Dimethoxy-pyridin-3-yl)-8,9-dimethoxy-1,2,3,4,4a,10b-hexahydro-phenanthridin-2-ol The title compound can be obtained by chromatographical separation of the corresponding racemate (Example 42) using a column as described below at the end of the chapter "Final compounds".
$C_{22}H_{26}N_2O_6$
Calc.: 398.46
Found (MH+): 399.2

168. Acidic acid (2R,4aR,10bR)-6-(6-cyano-pyridin-3-yl)-9-ethoxy-8-methoxy-1,2,3,4,4a,10b-hexahydro-phenanthridin-2-yl ester Starting from compound A61 the title compound can be obtained analogously to Example 44.

169. (38R,4aRS,10bRS)-6-(2,6-Dimethoxy-pyridin-3-yl)-9-ethoxy-8-methoxy-1,2,3,4,4a,10b-hexahydro-phenanthridin-3-ol Starting from compound 170 the title compound can be obtained analogously to Example 1.

170. Acetic acid (3SR,4aRS,10bRS)-6-(2,6-dimethoxy-pyridin-3-yl)-9-ethoxy-8-methoxy-1,2,3,4,4a,10b-hexahydro-phenanthridin-3-yl ester Starting from the appropriate starting compounds mentioned below the title compound can be obtained analogously to example 85.

Starting from the appropriate compounds mentioned above and the appropriate acid the corresponding salts can be obtained, for example, according to the following general procedure, or analogously or similarly thereto:

About 1 g of the free base is solved in about 10 ml of a suitable solvent at room temperature. To this solution 1.1 eq. of the appropriate acid is added in one portion under stirring. The mixture is stirred over night while the salt precipitated. The salt is filtered off, washed with about 2 ml of the suitable solvent and dried over night at about 50° C. in vacuo. Thus, for example, in the case of hydrochloric acid an ether or alcohol solvent (e.g. dioxane, THF, diethylether, methanol, ethanol, or the like), or in the case of organic acids, such as e.g. fumaric, tartaric or oxoglutaric acid, a ketone solvent (e.g. acetone) may be suitable.

The following salts are obtained according to the above-mentioned procedure or analogously or similarly thereto:

(2R,4aR,10bR)-6-(2,6-Dimethoxy-pyridin-3-yl)-9-ethoxy-8-methoxy-1,2,3,4,4a,10b-hexa hydro-phenanthridin-2-ol hydrochloride (2R,4aR,10bR)-9-Ethoxy-8-methoxy-6-pyrimidin-5-yl-1,2,3,4,4a,10b-hexahydro-phenanthridin-2-ol hydrochloride (2R,4aR,10bR)-9-Ethoxy-8-methoxy-6-(6-pyrazol-1-yl-pyridin-3-yl)-1,2,3,4,4a,10b-hexahydro-phenanthridin-2-ol hydrochloride (2R,4a R,10bR)-9-Ethoxy-8-methoxy-6-(2-methoxy-pyrimidin-5-yl)-1,2,3,4,4a,10b-hexa hydro-phenanthridin-2-ol hydrochloride (2R,4aR,10bR)-6-(2,4-Dimethoxy-pyrimidin-5-yl)-9-ethoxy-8-methoxy-1,2,3,4,4a,10b-hexahydro-phenanthridin-2-ol hydrochloride (2R,4a R,10bR)-9-Ethoxy-8-methoxy-6-pyrazin-2-yl-1,2,3,4,4a,10b-hexahydro-phenanthridin-2-ol hydrochloride (2R,4aR,10bR)-6-(3,6-Dimethoxy-pyridazin-4-yl)-9-ethoxy-8-methoxy-1,2,3,4,4a,10b-hexa hydro-phenanthridin-2-ol hydrochloride (2R,4aR,10bR)-9-Ethoxy-8-methoxy-6-(6-methoxy-pyridin-3-yl)-1,2,3,4,4a,10b-hexahydro-phenanthridin-2-ol hydrochloride (2R,4a R,10bR)-6-(2-Dimethylamino-4-methoxy-pyrimidin-5-yl)-9-ethoxy-8-m ethoxy-1,2,3,4,4a,10b-hexahydro-phenanthridin-2-ol hydrochloride (2R,4aR,10bR)-6-(4,6-Dimethoxy-pyridin-3-yl)-9-ethoxy-8-methoxy-1,2,3,4,4a,10b-hexahydro-phenanthridin-2-ol hydrochloride (2R,4aR,10bR)-6-(2-Dimethylamino-pyrimidin-5-yl)-9-ethoxy-8-methoxy-1,2,3,4,4a,10b-hexahydro-phenanthridin-2-ol hydrochloride 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one hydrochloride 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one hydrochloride (2R,4aR,10bR)-6-(2,6-Dimethoxy-pyridin-3-yl)-9-ethoxy-8-methoxy-1,2,3,4,4a,10b-hexahydro-phenanthridin-2-ol sulfate (2R,4aR,10bR)-9-Ethoxy-8-methoxy-6-(2-methoxy-pyrimidin-5-yl)-1,2,3,4,4a,10b-hexahydro-phenanthridin-2-ol sulfate (2R,4aR,10bR)-6-(2,4-Dimethoxy-pyrimidin-5-yl)-9-ethoxy-8-methoxy-1,2,3,4,4a,10b-hexahydro-phenanthridin-2-ol sulfate (2R,4aR,10bR)-9-Ethoxy-6-(6-imidazol-1-yl-pyridin-3-yl)-8-methoxy-1,2,3,4,4a,10b-hexahydro-phenanthridin-2-ol sulfate (2R,4aR,10bR)-6-(3,6-Dimethoxy-pyridazin-4-yl)-9-ethoxy-8-methoxy-1,2,3,4,4a,10b-hexahydro-phenanthridin-2-ol sulfate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol sulfate (2R,4aR,10bR)-6-(4,6-Dimethoxy-pyridin-3-yl)-9-ethoxy-8-methoxy-1,2,3,4,4a,10b-hexahydro-phenanthridin-2-ol sulfate (2R,4aR,10bR)-6-(2-Dimethylamino-pyrimidin-5-yl)-9-ethoxy-8-methoxy-1,2,3,4,4a,10b-hexahydro-phenanthridin-2-ol sulfate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one sulfate (2R,4aR,10bR)-6-(2,6-Dimethoxy-pyridin-3-yl)-9-ethoxy-8-methoxy-1,2,3,4,4a,10b-hexahydro-phenanthridin-2-ol methanesulfonate (2R,4aR,10bR)-9-Ethoxy-8-methoxy-6-pyrimidin-5-yl-1,2,3,4,4a,10b-hexahydro-phenanthridin-2-ol methansulfonate (2R,4aR,10bR)-9-Ethoxy-8-methoxy-6-(2-methoxy-pyrimidin-5-yl)-1,2,3,4,4a,10b-hexahydro-phenanthridin-2-ol methansulfonate (2R,4aR,10bR)-6-(2,4-Dimethoxy-pyrimidin-5-yl)-9-ethoxy-8-methoxy-1,2,3,4,4a,10b-hexahydro-phenanthridin-2-ol methansulfonate (2R,4aR,10bR)-9-Ethoxy-6-(6-imidazol-1-yl-pyridin-3-yl)-8-methoxy-1,2,3,4,4a,10b-hexahydro-phenanthridin-2-ol methansulfonate (2R,4aR,10bR)-9-Ethoxy-8-methoxy-6-pyrazin-2-yl-1,2,3,4a,10b-hexahydro-phenanthridin-2-ol methansulfonate (2R,4aR,10bR)-6-(3,6-Dimethoxy-pyridazin-4-yl)-9-ethoxy-8-methoxy-1,2,3,4,4a,10b-hexahydro-phenanthridin-2-ol methansulfonate (2R,4aR,10bR)-9-Ethoxy-8-methoxy-6-(6-methoxy-pyridin-3-yl)-1,2,3,4,4a,10b-hexahydro-phenanthridin-2-ol methansulfonate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol methansulfonate (2R,4aR,10bR)-6-(4,6-Dimethoxy-pyridin-3-yl)-9-ethoxy-8-methoxy-1,2,3,4,4a,10b-hexahydro-phenanthridin-2-ol methansulfonate (2R,4aR,10bR)-6-(2-Dimethylamino-pyrimidin-5-yl)-9-ethoxy-8-methoxy-1,2,3,4,4a,10b-hexahydro-phenanthridin-2-ol methansulfonate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one methansulfonate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one methansulfonate (2R,4aR,10bR)-6-(2,6-Dimethoxy-pyridin-3-yl)-9-ethoxy-8-methoxy-1,2,3,4,4a,10b-hexahydro-phenanthridin-2-ol citrate (2R,4aR,10bR)-9-Ethoxy-8-methoxy-6-(6-pyrazol-1-yl-pyridin-3-yl)-1,2,3,4,4a,10b-hexahydro-phenanthridin-2-ol citrate (2R,4aR,10bR)-9-Ethoxy-8-methoxy-6-(2-methoxy-pyrimidin-5-yl)-1,2,3,4,4a,10b-hexahydro-phenanthridin-2-ol citrate (2R,4a R,10bR)-6-(2,4-Dimethoxy-pyrimidin-5-yl)-9-ethoxy-8-methoxy-1,2,3,4,4a,10b-hexa hydro-phenanthridin-2-ol citrate (2R,4aR,10bR)-9-Ethoxy-6-(6-imidazol-1-yl-pyridin-3-yl)-8-methoxy-1,2,3,4,4a,10b-hexahydro-phenanthridin-2-ol citrate (2R,4aR,10bR)-6-(3,6-Dimethoxy-pyridazin-4-yl)-9-ethoxy-8-methoxy-1,2,3,4,4a,10b-hexahydro-phenanthridin-2-ol citrate (2R,4aR,10bR)-9-Ethoxy-8-methoxy-6-(6-methoxy-pyridin-3-yl)-1,2,3,4,4a,10b-hexahydro-phenanthridin-2-ol citrate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol citrate (2R,4aR,10bR)-6-(4,6-Dimethoxy-pyridin-3-yl)-9-ethoxy-8-methoxy-1,2,3,4,4a,10b-hexahydro-phenanthridin-2-ol citrate (2R,4aR,10bR)-6-(2-Dimethylamino-pyrimidin-5-yl)-9-ethoxy-8-methoxy-1,2,3,4,4a,10b-hexa hydro-phenanthridin-2-ol citrate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one citrate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one citrate (2R,4aR,10bR)-6-(2,6-Dimethoxy-pyridin-3-yl)-9-ethoxy-8-methoxy-1,2,3,4,4a,10b-hexa hydro-phenanthridin-2-ol L-tartrate (2R,4aR,10bR)-9-Ethoxy-8-methoxy-6-pyrimidin-5-yl-1,2,3,4,4a,10b-hexahydro-phenanthridin-2-ol L-tartrate (2R,4aR,10bR)-9-Ethoxy-8-methoxy-6-(6-pyrazol-1-yl-pyridin-3-yl)-1,2,3,4,4a,10b-hexahydro-phenanthridin-2-ol L-tartrate (2R,4aR,10bR)-9-Ethoxy-8-methoxy-6-(2-methoxy-pyrimidin-5-yl)-1,2,3,4,4a,10b-hexahydro-phenanthridin-2-ol L-tartrate (2R,4aR,10bR)-6-(2,4-Dimethoxy-pyrimidin-5-yl)-9-ethoxy-8-methoxy-1,2,3,4,4a,10b-hexahydro-phenanthridin-2-ol L-tartrate (2R,4aR,10bR)-9-Ethoxy-8-methoxy-6-pyrazin-2-yl-1,2,3,4,4a,10b-hexahydro-phenanthridin-2-ol L-tartrate (2R,4aR,10bR)-6-(3,6-Dimethoxy-pyridazin-4-yl)-9-ethoxy-8-methoxy-1,2,3,4,4a,10b-hexahydro-phenanthridin-2-ol L-tartrate (2R,4aR,10bR)-9-Ethoxy-8-methoxy-6-(6-methoxy-pyridin-3-yl)-1,2,3,4,4a,10b-hexahydro-phenanthridin-2-ol L-tartrate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol L-tartrate (2R,4aR,10bR)-6-(4,6-Dimethoxy-pyridin-3-yl)-9-ethoxy-8-methoxy-1,2,3,4,4a,10b-hexahydro-phenanthridin-2-ol L-tartrate (2R,4aR,10bR)-6-(2-Dimethylamino-pyrimidin-5-yl)-9-ethoxy-8-methoxy-1,2,3,4,4a,10b-hexahydro-phenanthridin-2-ol L-tartrate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one L-tartrate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one L-tartrate (2R,4aR,10bR)-6-(2,6-Dimethoxy-pyridin-3-yl)-9-ethoxy-8-methoxy-1,2,3,4,4a,10b-hexahydro-phenanthridin-2-ol D-tartrate; m.p.: fnd.: decomposition starting at 107° C.

(2R,4aR,10bR)-9-Ethoxy-8-methoxy-6-(2-methoxy-pyrimidin-5-yl)-1,2,3,4,4a,10b-hexahydro-phenanthridin-2-ol D-tartrate (2R,4aR,10bR)-6-(2,4-Dimethoxy-pyrimidin-5-yl)-9-ethoxy-8-methoxy-1,2,3,4,4a,10b-hexahydro-phenanthridin-2-ol D-tartrate (2R,4aR,10bR)-9-Ethoxy-6-(6-imidazol-1-yl-pyridin-3-yl)-8-methoxy-1,2,3,4,4a,10b-hexahydro-phenanthridin-2-ol D-tartrate (2R,4aR,10bR)-9-Ethoxy-8-methoxy-6-pyrazin-2-yl-1,2,3,4,4a,10b-hexahydro-phenanthridin-2-ol D-tartrate (2R,4aR,10bR)-6-(3,6-Dimethoxy-pyridazin-4-yl)-9-ethoxy-8-methoxy-1,2,3,4,4a,10b-hexahydro-phenanthridin-2-ol D-tartrate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-tartrate (2R,4aR,10bR)-6-(4,6-Dimethoxy-pyridin-3-yl)-9-ethoxy-8-methoxy-1,2,3,4,4a,10b-hexahydro-phenanthridin-2-ol D-tartrate (2R,4aR,10bR)-6-(2-Dimethylamino-pyrimidin-5-yl)-9-ethoxy-8-methoxy-1,2,3,4,4a,10b-hexahydro-phenanthridin-2-ol D-tartrate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-tartrate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-tartrate (2R,4aR,10bR)-6-(2,6-Dimethoxy-pyridin-3-yl)-9-ethoxy-8-methoxy-1,2,3,4,4a,10b-hexahydro-phenanthridin-2-ol meso-tartrate (2R,4aR,10bR)-9-Ethoxy-8-methoxy-6-pyrimidin-5-yl-1,2,3,4,4a,10b-hexahydro-phenanthridin-2-ol meso-tartrate (2R,4aR,10bR)-9-Ethoxy-8-methoxy-6-(2-methoxy-pyrimidin-5-yl)-1,2,3,4,4a,10b-hexahydro-phenanthridin-2-ol mesa-tartrate (2R,4aR,10bR)-6-(2,4-Dimethoxy-pyrimidin-5-yl)-9-ethoxy-8-methoxy-1,2,3,4,4a,10b-hexahydro-phenanthridin-2-ol mesa-tartrate (2R,4aR,10bR)-9-Ethoxy-6-(6-imidazol-1-yl-pyridin-3-yl)-8-methoxy-1,2,3,4,4a,10b-hexahydro-phenanthridin-2-ol meso-tartrate (2R,4aR,10bR)-9-Ethoxy-8-methoxy-6-pyrazin-2-yl-1,2,3,4,4a,10b-hexahydro-phenanthridin-2-ol meso-tartrate (2R,4aR,10bR)-6-(3,6-Dimethoxy-pyridazin-4-yl)-9-ethoxy-8-methoxy-1,2,3,4,4a,10b-hexahydro-phenanthridin-2-ol meso-tartrate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol meso-tartrate (2R,4aR,10bR)-6-(4,6-Dimethoxy-pyridin-3-yl)-9-ethoxy-8-methoxy-1,2,3,4,4a,10b-hexahydro-phenanthridin-2-ol meso-tartrate (2R,4aR,10bR)-6-(2-Dimethylamino-pyrimidin-5-yl)-9-ethoxy-8-methoxy-1,2,3,4,4a,10b-hexahydro-phenanthridin-2-ol meso-tartrate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one meso-tartrate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one meso-tartrate (2R4a R,10bR)-6-(2,6-Dimethoxy-pyridin-3-yl)-9-ethoxy-8-methoxy-1,2,3,4,4a,10b-hexahydro-phenanthridin-2-ol D-malate (2R,4aR,10bR)-9-Ethoxy-8-methoxy-6-(6-pyrazol-1-yl-pyridin-3-yl)-1,2,3,4,4a,10b-hexahydro-phenanthridin-2-ol D-malate (2R,4aR,10bR)-9-Ethoxy-8-methoxy-6-(2-methoxy-pyrimidin-5-yl)-1,2,3,4,4a,10b-hexahydro-phenanthridin-2-ol D-malate (2R,4aR,10bR)-6-(2,4-Dimethoxy-pyrimidin-5-yl)-9-ethoxy-8-methoxy-1,2,3,4,4a,10b-hexahydro-phenanthridin-2-ol D-malate (2R,4aR,10bR)-6-(3,6-Dimethoxy-pyridazin-4-yl)-9-ethoxy-8-methoxy-1,2,3,4,4a,10b-hexahydro-phenanthridin-2-ol D-malate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-malate (2R,4aR,10bR)-6-(4,6-Dimethoxy-pyridin-3-yl)-9-ethoxy-8-methoxy-1,2,3,4,4a,10b-hexahydro-phenanthridin-2-ol D-malate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-malate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-malate (2R,4aR,10bR)-6-(2,6-Dimethoxy-pyridin-3-yl)-9-ethoxy-8-methoxy-1, 2,3,4,4a,10b-hexahydro-phenanthridin-2-ol L-malate (2R,4aR,10bR)-9-Ethoxy-8-methoxy-6-pyrimidin-5-yl-1,2,3,4,4a,10b-hexahydro-phenanthridin-2-ol malate (2R,4aR,10bR)-9-Ethoxy-8-methoxy-6-(2-methoxy-pyrimidin-5-yl)-1,2,3,4,4a,10b-hexahydro-phenanthridin-2-ol L-malate (2R,4aR,10bR)-6-(2,4-Dimethoxy-pyrimidin-5-yl)-9-ethoxy-8-methoxy-1,2,3,4,4a,10b-hexahydro-phenanthridin-2-ol L-malate (2R,4a R,10bR)-9-Ethoxy-6-(6-imidazol-1-yl-pyridin-3-yl)-8-methoxy-1,2,3,4,4a,10b-hexa hydro-phenanthridin-2-ol L-malate (2R,4aR,10bR)-6-(3,6-Dimethoxy-pyridazin-4-yl)-9-ethoxy-8-methoxy-1,2,3,4,4a,10b-hexahydro-phenanthridin-2-ol L-malate (2R,4a R,10b R)-6-(2-Dimethylamino-4-methoxy-pyrimidin-5-yl)-9-ethoxy-8-m ethoxy-1,2,3,4,4a,10b-hexahydro-phenanthridin-2-ol L-malate (2R,4aR,10bR)-6-(4,6-Dimethoxy-pyridin-3-yl)-9-ethoxy-8-methoxy-1,2,3,4,4a,10b-hexahydro-phenanthridin-2-ol L-malate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one L-malate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one L-malate (2R,4aR,10bR)-6-(2,6-Dimethoxy-pyridin-3-yl)-9-ethoxy-8-methoxy-1,2,3,4,4a,10b-hexahydro-phenanthridin-2-ol fumarate; m.p.: fnd.: decomposition starting at 172° C.

(2R,4aR,10bR)-9-Ethoxy-8-methoxy-6-pyrimidin-5-yl-1,2,3,4,4a,10b-hexahydro-phenanthridin-2-ol fumarate (2R,4aR,10bR)-9-Ethoxy-8-methoxy-6-(6-pyrazol-1-yl-pyridin-3-yl)-1,2,3,4,4a,10b-hexahydro-phenanthridin-2-ol fumarate (2R,4aR,10bR)-9-Ethoxy-8-methoxy-6-(2-methoxy-pyrimidin-5-yl)-1,2,3,4,4a,10b-hexahydro-phenanthridin-2-ol fumarate (2R,4aR,10bR)-6-(2,4-Dimethoxy-pyrimidin-5-yl)-9-ethoxy-8-methoxy-1,2,3,4,4a,10b-hexahydro-phenanthridin-2-ol fumarate (2R,4aR,10bR)-9-Ethoxy-6-(6-imidazol-1-yl-pyridin-3-yl)-8-methoxy-1,2,3,4,4a,10b-hexa hydro-phenanthridin-2-ol fumarate (2R,4aR,10bR)-6-(3,6-Dimethoxy-pyridazin-4-yl)-9-ethoxy-8-methoxy-1,2,3,4,4a,10b-hexahydro-phenanthridin-2-ol fumarate (2R,4aR,10bR)-9-Ethoxy-8-methoxy-6-(6-methoxy-pyridin-3-yl)-1,2,3,4,4a,10b-hexahydro-phenanthridin-2-ol fumarate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol fumarate (2R,4aR,10bR)-6-(4,6-Dimethoxy-pyridin-3-yl)-9-ethoxy-8-methoxy-1,2,3,4,4a,10b-hexahydro-phenanthridin-2-ol fumarate (2R,4aR,10bR)-6-(2-Dimethylamino-pyrimidin-5-yl)-9-ethoxy-8-methoxy-1,2,3,4,4a,10b-hexahydro-phenanthridin-2-ol fumarate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one fumarate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one fumarate (2R,4a R, 10bR)-6-(2,6-Dimethoxy-pyridin-3-yl)-9-ethoxy-8-methoxy-1,2,3,4,4a,10b-hexahydro-phenanthridin-2-ol maleinate (2R,4aR,10bR)-9-Ethoxy-8-methoxy-6-pyrimidin-5-yl-1,2,3,4,4a,10b-hexahydro-phenanthridin-2-ol maleinate (2R,4aR,10bR)-9-Ethoxy-8-methoxy-6-(2-methoxy-pyrimidin-5-yl)-1,2,3,4,4a,10b-hexahydro-phenanthridin-2-ol maleinate (2R,4a R, 10bR)-6-(2,4-Dimethoxy-pyrimidin-5-yl)-9-ethoxy-8-methoxy-1,2,3,4,4a,10b-hexahydro-phenanthridin-2-ol maleinate (2R,4aR,10bR)-9-Ethoxy-8-methoxy-6-pyrazin-2-yl-1,2,3,4,4a,10b-hexahydro-phenanthridin-2-ol maleinate (2R,4aR,10bR)-6-(3,6-Dimethoxy-pyridazin-4-yl)-9-ethoxy-8-methoxy-1,2,3,4,4a,1 b-hexahydro-phenanthridin-2-ol maleinate (2R,4aR,10bR)-9-Ethoxy-8-methoxy-6-(6-methoxy-pyridin-3-yl)-1,2,3,4,4a,10b-hexahydro-phenanthridin-2-ol maleinate (2R,4aR,10bR)-6-(2-Dimethylamino-4-methoxy-pyrimidin-5-yl)-9-ethoxy-8-m ethoxy-1,2,3,4,4a,10b-hexahydro-phenanthridin-2-ol maleinate (2R,4aR,10bR)-6-(4,6-Dimethoxy-pyridin-3-yl)-9-ethoxy-8-methoxy-1,2,3,4,4a,1 b-hexahydro-phenanthridin-2-ol maleinate (2R,4aR,10bR)-6-(2-Dimethylamino-pyrimidin-5-yl)-9-ethoxy-8-methoxy-1,2,3,4,4a,10b-hexahydro-phenanthridin-2-ol maleinate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one maleinate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one maleinate (2R,4aR,10bR)-6-(2,6-Dimethoxy-pyridin-3-yl)-9-ethoxy-8-methoxy-1,2,3,4,4a,10b-hexahydro-phenanthridin-2-ol oxoglutarate; m.p.: fnd.: decomposition starting at 110° C.

(2R,4aR,10bR)-9-Ethoxy-8-methoxy-6-pyrimidin-5-yl-1,2,3,4,4a,10b-hexahydro-phenanthridin-2-ol oxoglutarate (2R,4aR,10bR)-9-Ethoxy-8-methoxy-6-(6-pyrazol-1-yl-pyridin-3-yl)-1,2,3,4,4a,10b-hexahydro-phenanthridin-2-ol oxoglutarate (2R,4aR,10bR)-9-Ethoxy-8-methoxy-6-(2-methoxy-pyrimidin-5-yl)-1,2,3,4,4a,10b-hexahydro-phenanthridin-2-ol oxoglutarate (2R,4aR,10bR)-6-(2,4-Dimethoxy-pyrimidin-5-yl)-9-ethoxy-8-methoxy-1,2,3,4,4a,10b-hexahydro-phenanthridin-2-ol oxoglutarate (2R,4aR,10bR)-9-Ethoxy-6-(6-imidazol-1-yl-pyridin-3-yl)-8-methoxy-1,2,3,4,4a,10b-hexa hydro-phenanthridin-2-ol oxoglutarate (2R,4aR,10bR)-9-Ethoxy-8-methoxy-6-pyrazin-2-yl-1,2,3,4,4a,10b-hexahydro-phenanthridin-2-ol oxoglutarate (2R,4a R,10bR)-6-(3,6-Dimethoxy-pyridazin-4-yl)-9-ethoxy-8-methoxy-1,2,3,4,4a,10b-hexa hydro-phenanthridin-2-ol oxoglutarate (2R,4aR,10bR)-9-Ethoxy-8-methoxy-6-(6-methoxy-pyridin-3-yl)-1,2,3,4,4a,10b-hexahydro-phenanthridin-2-ol oxoglutarate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol oxoglutarate (2R,4aR,10bR)-6-(4,6-Dimethoxy-pyridin-3-yl)-9-ethoxy-8-methoxy-1,2,3,4,4a,10b-hexahydro-phenanthridin-2-ol oxoglutarate (2R,4aR,10bR)-6-(2-Dimethylamino-pyrimidin-5-yl)-9-ethoxy-8-methoxy-1,2,3,4,4a,10b-hexahydro-phenanthridin-2-ol oxoglutarate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one oxoglutarate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one oxoglutarate (2R,4aR,10bR)-6-(2,6-Dimethoxy-pyridin-3-yl)-9-ethoxy-8-methoxy-1,2,3,4,4a,10b-hexahydro-phenanthridin-2-ol oxalate (2R,4aR,10bR)-9-Ethoxy-8-methoxy-6-pyrimidin-5-yl-1,2,3,4,4a,10b-hexahydro-phenanthridin-2-ol oxalate (2R,4aR,10bR)-9-Ethoxy-8-methoxy-6-(2-methoxy-pyrimidin-5-yl)-1,2,3,4,4a,10b-hexahydro-phenanthridin-2-ol Oxalate (2R,4aR,10bR)-6-(2,4-Dimethoxy-pyrimidin-5-yl)-9-ethoxy-8-methoxy-1,2,3,4,4a,10b-hexahydro-phenanthridin-2-ol oxalate (2R,4aR,10bR)-9-Ethoxy-6-(6-imidazol-1-yl-pyridin-3-yl)-8-methoxy-1,2,3,4,4a,10b-hexahydro-phenanthridin-2-ol oxalate (2R,4aR,10bR)-6-(3,6-Dimethoxy-pyridazin-4-yl)-9-ethoxy-8-methoxy-1,2,3,4,4a,10b-hexahydro-phenanthridin-2-ol oxalate (2R,4aR,10bR)-6-(4,6-Dimethoxy-pyridin-3-yl)-9-ethoxy-8-methoxy-1,2,3,4,4a,10b-hexahydro-phenanthridin-2-ol oxalate (2R,4aR,10bR)-6-(2-Dimethylamino-pyrimidin-5-yl)-9-ethoxy-8-methoxy-1,2,3,4,4a,10b-hexahydro-phenanthridin-2-ol oxalate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one oxalate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one oxalate (2R,4a R,10bR)-6-(2,6-Dimethoxy-pyridin-3-yl)-9-ethoxy-8-methoxy-1,2,3,4,4a,10b-hexa hydro-phenanthridin-2-ol D-gluconate (2R,4a R,10bR)-9-Ethoxy-8-methoxy-6-pyrimidin-5-yl-1,2,3,4,4a,10b-hexahydro-phenanthridin-2-ol D-gluconate (2R,4aR,10bR)-9-Ethoxy-8-methoxy-6-(6-pyrazol-1-yl-pyridin-3-yl)-1,2,3,4,4a,10b-hexahydro-phenanthridin-2-ol D-gluconate (2R,4a R,10bR)-9-Ethoxy-8-methoxy-6-(2-methoxy-pyrimidin-5-yl)-1,2,3,4,4a,10b-hexa hydro-phenanthridin-2-ol D-gluconate (2R,4aR,10bR)-6-(2,4-Dimethoxy-pyrimidin-5-yl)-9-ethoxy-8-methoxy-1,2,3,4,4a,10b-hexahydro-phenanthridin-2-ol D-gluconate (2R,4a R,10bR)-9-Ethoxy-8-methoxy-6-pyrazin-2-yl-1,2,3,4,4a, 10b-hexa hydro-phenanthridin-2-ol D-gluconate (2R,4aR,10bR)-6-(3,6-Dimethoxy-pyridazin-4-yl)-9-ethoxy-8-methoxy-1,2,3,4,4a,10b-hexahydro-phenanthridin-2-ol D-gluconate (2R,4aR,10b R)-9-Ethoxy-8-methoxy-6-(6-methoxy-pyridin-3-yl)-1,2,3,4,4a,10b-hexa hydro-phenanthridin-2-ol D-gluconate (2R,4aR,10bR)-6-(2-Dimethylamino-4-methoxy-pyrimidin-5-yl)-9-ethoxy-8-methoxy-1,2,3,4,4a,10b-hexahydro-phenanthridin-2-ol D-gluconate (2R,4a R,10b R)-6-(4,6-Dimethoxy-pyridin-3-yl)-9-ethoxy-8-methoxy-1,2,3,4,4a,10b-hexa hydro-phenanthridin-2-ol D-gluconate 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one D-gluconate 5-((2R,4aR,10bR)-9-Ethoxy-2-hydroxy-8-methoxy-1,2,3,4,4a,10b-hexahydro-phenanthridin-6-yl)-1-methyl-1H-pyrimidin-2-one D-gluconate Optionally the abovementioned salts can be converted in a suitable solvent with the aid of a suitable base into the free compounds, which can be isolated in a manner known per se.

Chromatographical Separation:

Alternatively to the above described synthesis procedures using enantiomerically pure starting compounds, enantiomerically pure final compounds of formula I, in which either R41 or R51 is hydrogen, can be obtained from the corresponding racemates by chromatographical separation, which can be afforded with one or more of the following chiral columns:

CHIRALPAK® AD-H 5 µm (250×20 mm), 25° C., heptane/2-propanol/diethylamine=90/10/0.1; 20 ml/min, detection at 340 nm;

CHIRALPAK® AD 20 µm (285×110 mm), 30° C., acetonitrile/isopropanol=95:5; 570 ml/min, detection at 250 nm or 280 nm;

CHIRALPAK® AD 20 µm (250×50 mm), ambient temperature, heptane/isopropanol=95:5, 120 ml/min, detection at 330 nm; or CHIRALPAK® 50801 20 µm (250×50 mm), 25° C., methanol, 120 ml/min, detection at 330 nm.

Starting Materials

A1. Acetic acid (1RS,3RS,4RS)-4-{[1-(2,6-dimethoxy-pyridin-3-yl)methanoyl]amino}-3-(3-ethoxy-4-methoxyphenyl)cyclohexyl ester 555 mg of 2,6-dimethoxynicotinic acid and 581 mg of N-ethyl-N'-(3-dimethylaminopropyl)carbodiimide hydrochloride are placed in a flask under nitrogen. 778 mg of acetic acid (1 RS,3RS,4RS)-4-amino-3-(3-ethoxy-4-methoxyphenyl)cyclohexyl ester (compound B1) and 2 mg of 4-dimethylaminopyridine both as solution in dichloromethane are added and the solution stirred for 1 h at 40° C., than 42 h at room temperature. The reaction is quenched with 5 ml of water. After phase separation the organic layer is washed with 2.5 ml of saturated potassium hydrogencarbonate solution. After drying the organic layer with magnesium sulfate the solvent is removed to give 1.227 g of the crude title compound which are used for the following step without further purification.

MW: calc.: 472.54 MS: fnd: 473.1

Starting from the appropriate commercially available or art-known heteroaryl carboxylic acids and the appropriate compound B1, B2, B3, B4 or B5 further relevant, non-explicitly described starting compounds analogous to compound A1, which are also used to give via the abovementioned cyclization step the compounds mentioned above, are obtained according to the procedure as in Example A1.

The following compounds can be prepared from the appropriate starting compounds mentioned below and the appropriate commercially available or art-known heteroaryl carboxylic acids in a manner according to Example A1.

A2. Acetic acid (1RS,3RS,4RS)-3-(3-ethoxy-4-methoxy-phenyl)-4-{[1-(3-methyl-3H-imidazol-4-yl)-methanoyl]-amino}-cyclohexyl ester MW: calc.: 415.49 MS: fnd: 416.1

A3. Acetic acid (1RS,3RS,4RS)-3-(3-ethoxy-4-methoxy-phenyl)-4-{[1-(2-pyridin-3-yl-thiazol-4-yl)-methanoyl]-amino}-cyclohexyl ester MW: calc.: 495.60 MS: fnd: 496.0

A4. Acetic acid (1RS,3RS,4RS)-3-(3-ethoxy-4-methoxy-phenyl)-4-[(1-isoxazol-5-yl-methanoyl)-amino]-cyclohexyl ester MW: calc.: 402.45 MS: fnd: 402.8

A5. Acetic acid (1RS,3RS,4RS)-3-(3,4-dimethoxy-phenyl)-4-[(1-pyridin-4-yl-methanoyl)-amino]-cyclohexyl ester MW calc.: 398.46 MS: fnd: 399.2

A6. Acetic acid (1RS,3RS,4RS)-3-(3,4-dimethoxy-phenyl)-4-[(1-pyridin-3-yl-methanoyl)-amino]-cyclohexyl ester MW calc.: 398.46 MS: fnd: 399.2

A7. Acetic acid (1RS,3RS,4RS)-3-(3,4-dimethoxy-phenyl)-4-{[1-(6-morpholin-4-yl-pyridin-3-yl)-methanoyl]-amino}cyclohexyl ester MW calc.: 483.57 MS: fnd: 484.4

A8. Acetic acid (1RS,3RS,4RS)-4-[(1-benzo[1,2,5]oxadiazol-5-yl-methanoyl)-amino]-3-[3-(1,1-difluoro-methoxy)-4-methoxy-phenyl]-cyclohexyl ester MW calc.: 475.45 MS: fnd: 475.9

A9. Acetic acid (1RS,3RS,4RS)-4-[(1-benzo[1,2,6]oxadiazol-5-yl-methanoyl)-amino]-3-[3-(2,2-difluoro-ethoxy)-4-methoxy-phenyl]-cyclohexyl ester MW calc.: 489.48 MS: fnd: 489.9

A10. Acetic acid (1RS,3RS,4RS)-4-[(1-benzo[1,2,6]oxadiazol-5-yl-methanoyl)-amino]-3-[3-(2,2-difluoro-ethoxy)-4-methoxy-phenyl]-cyclohexyl ester MW calc.: 475.45 MS: fnd: 476.0

A11. Acetic acid (1RS,3RS,4RS)-4-[(1-2,3-dihydro-benzo[1,4]dioxin-6-yl-methanoyl)-amino]-3-(3-ethoxy-4-methoxy-phenyl)-cyclohexyl ester MW calc.: 469.54 MS: fnd: 470.1

A12. Acetic acid (1RS,3RS,4RS)-4-[(1-benzo[1,3]dioxol-5-yl-methanoyl)-amino]-3-(3-ethoxy-4-methoxy-phenyl)-cyclohexyl ester MW calc.: 455.51 MS: fnd: 456.1

A13. Acetic acid (1RS,3RS,4RS)-4-[(1-benzothiazol-6-yl-methanoyl)-amino]-3-(3-ethoxy-4-methoxy-phenyl)-cyclohexyl ester MW calc.: 468.58 MS: fnd: 469.0

A14. Acetic acid (1RS,3RS,4RS)-3-(3,4-dimethoxy-phenyl)-4-[(1-quinolin-6-yl-methanoyl)-amino]-cyclohexyl ester MW calc.: 448.52 MS: fnd: 449.3

A15. Acetic acid (1RS,3RS,4RS)-4-[{1-(2,2-difluoro-benzo[1,3]dioxol-5-yl)-methanoyl]-amino}-3-(3,4-dimethoxy-phenyl)-cyclohexyl ester MW calc.: 477.47 MS: fnd: 478.0

A16. Acetic acid (1RS,3RS,4RS)-4-[(1-benzo[1,2,5]oxadiazol-5-yl-methanoyl)-amino]-3-(3-ethoxy-4-methoxy-phenyl)-cyclohexyl ester MW calc.: 453.50 MS: fnd: 454.0

A17. Acetic acid (1RS,3RS,4RS)-3-(3-ethoxy-4-methoxy-phenyl)-4-{[1-(1-methyl-1H-imidazol-2-yl)-methanoyl]-amino}-cyclohexyl ester MW calc.: 415.49 MS: fnd: 416.1

A18. Acetic acid (1RS,3RS,4RS)-4-{[1-(6-cyano-pyridin-3-yl)-methanoyl]-amino}-3-(3-ethoxy-4-methoxy-phenyl)-cyclohexyl ester A19. Acetic acid (1RS,3RS,4RS)-3-[3-(2,2-difluoro-ethoxy)-4-methoxy-phenyl]-4-{[1-(2,6-dimethoxy-pyridin-3-yl)-methanoyl]-amino}-cyclohexyl ester MW calc.: 508.52 MS: fnd: 509.1

A20. Acetic acid (1RS,3RS,4RS)-3-[3-(2,2-difluoro-ethoxy)-4-methoxy-phenyl]-4-{[1-(2-methoxy-pyridin-3-yl)-methanoyl]-amino}-cyclohexyl ester MW calc.: 478.50 MS: fnd: 479.1

A21. Acetic acid (2RS,4aRS,10bRS)-9-(2,2-difluoro-ethoxy)-8-methoxy-6-(6-morpholin-4-yl-pyridin-3-yl)-1,2,3,4,4a,10b-hexahydro-phenanthridin-2-yl ester MW calc.: 533.58 MS: fnd: 534.3

A22. Acetic acid (1RS,3RS,4RS)-3-[3-(2,2-difluoro-ethoxy)-4-methoxy-phenyl]-4-[(1-pyridin-3-yl-methanoyl)-amino]-cyclohexyl ester MW calc.: 448.47

A23. Acetic acid (1RS,3RS,4RS)-3-[3-(2,2-difluoro-ethoxy)-4-methoxy-phenyl]-4-{[1-(2,6-dimethoxy-pyrimidin-4-yl)-methanoyl]-amino}-cyclohexyl ester MW calc.: 509.51

A24. Acetic acid (1RS,3RS,4RS)-3-[4-(2,2-difluoro-ethoxy)-3-methoxy-phenyl]-4-{[1-(2,6-dimethoxy-pyridin-3-yl)-methanoyl]-amino}-cyclohexyl ester MW calc.: 508.52 MS: fnd: 509.2

A25. Acetic acid (1RS,3RS,4RS)-3-(3,4-dimethoxy-phenyl)-4-{[1-(2,6-dimethoxy-pyridin-3-yl)-methanoyl]-amino}-cyclohexyl ester MW calc.: 458.52 MS: fnd: 459.1

A26. Acetic acid (1RS,3RS,4RS)-4-{[1-(2,6-dimethoxy-pyridin-4-yl)-methanoyl]-amino}-3-(3-ethoxy-4-methoxy-phenyl)-cyclohexyl ester MW calc.: 472.54 MS: fnd: 473.1

A27. Acetic acid (1RS,3RS,4RS)-4-amino-3-(5-(2,2-difluoro-ethoxy)-2-[1-(2,6-dimethoxy-pyridin-4-yl)-methanoyl]-4-methoxy-phenyl)-cyclohexyl ester MW calc.: 508.52

A28. Acetic acid (1R,3R,4R)-3-(3-ethoxy-4-methoxy-phenyl)-4-[1-pyrimidin-5-yl-methanoyl)-amino]-cyclohexyl ester MW calc.: 413.48 MS: fnd: 414.1

A29. Acetic acid (1R,3R,4R)-3-(3-ethoxy-4-methoxy-phenyl)-4-{[1-(6-pyrazol-1-yl-pyridin-3-yl)-methanoyl]-amino}-cyclohexyl ester MW calc.: 478.55

A30. Acetic acid (1R,3R,4R)-3-(3-ethoxy-4-methoxy-phenyl)-4-[(1-3,4,5,6-tetrahydro-2H-[1,2]bipyridinyl-5'-yl-methanoyl)-amino]-cyclohexyl ester MW calc.: 495.62 MS: fnd: 496.2

A31. 6-[(1R,2R,4R)-4-Acetoxy-2-(3-ethoxy-4-methoxy-phenyl)-cyclohexylcarbamoyl]-nicotinic acid methyl ester MW calc.: 470.53 MS: fnd: 471.2

A32. Acetic acid (1R,3R,4R)-3-(3-ethoxy-4-methoxy-phenyl)-4-{[1-(2-methoxy-pyrimidin-5-yl)-methanol]-amino}-cyclohexyl ester MW calc.: 443.50 MS: fnd: 444.2

A33. Acetic acid (1R,3R,4R)-3-(3-ethoxy-4-methoxy-phenyl)-4-{[1-(2,4,6-trimethoxy-pyrimidin-5-yl)-methanoyl]-amino}cyclohexyl ester MW calc.: 503.65 MS: fnd: 504.2

A34. Acetic acid (1R,3R,4R)-4-{[1-(2,4-dimethoxy-pyrimidin-5-yl)-methanoyl]-amino}-3-(3-ethoxy-4-methoxy-phenyl)-cyclohexyl ester MW calc.: 473.53 MS: fnd: 474.2

A35. Acetic acid (1R,3R,4R)-4-([1-(2,4-dimethoxy-pyrimidin-5-yl)-methanoyl]-amino)-3-(3-ethoxy-4-methoxy-phenyl)-cyclohexyl ester MW calc.: 427.50 MS: fnd: 428.2

A36. Acetic acid (1R,3R,4R)-4-([1-(2,6-dimethoxy-pyrimidin-4-yl)-methanoyl]-amino)-3-(3-ethoxy-4-methoxy-phenyl)-cyclohexyl ester MW calc.: 473.53 MS: fnd: 474.1

A37. Acetic acid (1R,3R,4R)-3-(3-ethoxy-4-methoxy-phenyl)-4-{[1-(6-imidazol-1-yl-pyridin-3-yl)-methanoyl]-amino}cyclohexyl ester MW calc.: 478.55 MS: fnd: 479.3

A38. Acetic acid (1R,3R,4R)-3-(3-ethoxy-4-methoxy-phenyl)-4-[(1-pyrazin-2-yl-methanoyl)-amino]-cyclohexyl ester MW calc.: 413.48 MS: fnd: 414.2

A39. Acetic acid (1R,3R,4R)-3-(3-ethoxy-4-methoxy-phenyl)-4-[(1-pyrazin-2-yl-methanoyl)-amino]-cyclohexyl ester MW calc.: 466.54

A40. Acetic acid (1R,3R,4R)-3-(3-ethoxy-4-methoxy-phenyl)-4-([1-(4-methoxy-1,3-dimethyl-1H-pyrazolo[3,4-b]pyridin-5-yl)-methanoyl]-amino)-cyclohexyl ester MW calc.: 510.60 MS: fnd: 511.2

A41. Acetic acid (1R,3R,4R)-4-{[1-(2,6-dimethoxy-pyridin-3-yl)-methanoyl]-amino}-3-(3-ethoxy-4-methoxy-phenyl)-cyclohexyl ester MW calc.: 472.54 MS: fnd: 473.2

A42. Acetic acid (1SR,3RS,4RS)-4-(3,4-dimethoxy-phenyl)-3-[(1-pyridin-3-yl-methanoyl)-amino]-cyclohexyl ester MW calc.: 398.46 MS: fnd: 399.2

A43. Acetic acid (1R,3R,4R)-3-(3-ethoxy-4-methoxy-phenyl)-4-([1-(2-methylsulfanyl-pyridin-3-yl)-methanoyl]-amino)-cyclohexyl ester A44. Acetic acid (1R,3R,4R)-3-(3-ethoxy-4-methoxy-phenyl)-4-{[1-(4-methyl-2-methylsulfanyl-pyrimidin-5-yl)-methanoyl]-amino}-cyclohexyl ester A45. Acetic add (1R,3R,4R)-4-{[1-(5-chloro-2-methylsulfanyl-pyrimidin-4-yl)-methanoyl]-amino}-3-(3-ethoxy-4-methoxy-phenyl)-cyclohexyl ester A46. Acetic acid (1R,3R,4R)-3-(3-ethoxy-4-methoxy-phenyl)-4-{[1-(2-methoxy-pyridin-3-yl)-methanoyl]-amino}-cyclohexyl ester A47. Acetic add (1R,3R,4R)-3-(3-ethoxy-4-methoxy-phenyl)-4-{[1-(1-methyl-6-oxo-1,6-dihydro-pyridin-3-yl) methanoyl]-amino}-cyclohexyl ester A48. Acetic acid (1R,3R,4R)-3-(3-ethoxy-4-methoxy-phenyl)-4-{[1-(6-methoxy-pyridin-3-yl)-methanoyl]-amino}-cyclohexyl ester A49. Acetic acid (1R,3R,4R)-4-{[1-(2-dimethylamino-4-oxo-1,6-dihydro-pyrimidin-5-yl)-methanoyl]-amino}-3-(3-ethoxy-4-methoxy-phenyl)-cyclohexyl ester A50. Acetic acid (1R,3R,4R)-4-{[1-(2-dimethylamino-4-methoxy-pyrimidin-5-yl)-methanoyl]-amino}-3-(3-ethoxy-4-methoxy-phenyl)-cyclohexyl ester A51. Acetic acid (1R,3R,4R)-4-{[1-(4,6-diethoxy-pyridin-3-yl)-methanoyl]-amino}-3-(3-ethoxy-4-methoxy-phenyl)-cyclohexyl ester A52. Acetic acid (1R,3R,4R)-4-{[1-(4,6-dimethoxy-pyridin-3-yl)-methanoyl]-amino}-3-(3-ethoxy-4-methoxy-phenyl)-cyclohexyl ester A53. Acetic acid (1R,3R,4R)-4-{[1-(2-dimethylamino-pyrimidin-5-yl)-methanoyl]-amino}-3-(3-ethoxy-4-methoxy-phenyl)-cyclohexyl ester A54. Acetic acid (1R,3R,4R)-4-{[1-(5,6-dimethoxy-pyridin-3-yl)-methanoyl]-amino}-3-(3-ethoxy-4-methoxy-phenyl)-cyclohexyl ester A55. Acetic acid (1R,3R,4R)-4-{[1-(5-ethoxy-6-methoxy-pyridin-3-yl)-methanoyl]-amino}-3-(3-ethoxy-4-methoxy-phenyl)-cyclohexyl ester A56. Acetic acid (1R,3R,4R)-4-{[1-(2-methylsulfanyl-pyrimidin-5-yl)-methanoyl]-amino}-3-(3-ethoxy-4-methoxy-phenyl)-cyclohexyl ester A57. Acetic acid (1R,3R,4R)-3-(3-ethoxy-4-methoxy-phenyl)-4-{[1-(1-methyl-2-oxo-1,2-dihydro-pyrimidin-5-yl)-methanoyl]-amino}-cyclohexyl ester A58. Acetic acid (1R,3R,4R)-3-(3-ethoxy-4-methoxy-phenyl)-4-{[1-(6-hydroxy-pyridin-3-yl)-methanoyl]-amino}-cyclohexyl ester A59. Acetic acid (1R,3R,4R)-3-(3-ethoxy-4-methoxy-phenyl)-4-{[1-(3,6-dimethoxy-pyridazin-4-yl)-methanoyl]-amino}-cyclohexyl ester A60. Acetic acid (1R,3R,4R)-3-(3-ethoxy-4-methoxy-phenyl)-4-{([1-(4,6-dimethoxy-pyrimidin-5-yl)-methanoyl]-amino}-cyclohexyl ester A61. Acetic acid (1R,3R,4R)-4-{[1-(6-cyano-pyridin-3-yl)-methanoyl]-amino}-3-(3-ethoxy-4-methoxy-phenyl)-cyclohexyl ester Further relevant starting compounds for the final examples mentioned above can be prepared from the appropriate starting compounds mentioned below and the appropriate commercially available or art-known heteroaryl carboxylic acids in a manner according to Example A1.

B1. Acetic acid (1RS,3RS,4RS)-4-amino-3-(3-ethoxy-4-methoxy-phenyl)-cyclohexyl ester Starting from compound C1 mentioned below, the title compound is obtained analogously to the procedure as in Example B2.
EF: $C_{17}H_{25}NO_4$; MW: 307.39
MS: 308.0 (MH$^+$)

B1a. Acetic acid (1R,3R,4R)-4-amino-3-(3-ethoxy-4-methoxy-phenyl)-cyclohexyl ester 24.0 g (55.0 mmol) of the pyroglutamate of the title compound (compound Bib) are suspended in 150 ml of water, 100 ml of dichloromethane are added, then saturated $KHCO_3$-solution until the gas evolution ceased. After phase separation, reextraction of the water layer and drying the combined organic layers with sodium sulfate the solvent is removed to give 16.9 g of the salt-free title compound. Analytical Column Chromatography (CHIRALPAK AD-H 250×4.6 mm 5μ No.ADHOCE-DB030, Eluent: n-Hexan/iPrOH=80/20 (v/v)+0.1% Diethylamine): Retention Time: 6.54 min B1b. Acetic acid (1R,3R,4R)-4-amino-3-(3-ethoxy-4-methoxy-phenyl)-cyclohexyl ester, ome with L-pyroglutamic acid Solution A: 55.2 g (180 mmol) of racemic acetic acid (1RS,3RS,4RS)-4-amino-3-(3-ethoxy-4-methoxy-phenyl)-cyclohexylester (compound 131) are dissolved in 540 ml of isopropyl acetate.
Solution B: 18.6 g (144 mmol) of L-pyroglutamic acid are dissolved in 260 ml of isopropanol under heating, then 290 ml of isopropyl acetate is added carefully.
Solution B is added to solution A and left for 48 hours. The solid is filtered off and washed with a little isopropyl acetate to give after drying 32.48 g colorless crystals with a ratio of the enantiomers of 97:3 in favour of the title compound.
M.p.: 165-167° C.

B2. Acetic acid (1RS,3RS,4RS)-4-amino-3-(3,4-dimethoxyphenyl)cyclohexyl ester

A solution of 10.37 g of acetic acid (1RS,3RS,4RS)-3-(3,4-dimethoxyphenyl)-4-nitrocyclohexyl ester (compound 02) in 240 ml of ethanol is added to a zinc-copper couple, prepared from 16.8 g of zinc powder and 920 mg of copper (II) acetate monohydrate in acetic acid, the resulting suspension is refluxed and treated with 26 ml of acetic acid, 3.2 ml of water and 26 ml of ethanol. The resulting mixture is refluxed for further 15 min. The precipitate is filtered off with suction and the solvent is removed. Chromatographical purification on silica gel using a mixture of petroleum ether/ethyl acetate/triethylamine in the ratio 21711 and concentration of the corresponding eluate fractions afford 5.13 g (55% of theory) of the title compound as a pale brown oil.
$R_f$=0.35 (petroleum ether/ethyl acetate/triethylamine=2/7/1)

B3. Acetic acid (1RS,3RS,4RS)-4-amino-3-[4-(1,1-difluoro-methoxy)-3-methoxy-phenyl]-cyclohexyl ester Starting from compound C3 mentioned below, the title compound is obtained analogously to the procedure as in Example B2.
EF: $C_{16}H_{21}F_2NO_4$; MW: 329.35
MS: 330.0 (MH$^+$)

B4. Acetic acid (1RS,3RS,4RS)-4-amino-3-[3-(1,1-difluoro-methoxy)-4-methoxy-phenyl]-cyclohexyl ester Starting from compound C4 mentioned below, the title compound is obtained analogously to the procedure as in Example B2.
EF: $C_{16}H_{21}F_2NO_4$; MW: 329.35
MS: 330.0 ($MH^+$)

B5. Acetic acid (1RS,3RS,4RS)-4-amino-3-[3-(2,2-difluoro-ethoxy)-4-methoxy-phenyl]-cyclohexyl ester Starting from compound C5 mentioned below, the title compound is obtained analogously to the procedure as in Example B2.

B5a. Acetic acid (1R,3R,4R)-4-amino-3-[3-(2,2-difluoro-ethoxy)-4-methoxy-phenyl]-cyclohexyl ester The title compound is obtained from its pyroglutamate salt (compound B5b) analogously as described for compound B1a using sodium hydrogencarbonate solution.

B5b. Acetic acid (1R,3R,4R)-4-amino-3-[3-(2,2-difluoro-ethoxy)-4-methoxy-phenyl]-cyclohexyl ester, salt with L-pyroglutamic acid 343 mg (1.00 mmol) of acetic acid (1RS,3RS,4RS)-4-amino-3-[3-(2,2-difluoro-ethoxy)-4-methoxy-phenyl]-cyclohexyl ester (compound B5) are dissolved in 3 ml of isopropanol. A solution of 103 mg (0.80 mmol) of L-pyroglutamic acid in 2 ml of isopropanol is added. After filtering and drying 162 mg of the pyroglutamate are isolated with an enantiomeric ratio of 97:3 in favour of the title compound.

B6. Acetic acid (1SR,3RS,4RS)-3-amino-4-(3-ethoxy-4-methoxy-phenyl)-cyclohexyl ester 3.0 g (7.36 mmol) of acetic acid (1SR,3RS,4RS)-3-tert-butoxycarbonylamino-4-(3-ethoxy-4-methoxy-phenyl)-cyclohexyl ester (compound C6) are dissolved in 6 ml of 4 M HCl in dioxane and stirred for 30 min. After removal of the solvent the residue is dissolved in dichloromethane and 25 ml of sat. Na—$HCO_3$ solution are added carefully. After phase separation, reextraction of the water layer and drying of the combined organic layers ($Na_2SO_4$) the solvent is removed to give 2.25 g of the title compound.
EF: C17H25N O4; MW: 307.39
MS: 308.1 ($MH^+$)

B7. Acetic acid (1SR,3RS,4RS)-3-amino-4-(3,4-dimethoxy-phenyl)-cyclohexyl ester The title compound can be obtained from compound C7 analogously as described for compound B6.

C1. Acetic acid (1RS,3RS,4RS)-3-(3-ethoxy-4-methoxy-phenyl)-4-nitrocyclohexyl ester Starting from compound D1 mentioned below, the title compound is obtained according to the procedure as in Example C2.

C2. Acetic acid (1RS,3RS,4RS)-3-(3,4-dimethoxyphenyl)-4-nitrocyclohexyl ester 10.18 g of (1 RS,3RS,4RS)-3-(3,4-dimethoxyphenyl)-4-nitrocyclohexanol (compound D2) are dissolved in 100 ml of acetic anhydride and the solution is heated to 100° C. for 1-2 h. After removal of the solvent, the residue is chromatographed on silica gel using a mixture of petroleum ether/ethyl acetate in the ratio 2/1. Concentration of the corresponding eluate fractions furnish 10.37 g (89% of theory) of the title compound as an oil.
$R_f$=0.32 (petroleum ether/ethyl acetate=2/1)
Starting from the starting compounds mentioned below, the following are obtained according to the procedure as in Example C2:

C3. Acetic acid (1RS,3RS,4RS)-3-[4-(1,1-difluoro-methoxy)-3-methoxy-phenyl]-4-nitrocyclohexyl ester

C4. Acetic acid (1RS,3RS,4RS)-3-[3-(1,1-difluoro-methoxy)-4-methoxy-phenyl]-4-nitrocyclohexyl ester

C5. Acetic acid (1RS,3RS,4RS)-3-(3-(2,2-difluoro-ethoxy)-4-methoxy-phenyl]-4-nitrocyclohexyl ester

C6. Acetic acid (1SR,3RS,4RS)-3-tert-butoxycarbonylamino-4-(3-ethoxy-4-methoxy-phenyl)-cyclohexyl ester 22.64 g (65 mmol) of [(1 RS,6RS)-6-(3-ethoxy-4-methoxy-phenyl)-cyclohex-3-enyl]-carbamic acid tert-butyl ester (compound D6) are dissolved in 180 ml of THF and 50 ml of $BH_3$ (1 M solution in THF) are added dropwise (30 min). After stirring for 2 h the mixture is cooled using an ice bath and a mixture of 30 ml of $H_2O_2$ (30%) and 60 ml of aqueous NaOH (3 M) is added. The mixture is stirred for 30 min at room temperature. 400 ml of water and 200 ml of dichloromethane are added. After phase separation, reextraction of the water layer and drying of the combined organic layers ($Na_2SO_4$) the solvent is removed and the crude product (23.42 g, mixture of the two mentioned regioisomers 2:1 in favour of the title compound) is used directly without further purification.

The crude material from above then is dissolved in 50 ml of pyridine. 50 mg of 4-dimethylaminopyridine and 60 ml of acetic anhydride are added and the mixture stirred for 90 min at 100° C. The solvents and the acetic anhydride are removed (sat. $NaHCO_3$ solution). Purification by means of chromatography yields 9.4 g of the title compound as colorless foam.
EF: C22H33N O6; MW: 407.51
MS: 308.1 ($MH^+$-Boc), 407.8 ($MH^+$), 430.1 ($Mna^+$)

C7. Acetic acid (1SR,3RS,4RS)-3-tert-butoxycarbonylamino-4-(3,4-dimethoxy-phenyl)-cyclohexyl ester The title compound can be obtained from compound D7 analogously as described for compound C6.

D1. (1 RS,3RS,4RS)-3-(3-Ethoxy-4-methoxy-phenyl)-4-nitrocyclohexanol

Starting from compound E1 mentioned below, the title compound is obtained according to the procedure as in Example D2.

D2. (1RS,3RS,4RS)-3-(3,4-Dimethoxyphenyl)-4-nitrocyclohexanol 10 g of (1RS,3RS,4SR)-3-(3,4-dimethoxyphenyl)-4-nitrocyclohexanol (compound E2) are dissolved in 170 ml of absolute 1,2-dimethoxyethane. 14.3 ml of a 30% solution of sodium methanolate in methanol are added dropwise. After complete addition, stirring is continued for 10 min and a mixture consisting of 85% phosphoric acid and methanol is added to pH 1. By adding of saturated potassium hydrogencarbonate solution the resulting suspension is neutralized. The mixture is diluted with water and dichloromethane, the organic layer is separated and extracted with dichloromethane. The solvents are removed under reduced pressure to yield the title compound as a pale yellow oil, which crystallizes. The title compound is used without further purification in the next step.

$R_f$=0.29 (petroleum ether/ethyl acetate=1/1)
M.p.: 126-127° C.

Starting from the appropriate starting compounds mentioned below, the following are obtained according to the procedure as in Example D2:

D3. (1RS,3RS,4RS)-3-[4-(1,1-Difluoro-methoxy)-3-methoxy-phenyl]-4-nitrocyclohexanol

D4. (1RS,3RS,4RS)-3-[3-(1,1-Difluoro-methoxy)-4-methoxy-phenyl]-4-nitrocyclohexanol

D5. (1RS,3RS,4RS)-3-(3-(2,2-Difluoro-ethoxy)-4-methoxy-phenyl)-4-nitrocyclohexanol

D6. [(1RS,6RS)-6-(3-Ethoxy-4-methoxy-phenyl)-cyclohex-3-enyl]-carbamic acid tert-butyl ester Starting from (1 RS,6RS)-6-(3-ethoxy-4-methoxy-phenyl)-cyclohex-3-enylamine (compound E6) the title compound is obtained analogously as described for compound D7.

EF: C20H29N O4; MW: 347.46,
MS: 370.1 (Mna$^+$)

D7. [(1RS,6RS)-6-(3,4-Dimethoxy-phenyl)-cyclohex-3-enyl]-carbamic acid tert-butyl ester 15.18 g (65.06 mmol) of (±)-cis-6-(3,4-dimethoxyphenyl)-cyclohex-3-enylamine (compound E7) and 14.21 g (65.11 mmol) of Boc$_2$O are stirred in dichloromethane for 2.5 h, then the solvent is removed and the residue crystallized from ethylacetate/n-heptane to give 19.1 g of the title compound.

EF: C19H27N O4; MW: 333.43,
MS: 334.2 (MH$^+$)

E1. (1 RS,3RS,4SR)-3-(3-Ethoxy-4-methoxy-phenyl)-4-nitrocyclohexanol

Starting from compound F1 mentioned below, the title compound is obtained according to the procedure as in Example E2.

E2. (1 RS,3RS,4SR)-3-(3,4-Dimethoxyphenyl)-4-nitrocyclohexanol

Under nitrogen atmosphere 16.76 g of (3RS,4SR)-3-(3,4-dimethoxyphenyl)-4-nitrocyclohexanone (compound F2) are dissolved in 300 ml of tetrahydrofurane, the solution is cooled to 78° C., and 75 ml of 1 M solution of potassium tri-sec-butylborohydride in tetrahydrofurane is added dropwise. After stirring for further 1 h, a mixture consisting of 30% hydrogeneperoxide solution and phosphate buffer solution is added. Stirring is continued for further 10 min, the reaction mixture is diluted with 400 ml of ethyl acetate and the aqueous layer is extracted with ethyl acetate, the combined organic phases are concentrated to give a foam, which is purified by chromatography on silica gel using a mixture of petroleum ether/ethyl acetate in the ratio 1/1 to furnish 10.18 g (60% of theory) of the title compound.

EF: $C_{14}H_{19}NO_6$; MW: 281.31
MS: 299.1 (MNH$_4^+$)
$R_f$=0.29 (petroleum ether/ethyl acetate=1/1)
M.p.: 139-141° C.

Starting from the appropriate starting compounds mentioned below, the following are obtained according to the procedure as in Example E2:

E3. (1RS,3RS,4SR)-3-[4-(1,1-Difluoro-methoxy)-3-methoxy-phenyl]-4-nitrocyclohexanol

E4. (1RS,3RS,4SR)-3-[3-(1,1-Difluoro-methoxy)-4-methoxy-phenyl]-4-nitrocyclohexanol

E5. (1RS,3RS,4SR)-3-(3-(2,2-Difluoro-ethoxy)-4-methoxy-phenyl)-4-nitrocyclohexanol

E6. (1RS,6RS)-6-(3-Ethoxy-4-methoxy-phenyl)-cyclohex-3-enylamine

Starting from 2-ethoxy-1-methoxy-4-((1RS,6RS)-6-nitro-cyclohex-3-enyl)-benzene (compound F6) the title compound is obtained analogously as described for compound E7.

E7. (±)-cis-6-(3,4-Dimethoxyphenyl)-cyclohex-3-enylamine 40 g of (±)-cis-1,2-dimethoxy-4-(2-nitrocyclohex-4-enyl)benzene (compound F7) are dissolved in 400 ml of ethanol and 40 g of zinc powder are added. After heating to boiling temperature, 65 ml of glacial acetic acid are added dropwise. Afterwards, the reaction mixture is filtrated and concentrated. The residue is redissolved in diluted hydrochloric acid and extracted with toluene. The aqueous layer is alkalized using 6 N solution of sodium hydroxide and extracted several times with toluene. The combined organic phases of the alkalic extraction are dried using sodium sulfate and concentrated. The residue is chromatographed on silica gel. 11.5 g of the title compound are obtained.

F1. (3RS,4SR)-3-(3-Ethoxy-4-methoxy-phenyl)-4-nitrocyclohexanone

Starting from compound G1 mentioned below, the title compound is obtained according to the procedure as in Example F2.

F2. (3RS,4SR)-3-(3,4-Dimethoxyphenyl)-4-nitrocyclohexanone 90.0 g of 3,4-dimethoxy-ω-nitrostyrene (compound G2), 90 ml of 2-trimethylsilyloxy-1,3-butadiene and 180 ml of abs. Toluene are put in an autoclave, where the mixture is stirred at 140° C. for 2 days and then cooled. After addition of 1000 ml of ethyl acetate, 300 ml of a 2 N solution of hydrochloric acid are dropped under stirring. The phases are separated and the aqueous layer is extracted three times with dichloromethane. The combined organic extracts are washed with saturated sodium hydrogencarbonate solution, dried over magnesium sulfate and the solvents are removed under reduced pressure to give 150 g of the crude title compound. Further purification is carried out by chromatography on silica gel using petroleum ether/ethyl acetate in the ratio 1/1 as eluent to give 81.5 g (67% of theory) of the pure title compound.

EF: $C_{14}H_{17}N_5$; MW: 279.30
MS: 279 ($M^+$), 297.1 ($MNH_4^+$)
$R_f$=0.47 (petroleum ether/ethyl acetate=1/1)
M.p.: 147-148° C.

Starting from the appropriate starting compounds mentioned below, the following are obtained according to the procedure as in Example F2:

F3. (3RS,4SR)-3-[4-(1,1-Difluoro-methoxy)-3-methoxy-phenyl]-4-nitrocyclohexanone F4. (3RS,4SR)-3-[3-(1,1-Difluoro-methoxy)-4-methoxy-phenyl]-4-nitrocyclohexanone F5. (3RS,4SR)-3-(3-(2,2-Difluoro-ethoxy)-4-methoxy-phenyl)-4-nitrocyclohexanone F6. 2-Ethoxy-1-methoxy-4-((1RS,6RS)-6-nitro-cyclohex-3-enyl)-benzene Starting from 2-ethoxy-1-methoxy-4-((1 RS,6SR)-6-nitro-cyclohex-3-enyl)-benzene (compound G6) the title compound is obtained analogously as described for compound F7.

F7. (±)-cis-1,2-Dimethoxy-4-(2-nitrocyclohex-4-enyl)benzene 10.0 g of (±)-trans-1,2-dimethoxy-4-(2-nitrocyclohex-4-enyl)benzene (compound G7) and 20.0 g of potassium hydroxide are dissolved in 150 ml of ethanol and 35 ml of dimethylformamide. A solution of 17.5 ml of conc. Sulfuric acid in 60 ml of ethanol is then added dropwise such that the internal temperature does not exceed 4° C. After stirring for 1 h, the mixture is added to 1 l of ice water, the precipitate is filtered off with suction, washed with water and dried, and the crude product is recrystallized in ethanol. 8.6 g of the title compound of m.p. 82.5-84° C. are obtained.

G1. 3-Ethoxy-4-methoxy-ω-nitrostyrene

Starting from art-known staffing compounds, the title compound is obtained according to the procedure as in Example G2:

G2. 3,4-Dimethoxy-ω-nitrostyrene 207.0 g of 3,4-dimethoxybenzaldehyde, 100.0 g of ammonium acetate and 125 ml of nitromethane are heated to boiling for 3-4 h in 1.0 l of glacial acetic acid. After cooling in an ice bath, the precipitate is filtered off with suction, rinsed with glacial acetic acid and petroleum ether and dried. M.p.: 140-141° C.

Yield: 179.0 g.

Starting from starting compounds, which are art-known or which can be obtained analogously to art-known compounds or according to art-known procedures (such as e.g. as described in WO 95/01338 or analogously or similarly thereto) the following compounds are obtained according to the procedure as in Example G2:

G3. 4-(1,1-Difluoro-methoxy)-3-methoxy-ω-nitrostyrene

G4. 3-(1,1-Difluoro-methoxy)-4-methoxy-ω-nitrostyrene

G5. 3-(2,2-Difluoro-ethoxy-4)-methoxy-ω-nitrostyrene

The title compound is obtained starting from 3-(2,2-difluoro-ethoxy)-4-methoxy-benzaldehyde (compound H1) according to the procedure as in Example G2.
M.p.: 164-165° C.

G6. 2-Ethoxy-1-methoxy-4-((1RS,6SR)-6-nitro-cyclohex-3-enyl)-benzene

Starting from 3-ethoxy-4-methoxy-ω-nitrostyrene (compound G1) the title compound is obtained analogously as described for compound G7.

G7. (±)-trans-1,2-Dimethoxy-4-(2-nitrocyclohex-4-enyl)benzene 50.0 g of 3,4-dimethoxy-ω-nitrostyrene (compound G2), and 1.0 g (9.1 mmol) of hydroquinone are suspened in 200 ml of abs. Toluene and treated at 70° C. with 55.0 g (1.02 mol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol. M.p.: 113.5-115.5° C.

H1. 3-(2,2-Difluoro-ethoxy)-4-methoxy-benzaldehyde 10.04 g of isovanillin and 15.5 g of potassium carbonate are placed in an autoclave. 50 ml of DMF are added as well as 12.44 g of 2-bromo-1,1-difluoroethane. The autoclave is closed and heated at 60° C. for 20 h. Then the solids are filtered off and washed with 120 ml of DMF. About 120 ml of the solvent are distilled off and the residue poured on 200 ml of ice/water, where the product precipitates. After stirring the slurry for 30 minutes the product is filtered off and dried to give 13.69 g of the desired product.
M.p.: 66-68° C.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insuffi-ciency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiin-farct dementia; and also illnesses of central nervous system, such as depressions or arterioscle-rotic dementia; as well as for enhancing cognition. Yet in addition, the compounds of the invention are useful in the treatment of diabetes mellitus, leukaemia and osteoporosis.

The invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions for treating disorders which are mediated by phosphodiesterases, in particular PDE4-mediated disorders, such as, for example, those mentioned in the specification of this invention or those which are apparent or known to the skilled person.

The invention also relates to the use of the compounds according to the invention for the manufacture of pharmaceutical compositions having PDE4 inhibitory activity.

The invention furthermore relates to pharmaceutical compositions for the treatment and/or prophylaxis of the illnesses mentioned comprising one or more of the compounds according to the invention.

The invention yet furthermore relates to compositions comprising one or more compounds according to this invention and a pharmaceutically acceptable carrier. Said compositions can be used in therapy, such as e.g. for treating, preventing or ameliorating one or more of the abovementioned diseases.

The invention still yet furthermore relates to pharmaceutical compositions according to this invention having PDE, particularly PDE4, inhibitory activity.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, cap-lets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, excipients, carriers, vehicles, diluents or adju-vants which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further proc-essed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1-99%. The dose for administration by inhalation is customarly between 0.01 and 3 mg per day. The customary dose in the case of systemic therapy (p.o. or i.v.) is between 0.003 and 3 mg/kg per day. In another embodiment, the dose for administration by inhalation is between 0.1 and 3 mg per day, and the dose in the case of systemic therapy (p.o. or i.v.) is between 0.03 and 3 mg/kg per day.

Biological Investigations

The second messenger cyclic AMP (cAMP) is well-known for inhibiting inflammatory and immuno-competent cells. The PDE4 isoenzyme is broadly expressed in cells involved in the initiation and propagation of inflammatory diseases (H Tenor and C Schudt, in Phosphodiesterase Inhibitors", 21-40, The Handbook of Immunopharmacology", Academic Press, 1996), and its inhibition leads to an increase of the intracellular cAMP concentration and thus to the inhibition of cellular activation (JE Souness et al., Immunopharmacology 47: 127-162, 2000).

The antiinflammatory potential of PDE4 inhibitors in vivo in various animal models has been described (MM Teixeira, TiPS 18: 164-170, 1997). For the investigation of PDE4 inhibition on the cellular level (in vitro), a large variety of proinflammatory responses can be measured. Examples are the su-peroxide production of neutrophilic (C Schudt et al., Arch Pharmacol 344: 682-690, 1991) or eosino-philic (A Hatzelmann et al., Brit J Pharmacol 114: 821-831, 1995) granulocytes, which can be measured as luminol-enhanced chemiluminescence, or the synthesis of tumor necrosis factor-α in mono-cytes, macrophages or dendritic cells (Gantner et al., Brit J Pharmacol 121: 221-231, 1997, and Pul-monary Pharmacol Therap 12: 377-386, 1999). In addition, the immunomodulatory potential of PDE4 inhibitors is evident from the inhibition of T-cell responses like cytokine synthesis or proliferation (DM Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Methods for Measuring Inhibition of PDE4 Activity

The PDE4B2 (GB no. M97515) was a gift of Prof. M. Conti (Stanford University, USA). It was ampli-fied from the original plasmid (pCMV5) via PCR with primers Rb9 (5'-GC-CAGCGTGCAAATAAT-GAAGG-3') and Rb10 (5'-AGAGGGGGATTATGTATCCAC 3') and cloned into the pCR-Bac vector (Invitrogen, Groningen, NL).

The recombinant baculovirus was prepared by means of homologous recombination in SF9 insect cells. The expression plasmid was cotransfected with Bac-N-Blue (Invitrogen, Groningen, NL) or Baculo-Gold DNA (Pharmingen, Hamburg) using a standard protocol (Pharmingen, Hamburg). Wt vi-rus-free recombinant virus supernatant was selected using plaque assay methods. After that, high-titre virus supernatant was prepared by amplifying 3 times. PDE was expressed in SF21 cells by infecting $2\times10^6$ cells/ml with an MOI (multiplicity of infection) between 1 and 10 in serum-free SF900 medium (Life Technologies, Paisley, UK). The cells were cultured at 28° C. for 48-72 hours, after which they were pelleted for 5-10 min at 1000 g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 μM leupeptin, 10 μM pepstatin A, 5 μM trypsin inhibitor) and disrupted by ultrasonication. The homogenate was then centrifuged for 10 min at 1000×g and the supernatant was stored at 80° C. until subsequent use (see below). The protein content was determined by the Bradford method (BioRad, Munich) using BSA as the standard.

PDE4B2 activity is inhibited by the said compounds in a modified SPA (scintillation proximity assay) test, supplied by Amersham Biosciences (see procedural instructions "phosphodiesterase[3H]cAMP SPA enzyme assay, code TRKQ 7090"), carried out in 96-well microtiter plates (MTP's). The test volume is 100 μl and contains 20 mM Tris buffer (pH 7.4), 0.1 mg of BSA (bovine serum albumin)/ml, 5 mM $Mg^{2+}$, 0.5 μM cAMP (including about 50,000 cpm of [3H]cAMP), 1 μl of the respective substance dilution in DMSO and sufficient recombinant PDE (1000×g supernatant, see above) to ensure that 10-20% of the cAMP is converted under the said experimental conditions. The final concentration of DMSO in the assay (1% v/v) does not substantially affect the activity of the PDE investigated. After a preincubation of 5 min at 37° C., the reaction is started by adding the substrate (cAMP) and the assay is incubated for a further 15 min; after that, it is stopped by adding SPA beads (50 μl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE activity are determined from the concentration-effect curves by means of non-linear regression.

Representative inhibitory values determined for the compounds according to the invention follow from the following table A, in which the numbers of the compounds correspond to the numbers of the Examples.

TABLE A

| Inhibition of the PDE4 activity | |
|---|---|
| Compound | $-\log IC_{50}$ (mol/l) |
| 1 | The inhibitory values of these listed |
| 2 | compounds 1 to 16 are in the range |
| 3 | from 7.24 to 9.32 |
| 4 | |
| 5 | |
| 6 | |
| 7 | |
| 8 | |
| 9 | |
| 10 | |
| 11 | |
| 12 | |
| 13 | |
| 14 | |
| 15 | |
| 16 | |
| 35 to 40, 52, 53, 55 to 67, 70 to 72, and 82 | The inhibitory values of these listed compounds 35 to 40, 52, 53, 55 to 67, 70 to 72, and 82 are in the range from 6.91 to 9.17 |
| 86, 88 to 95, 98, 101, 102, 118, 119, 124 to 127, 129 to 141, 145, 156, 158 to 160, 165, and 167 | The inhibitory values of these listed compounds 86, 88 to 95, 98, 101, 102, 118, 119, 124 to 127, 129 to 141, 145, 156, 158 to 160, 165, and 167 are in the range from 7.02 to 9.4 |

The invention claimed is:

1. A method of treating atopic eczema in a patient, comprising administering to said patient a compound of formula Ia*****

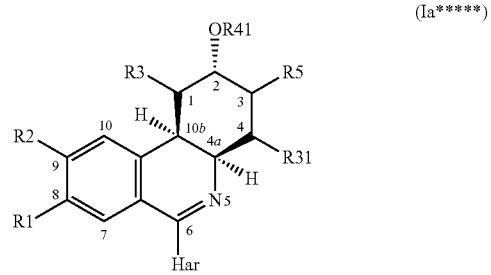

(Ia*****)

wherein
R1 is methoxy,
R2 is methoxy, ethoxy, difluoromethoxy or 2,2-difluoroethoxy,
R3 is hydrogen,
R31 is hydrogen,
R41 is hydrogen,
R5 is hydrogen,
Har is substituted by R6 and R7, and is pyridinyl, in which
R6 is oxo, and
R7 is methyl,
or a pharmaceutically acceptable salt thereof.

2. The method of treating atopic eczema in a patient according to claim 1, comprising administering to said patient a compound of formula Ia*****,
wherein
R1 is methoxy,
R2 is methoxy, ethoxy, difluoromethoxy or 2,2-difluoroethoxy,
R3 is hydrogen,
R31 is hydrogen,
R41 is hydrogen,
R5 is hydrogen,
Har is 1-methyl-1H-pyridin-2-one-5-yl,
or a pharmaceutically acceptable salt thereof.

3. The method of treating atopic eczema in a patient according to claim 1, comprising administering to said patient a compound of formula Ia*****,

SEQUENCE LISTING

```
<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
gccagcgtgc aaataatgaa gg                                              22

<210> SEQ ID NO 2
<211> LENGTH: 21
<212> TYPE: DNA
<213> ORGANISM: Homo sapiens

<400> SEQUENCE: 2
agagggggat tatgtatcca c                                               21
``` wherein
R1 is methoxy,
R2 is ethoxy, difluoromethoxy or 2,2-difluoroethoxy,
R3 is hydrogen,
R31 is hydrogen,
R41 is hydrogen,
R5 is hydrogen,
Har is 1-methyl-1H-pyridin-2-one-5-yl,
or a pharmaceutically acceptable salt thereof.

4. The method of treating atopic eczema in a patient according to claim 1, comprising administering to said patient a compound of formula Ia*****, which is selected from the group consisting of 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one and a pharmaceutically acceptable salt thereof.

5. The method of treating atopic eczema in a patient according to claim 1, comprising administering to said patient a compound of formula Ia*****, which is 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one.

* * * * *